(12) United States Patent
Hoffman et al.

(10) Patent No.: US 11,192,867 B2
(45) Date of Patent: Dec. 7, 2021

(54) MICROBIOCIDAL OXADIAZOLE DERIVATIVES

(71) Applicant: SYNGENTA PARTICIPATIONS AG, Basel (CH)

(72) Inventors: Thomas James Hoffman, Stein (CH); Daniel Stierli, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 91 days.

(21) Appl. No.: 16/306,479

(22) PCT Filed: Jun. 2, 2017

(86) PCT No.: PCT/EP2017/063451
§ 371 (c)(1),
(2) Date: Nov. 30, 2018

(87) PCT Pub. No.: WO2017/207757
PCT Pub. Date: Dec. 7, 2017

(65) Prior Publication Data
US 2019/0161460 A1 May 30, 2019

(30) Foreign Application Priority Data
Jun. 3, 2016 (EP) .................................... 16172974

(51) Int. Cl.
*C07D 271/06* (2006.01)
*A01N 43/82* (2006.01)
*C07D 413/12* (2006.01)

(52) U.S. Cl.
CPC .......... *C07D 271/06* (2013.01); *A01N 43/82* (2013.01); *C07D 413/12* (2013.01)

(58) Field of Classification Search
CPC .............................. C07D 271/06; A01N 43/82
See application file for complete search history.

(56) References Cited

FOREIGN PATENT DOCUMENTS

| WO | 2010/003923 A1 | 1/2010 |
|---|---|---|
| WO | 2012/038851 A1 | 3/2012 |
| WO | 2013/008162 A1 | 1/2013 |
| WO | 2013/066835 A2 | 5/2013 |
| WO | 2015/185485 A1 | 12/2015 |
| WO | 2017/081311 A1 | 5/2017 |
| WO | 2017/081312 A1 | 5/2017 |
| WO | 2017/085098 A1 | 5/2017 |
| WO | 2017/085100 A1 | 5/2017 |
| WO | WO 2017/076935 | * 5/2017 |
| WO | 2017/093019 A1 | 6/2017 |
| WO | 2017/110861 A1 | 6/2017 |
| WO | 2017/110862 A1 | 6/2017 |
| WO | 2017/110863 A1 | 6/2017 |
| WO | 2017/110864 A1 | 6/2017 |
| WO | 2017/110865 A1 | 6/2017 |
| WO | 2017/111152 A1 | 6/2017 |
| WO | 2017/169893 A1 | 10/2017 |
| WO | 2017/213252 A1 | 12/2017 |
| WO | 2017/222951 A1 | 12/2017 |
| WO | 2017/222952 A1 | 12/2017 |
| WO | 2018/056340 A1 | 3/2018 |
| WO | 2018/114393 A1 | 6/2018 |
| WO | 2018/117034 A1 | 6/2018 |
| WO | 2018/118781 A1 | 6/2018 |
| WO | 2018/153730 A1 | 8/2018 |
| WO | 2018/184970 A1 | 10/2018 |
| WO | 2018/188962 A1 | 10/2018 |
| WO | 2018/202428 A1 | 11/2018 |
| WO | 2018/202487 A1 | 11/2018 |
| WO | 2018/202491 A1 | 11/2018 |

OTHER PUBLICATIONS

Webster's New World Dictionary, second college edition, The World Publishing Co., New York, p. 1127 (1972).*
EP Application 15197814.5 (filing date Dec. 3, 1015), selected pp. 1-2, 18-19 and 58-64.*
International Search Report for International Patent Application No. PCT/EP2017/063451 dated Jul. 6, 2017.

* cited by examiner

*Primary Examiner* — John Pak
(74) *Attorney, Agent, or Firm* — Bakerhostetler; Toni-Junell Herbert

(57) ABSTRACT

Compounds of the formula (I) wherein the substituents are as defined in claim 1, useful as pesticides, especially as fungicides.

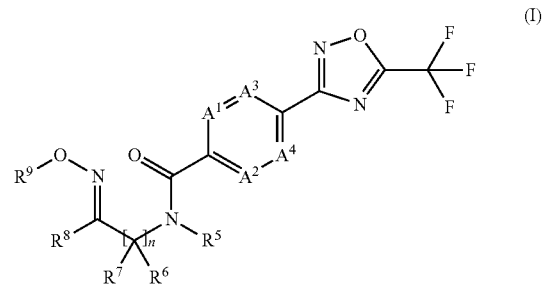

17 Claims, No Drawings

MICROBIOCIDAL OXADIAZOLE DERIVATIVES

CROSS-REFERENCE TO RELATED APPLICATIONS

This application is a 371 National Stage application of International Application No. PCT/EP2017/063451, filed Jun. 2, 2017, which claims priority to European Patent Application No. 16172974.4 filed Jun. 3, 2016, the entire contents of which applications are hereby incorporated by reference.

The present invention relates to microbiocidal oxadiazole derivatives, e.g., as active ingredients, which have microbiocidal activity, in particular, fungicidal activity. The invention also relates to agrochemical compositions which comprise at least one of the oxadiazole derivatives, to processes of preparation of these compounds and to uses of the oxadiazole derivatives or compositions in agriculture or horticulture for controlling or preventing infestation of plants, harvested food crops, seeds or non-living materials by phytopathogenic microorganisms, preferably fungi.

WO 2015/185485 describes the use of substituted oxadiazoles for combating phytopathogenic fungi.

According to the present invention, there is provided a compound of formula (I):

wherein
n is 0, 1 or 2;
$A^1$ represents N or $CR^1$, wherein $R^1$ is hydrogen, halogen, methyl, ethyl, difluoromethyl, trifluoromethyl, methoxy, ethoxy, or difluoromethoxy;
$A^2$ represents N or $CR^2$, wherein $R^2$ is hydrogen, halogen, methyl, ethyl, difluoromethyl, trifluoromethyl, methoxy, ethoxy, or difluoromethoxy;
$A^3$ represents N or $CR^3$, wherein $R^3$ is hydrogen or halogen; and
$A^4$ represents N or $CR^4$, wherein $R^4$ is hydrogen or halogen;
wherein no more than two of $A^1$ to $A^4$ are N;
$R^5$ is hydrogen, $C_{1-4}$alkyl, $C_{3-6}$cycloalkyl or $C_{1-4}$alkoxy;
$R^6$ and $R^7$ are independently selected from hydrogen, cyano, $C_{1-4}$alkyl, $C_{1-4}$haloalkyl, $C_{3-6}$cycloalkyl and $C_{1-4}$alkoxy;
$R^8$ represents hydrogen, $C_{1-6}$alkyl, $C_{2-6}$alkenyl, $C_{2-6}$alkynyl, $C_{1-6}$haloalkyl, $C_{3-8}$cycloalkyl or phenyl;
$R^9$ represents hydrogen, $C_{1-12}$alkyl, $C_{2-6}$alkenyl, $C_{2-6}$alkynyl, $C_{1-4}$haloalkyl, $C_{2-4}$haloalkenyl, hydroxy$C_{1-4}$alkyl, cyano$C_{1-4}$alkyl, $C_{1-4}$alkoxy$C_{1-4}$alkyl, hydroxycarbonyl$C_{1-4}$alkyl, $C_{1-4}$alkoxycarbonyl$C_{1-4}$alkyl, amino$C_{1-4}$alkyl, $C_{3-8}$cycloalkyl, $C_{3-8}$cycloalkyl$C_{1-3}$alkyl, phenyl, phenyl$C_{1-4}$alkyl, heterocyclyl or heterocyclyl$C_{1-4}$alkyl wherein the heterocyclyl moiety is a 4- to 6-membered non-aromatic ring which comprises 1, 2 or 3 heteroatoms individually selected from N, O and S, and wherein $C_{3-8}$cycloalkyl, phenyl and heterocyclyl moieties are optionally substituted by 1, 2, or 3 substituents, which may be the same or different, selected from $R^{10}$, or 1, 2, 3, 4 or 5 substituents, which may be the same or different, selected from $R^{11}$;
$R^{10}$ represents cyano, nitro, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{1-6}$alkylthio, $C_{1-4}$alkoxycarbonyl$C_{1-4}$alkyl, hydroxycarbonyl$C_{1-4}$alkyl, or $C_{3-8}$cycloalkyl; and
$R^{11}$ represents halogen;
or
a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I). Such an agricultural composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, hydroxy means an —OH group.

As used herein, nitro means an —$NO_2$ group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. $C_{1-12}$alkyl and $C_{1-4}$alkyl are to be construed accordingly. Examples of $C_{1-6}$alkyl include, but are not limited to, methyl, ethyl, n-propyl, 1-methylethyl (iso-propyl), n-butyl, and 1-dimethylethyl (t-butyl). A "$C_{1-6}$alkylene" group refers to the corresponding definition of $C_{1-6}$alkyl (and $C_{1-12}$alkyl, $C_{1-4}$alkyl and $C_{1-3}$alkyl), except that such radical is attached to the rest of the molecule by two single bonds. Examples of $C_{1-6}$alkylene, include, but are not limited to, —$CH_2$—, —$CH_2CH_2$— and —$(CH_2)_3$—.

As used herein, the term "$C_{1-6}$alkoxy" refers to a radical of the formula —$OR_a$ where $R_a$ is a $C_{1-6}$alkyl radical as generally defined above. $C_{1-4}$alkoxy is to be construed accordingly. Examples of $C_{1-6}$alkoxy include, but are not limited to, methoxy, ethoxy, propoxy, iso-propoxy, t-butoxy.

As used herein, the term "$C_{1-6}$haloalkyl" refers to a $C_{1-6}$alkyl radical as generally defined above substituted by one or more of the same or different halogen atoms. $C_{1-4}$haloalkyl is to be construed accordingly. Examples of $C_{1-6}$haloalkyl include, but are not limited to fluoromethyl, fluoroethyl, difluoromethyl, trifluoromethyl, and 2,2,2-trifluoroethyl.

As used herein, the term "$C_{1-6}$haloalkoxy" refers to a $C_{1-6}$alkoxy group as defined above substituted by one or more of the same or different halogen atoms. $C_{1-4}$haloalkoxy is to be construed accordingly. Examples of $C_{1-6}$haloalkoxy include, but are not limited to, fluoromethoxy, difluoromethoxy, fluoroethoxy, trifluoromethoxy, and 2,2,2-trifluoroethoxy.

As used herein, the term "$C_{2-6}$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. $C_{2-4}$alkenyl is to be construed accordingly. Examples of $C_2$-$C_6$alkenyl include, but are not limited to, prop-1-enyl, allyl (prop-2-enyl), and but-1-enyl.

As used herein, the term "$C_{2-4}$haloalkenyl" refers to a $C_{2-4}$alkenyl radical as generally defined above substituted by one or more of the same or different halogen atoms.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$alkynyl" is to be construed accordingly. Examples of $C_{2-6}$alkynyl include, but are not limited to, prop-1-ynyl, propargyl (prop-2-ynyl), and but-1-ynyl.

As used herein, the term "$C_{1-4}$alkoxy$C_{1-4}$alkyl" refers to radical of the formula $R_b$—O—$R_a$— where $R_b$ is a $C_{1-4}$alkyl radical as generally defined above, and $R_a$ is a $C_{1-4}$alkylene radical as generally defined above.

As used herein, the term "hydroxy$C_{1-6}$alkyl" refers to a $C_{1-6}$alkyl radical as generally defined above substituted by one or more hydroxyl groups. Hydroxy$C_{1-4}$alkyl is to be construed accordingly.

As used herein, the term "cyano$C_{1-6}$alkyl" refers to refers to a $C_{1-6}$alkyl radical as generally defined above substituted by one or more cyano groups. Cyano$C_{1-4}$alkyl is to be construed accordingly.

As used herein, the term "hydroxycarbonyl$C_{1-6}$alkyl" refers to a radical of the formula —$R_a$C(O)OH where $R_a$ is a $C_{1-6}$alkylene radical as generally defined above. The terms "hydroxycarbonyl$C_{1-4}$alkyl" and "hydroxycarbonyl$C_{1-2}$alkyl" are to be construed accordingly. Examples of hydroxycarbonyl$C_{1-6}$alkyl include, but are not limited to, hydroxycarbonylmethyl.

As used herein, the term "$C_{1-4}$alkoxycarbonyl" refers to a radical of the formula —C(O)O$R_a$ where $R_a$ is a $C_{1-4}$alkyl radical as generally defined above.

As used herein, the term "$C_{1-4}$alkoxycarbonyl$C_{1-4}$alkyl" refers to a radical of the formula —$R_b$C(O)O$R_a$ where $R_a$ is a $C_{1-4}$alkyl radical as generally defined above and $R_b$ is a $C_{1-4}$alkylene radical as defined above.

As used herein, the term "$C_{1-6}$alkylthio" refers to a radical of the formula —S$R_a$ where $R_a$ is a $C_{1-6}$alkyl radical as generally defined above. $C_{1-4}$alkylthio is to be construed accordingly.

As used herein, the term "amino$C_{1-4}$alkyl" refers to a radical of the formula —$R_a$NH$_2$, where $R_a$ is a $C_{1-4}$alkylene radical as defined above. The term "amino$C_{1-2}$alkyl" is to be construed accordingly. Examples of amino$C_{1-4}$alkyl include, but are not limited to, aminoethyl.

As used herein, the term "$C_{3-8}$cycloalkyl" refers to a stable, monocyclic ring radical which is saturated or partially unsaturated and contains 3 to 8 carbon atoms. $C_{3-6}$cycloalkyl is to be construed accordingly. Examples of $C_{3-8}$cycloalkyl include, but are not limited to, cyclopropyl, cyclobutyl, cyclopentyl and cyclohexyl.

As used herein, the term "$C_{3-8}$cycloalkyl$C_{1-3}$alkyl" refers to a $C_{3-8}$cycloalkyl ring as defined above attached to the rest of the molecule by a $C_{1-3}$alkylene radical as defined above. The terms "$C_{3-6}$cycloalkyl$C_{1-3}$alkyl" and "$C_{3-4}$cycloalkyl$C_{1-2}$alkyl" are to be construed accordingly. Examples of $C_{3-8}$cycloalkyl$C_{1-3}$alkyl include, but are not limited to cyclopropyl-methyl, cyclobutyl-ethyl, and cyclopentyl-propyl.

As used herein, the term "phenyl$C_{1-4}$alkyl" refers to a phenyl ring attached to the rest of the molecule by a $C_{1-4}$alkylene radical as defined above. Examples of phenyl$C_{1-4}$alkyl include, but are not limited to, benzyl.

As used herein, the term "heterocyclyl" or "heterocyclic" refers to a stable, 4- to 6-, and preferably a 5- or 6-membered non-aromatic monocyclic ring radical which comprises 1, 2, or 3 heteroatoms individually selected from nitrogen, oxygen and sulfur. The heterocyclyl radical may be bonded to the rest of the molecule via a carbon atom or heteroatom. Examples of heterocyclyl include, but are not limited to, pyrrolinyl, pyrrolidyl, tetrahydrofuranyl, tetrahydrothienyl, tetrahydrothiopyranyl, piperidyl, piperazinyl, oxetanyl, tetrahydropyranyl, dioxolanyl, morpholinyl, δ-lactamyl, and perhydroazepinyl.

As used herein, the term "heterocyclyl$C_{1-4}$alkyl" refers to a heterocyclic ring as defined above which is attached to the rest of the molecule by a $C_{1-4}$alkylene radical as defined above.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I).

In each case, the compounds of formula (I) according to the invention are in free form, in oxidized form as an N-oxide, in covalently hydrated form, or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents n, $A^1$, $A^2$, $A^3$, $A^4$, $R^1$, $R^2$, $R^3$, $R^4$, $R^5$, $R^6$, $R^7$, $R^8$, $R^9$, $R^{10}$ and $R^{11}$, with reference to the compounds of formula (I) according to the invention. For any one of these substituents, any of the definitions given below may be combined with any definition of any other substituent given below or elsewhere in this document.

n represents 0, 1 or 2. In some embodiments of the invention, n is 0. In other embodiments of the invention, n is 1. Preferably, n represents 1 or 2.

$A^1$ represents N or $CR^1$, wherein $R^1$ is hydrogen, halogen, methyl, ethyl, difluoromethyl, trifluoromethyl, methoxy, ethoxy, or difluoromethoxy. Preferably, $A^1$ is $CR^1$ and $R^1$ is hydrogen or halogen. More preferably, $A^1$ is $CR^1$ and $R^1$ is hydrogen or fluoro.

$A^2$ represents N or $CR^2$, wherein $R^2$ is hydrogen, halogen, methyl, ethyl, difluoromethyl, trifluoromethyl, methoxy, ethoxy, or difluoromethoxy. Preferably, $A^2$ is $CR^2$ and $R^2$ is hydrogen.

$A^3$ represents N or $CR^3$, wherein $R^3$ is hydrogen or halogen. Preferably, $A^3$ is $CR^3$ and $R^3$ is hydrogen or halogen. More preferably, $A^3$ is $CR^3$ and $R^3$ is hydrogen or fluoro.

$A^4$ represents N or $CR^4$, wherein $R^4$ is hydrogen or halogen. Preferably, $A^2$ is $CR^4$ and $R^4$ is hydrogen.

In accordance with the compounds of the invention, no more than two of $A^1$ to $A^4$ are N.

Preferably, $A^1$ to $A^4$ are all C—H, $A^2$ to $A^4$ are all C—H and $A^1$ is $CR^1$ wherein $R^1$ is fluoro, or $A^1$, $A^3$ and $A^4$ are all C—H and $A^2$ is $CR^2$ wherein $R^3$ is fluoro, or $A^1$, $A^2$ and $A^4$ are all C—H and $A^3$ is $CR^3$ wherein $R^3$ is fluoro. Most preferably, $A^1$ to $A^4$ are all C—H.

$R^5$ is hydrogen, $C_{1-4}$alkyl, $C_{3-6}$cycloalkyl or $C_{1-4}$alkoxy. Preferably, $R^5$ is hydrogen, $C_{1-4}$alkyl, or $C_{3-6}$cycloalkyl. More preferably, hydrogen, methyl or cyclopropyl. More preferably still, $R^5$ is hydrogen.

$R^6$ and $R^7$ are independently selected from hydrogen, cyano, $C_{1-4}$alkyl, $C_{1-4}$haloalkyl, $C_{3-6}$cycloalkyl and $C_{1-4}$alkoxy. Preferably, $R^6$ and $R^7$ are independently selected from hydrogen, $C_{1-4}$alkyl and $C_{1-4}$alkoxy. More preferably, $R^6$ and $R^7$ are independently selected from hydrogen, methyl and methoxy. Even more preferably, at least one of $R^6$ and $R^7$ is hydrogen and the other is selected from hydrogen, methyl and methoxy, preferably hydrogen and methyl. In some embodiments of the invention, $R^6$ and $R^7$ are both methyl. In a preferred embodiment of the invention, $R^6$ and $R^7$ are both hydrogen.

$R^8$ represents hydrogen, $C_{1-6}$alkyl, $C_{2-6}$alkenyl, $C_{2-6}$alkynyl, $C_{1-6}$haloalkyl, $C_{3-8}$cycloalkyl or phenyl. Preferably, $R^8$ is hydrogen or $C_{1-4}$alkyl. More preferably, $R^8$ is hydrogen or methyl. Most preferably, $R^8$ is hydrogen.

$R^9$ represents hydrogen, $C_{1-12}$alkyl, $C_{2-6}$alkenyl, $C_{2-6}$alkynyl, $C_{1-4}$haloalkyl, $C_{2-4}$haloalkenyl, hydroxy$C_{1-4}$alkyl, cyano$C_{1-4}$alkyl, $C_{1-4}$alkoxy$C_{1-4}$alkyl, hydroxycarbonyl$C_{1-4}$alkyl, $C_{1-4}$alkoxycarbonyl$C_{1-4}$alkyl, $C_{3-8}$cycloalkyl, $C_{3-8}$cycloalkyl$C_{1-3}$alkyl, phenyl, phenyl$C_{1-4}$alkyl, heterocyclyl or heterocyclyl$C_{1-4}$alkyl, wherein the heterocyclyl moiety is a 4- to 6-membered non-aromatic ring which comprises 1, 2 or 3 heteroatoms individually selected from N, O and S, and wherein $C_{3-8}$cycloalkyl, phenyl and heterocyclyl moieties are optionally substituted by 1, 2, or 3 substituents, which may be the same or different, selected from $R^{10}$, or 1, 2, 3, 4 or 5 substituents, which may be the same or different, selected from $R^{11}$.

Preferably, $R^9$ is hydrogen, $C_{1-12}$alkyl (e.g., $C_{1-6}$alkyl), $C_{1-4}$haloalkyl, hydroxy$C_{1-4}$alkyl, $C_{2-6}$alkenyl, $C_{2-6}$alkynyl, $C_{2-4}$haloalkenyl, $C_{1-4}$alkoxycarbonyl$C_{1-4}$alkyl, $C_{3-8}$cycloalkyl$C_{1-3}$alkyl, phenyl, benzyl, oxetanyl, tetrahydrofuranyl or tetrahydropyranyl, wherein phenyl moieties are optionally substituted by 1, 2 or 3 substituents, which may be the same or different, selected from $R^{10}$, or 1, 2, 3, 4 or 5 substituents, which may be the same or different, selected from $R^{11}$. More preferably, $R^9$ is hydrogen, $C_{1-6}$alkyl, $C_{1-4}$haloalkyl, $C_{2-6}$alkenyl, $C_{2-6}$alkynyl, or $C_{3-8}$cycloalkyl$C_{1-3}$alkyl. Even more preferably, $R^9$ is $C_{1-4}$alkyl, $C_{1-3}$haloalkyl, or $C_{3-6}$cycloalkyl$C_{1-3}$alkyl, in particular methyl, ethyl, isopropyl, t-butyl, 2,2,2-trifluoroethyl or cyclopropylmethyl.

$R^{10}$ represents cyano, nitro, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{1-6}$alkylthio, $C_{1-4}$alkoxycarbonyl$C_{1-4}$alkyl, or $C_{3-8}$cycloalkyl. Preferably, $R^{10}$ represents cyano, nitro, $C_{1-4}$alkyl, $C_{2-4}$alkenyl, $C_{2-4}$alkynyl, $C_{1-4}$haloalkyl, $C_{1-4}$alkoxy, $C_{1-4}$haloalkoxy, $C_{1-4}$alkylthio, $C_{1-4}$alkoxycarbonyl$C_{1-2}$alkyl, or $C_{3-6}$cycloalkyl. More preferably, $R^{10}$ represents nitro, methyl, methoxy, methoxycarbonylmethyl or trifluoromethyl.

$R^{11}$ represents halogen. Preferably, $R^{11}$ is selected from fluoro, chloro and bromo.

Preferably, the compound according to formula (I) is selected from a compound 1.1 to 1.171 listed in Table T1 (below).

Preferably, in a compound according to formula (I) of the invention, n is 0 or 1;
$A^1$ to $A^4$ are all C—H, $A^2$ to $A^4$ are all C—H and $A^1$ is $CR^1$ wherein $R^1$ is fluoro, or $A^1$, $A^2$ and $A^4$ are all C—H and $A^3$ is $CR^3$ wherein $R^3$ is fluoro;
$R^5$ is hydrogen or methyl;
$R^6$ and $R^7$ are independently selected from hydrogen, methyl and methoxy;
$R^8$ is hydrogen or methyl;
$R^9$ is hydrogen, $C_{1-12}$alkyl, $C_{1-4}$haloalkyl, hydroxy$C_{1-4}$alkyl, $C_{2-6}$alkenyl, $C_{2-6}$alkynyl, $C_{2-4}$haloalkenyl, $C_{1-4}$alkoxycarbonyl$C_{1-4}$alkyl, phenyl, benzyl, oxetanyl, tetrahydrofuranyl or tetrahydropyranyl, wherein phenyl moieties are optionally substituted by 1, 2 or 3 substituents, which may be the same or different, selected from $R^{10}$, or 1, 2, 3, 4 or 5 substituents, which may be the same or different, selected from $R^{11}$.
$R^{10}$ represents nitro, methyl, methoxy, methoxycarbonylmethyl or trifluoromethyl;
$R^{11}$ represents halogen.

More preferably, n is 0 or 1;
$A^1$ to $A^4$ are all C—H, $A^2$ to $A^4$ are all C—H and $A^1$ is $CR^1$ wherein $R^1$ is fluoro, or $A^1$, $A^2$ and $A^4$ are all C—H and $A^3$ is $CR^3$ wherein $R^3$ is fluoro;
$R^5$ is hydrogen;
$R^6$ is hydrogen;
$R^7$ is hydrogen, methyl or methoxy;
$R^8$ is hydrogen or methyl;
$R^9$ is hydrogen, $C_{1-12}$alkyl, $C_{1-4}$haloalkyl, hydroxy$C_{1-4}$alkyl, $C_{2-6}$alkenyl, $C_{2-6}$alkynyl, $C_{2-4}$haloalkenyl, $C_{1-4}$alkoxycarbonyl$C_{1-4}$alkyl, phenyl, benzyl, oxetanyl, tetrahydrofuranyl or tetrahydropyranyl, wherein phenyl moieties are optionally substituted by 1, 2 or 3 substituents, which may be the same or different, selected from $R^{10}$, or 1, 2, 3, 4 or 5 substituents, which may be the same or different, selected from $R^{11}$;
$R^{10}$ represents nitro, methyl, methoxy, methoxycarbonylmethyl or trifluoromethyl;
$R^{11}$ represents halogen.

Even more preferably, n is 0 or 1;
$A^1$ to $A^4$ are all C—H, $A^2$ to $A^4$ are all C—H and $A^1$ is $CR^1$ wherein $R^1$ is fluoro, or $A^1$, $A^2$ and $A^4$ are all C—H and $A^3$ is $CR^3$ wherein $R^3$ is fluoro;
$R^5$ is hydrogen;
$R^6$ is hydrogen;
$R^7$ is hydrogen, methyl or methoxy;
$R^8$ is hydrogen or methyl;
$R^9$ is hydrogen, $C_{1-6}$alkyl, $C_{2-6}$alkenyl or $C_{2-6}$alkynyl.

Still more preferably, n is 0 or 1;
$A^1$ to $A^4$ are all C—H, $A^2$ to $A^4$ are all C—H and $A^1$ is $CR^1$ wherein $R^1$ is fluoro, or $A^1$, $A^2$ and $A^4$ are all C—H and $A^3$ is $CR^3$ wherein $R^3$ is fluoro;
$R^5$ is hydrogen;
$R^6$ is hydrogen;
$R^7$ is hydrogen, methyl or methoxy;
$R^8$ is hydrogen or methyl;
$R^9$ is hydrogen, methyl, ethyl or propyn-3-yl.

In a particularly preferred set of embodiments, in a compound according to formula (I) of the invention, n is 1 or 2;

$A^1$ to $A^4$ are all C—H;

$R^5$ is hydrogen, methyl or cyclopropyl;

$R^6$ is hydrogen;

$R^7$ is hydrogen or methyl;

$R^8$ is hydrogen;

$R^9$ is methyl, ethyl, isopropyl, t-butyl, 2,2,2-trifluoroethyl or cyclopropylmethyl.

Preferably, the compound of formula (I) according to the invention is selected from a compound 1.1 to 1.171 described in Table T1 (below).

The compounds of the present invention may be enantiomers of the compound of formula (I) (e.g., when n=1) as represented by formula (Ia) or formula (Ib), wherein $R^6$ and $R^7$ are different.

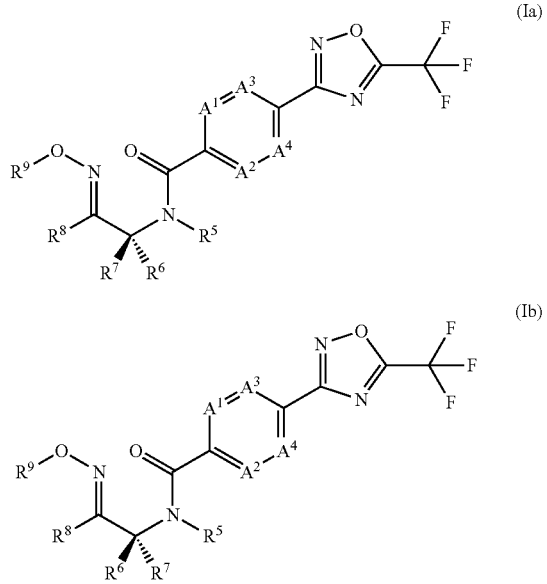

Likewise, the compounds of the present invention may be diastereomers of the compound of formula (I) when n is 2, and wherein at each of the two carbon positions bound to $R^6$ and $R^7$, $R^6$ and $R^7$ are different.

The compounds of the present invention may also be geometrical isomers ((E) or (Z)) of the compound of formula (I) as represented by a formula (Ic) or a formula (Id).

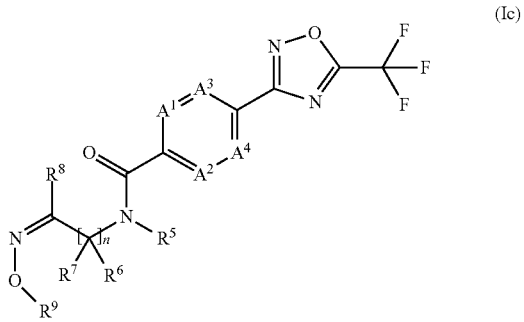

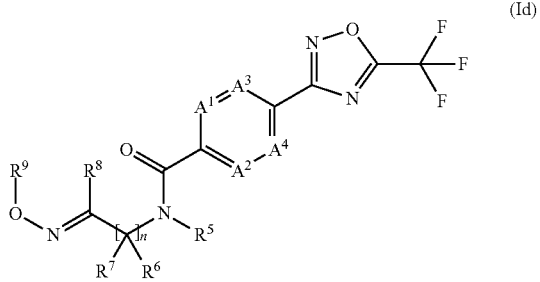

It is understood that when in aqueous media, the compounds of formula (I) according to the invention may be present in a reversible equilibrium with the corresponding covalently hydrated forms (i.e., the compounds of formula (I-I) and formula (I-II) as shown below), which may exist in tautomeric form as the compounds of formula (I-Ia) and formula (I-IIa), at the CF$_3$-oxadiazole motif. This dynamic equilibrium may be important for the biological activity of the compounds of formula (I), at the CF$_3$-oxadiazole motif. This dynamic equilibrium may be important for the biological activity of the compounds of formula (I). The designations of n, $A^1$, $A^2$, $A^3$, $A^4$, $R^1$, $R^2$, $R^3$, $R^4$, $R^5$, $R^6$, $R^7$, $R^8$, $R^9$, $R^{10}$ and $R^{11}$, with reference to the compounds of formula (I) of the present invention apply generally to the compounds of formula (I-I) and formula (I-II), as do the specific disclosures of combinations of n, $A^1$, $A^2$, $A^3$, $A^4$, $R^1$, $R^2$, $R^3$, $R^4$, $R^5$, $R^6$, $R^7$, $R^8$, $R^9$, $R^{10}$ and $R^{11}$, as represented by the compounds described in Tables 1.1 to 1.18, below, or the compounds 1.1 to 1.171 described in Table T1 (below).

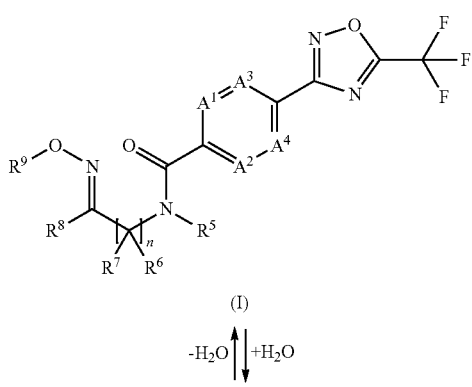

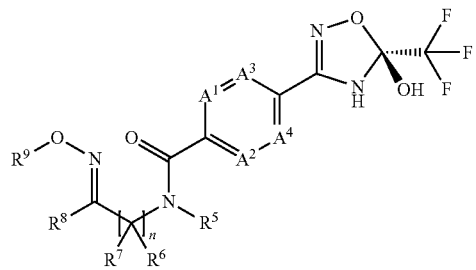

(I-I)

⇅ tautomerism

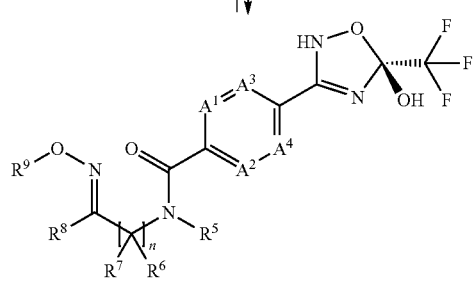

(I-Ia)

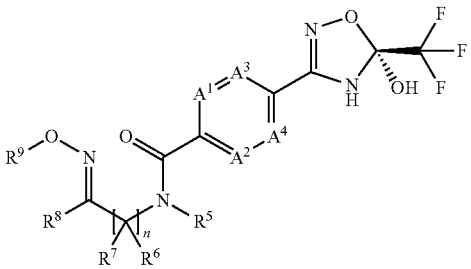

(I-II)

⇅

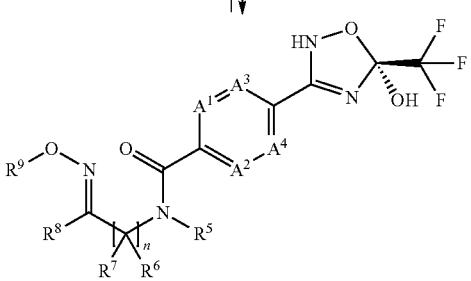

(I-IIa)

Compounds of the present invention can be made as shown in the following schemes, in which, unless otherwise stated, the definition of each variable is as defined above for a compound of formula (I).

The compounds of formula (I) can be obtained by an amide coupling transformation with compounds of formula (A) and compounds of formula (B) by activating the carboxylic acid function of the compounds of formula (A), a process that usually takes place by converting the —OH of the carboxylic acid into a good leaving group, such as a chloride group, for example by using (COCl)$_2$ or SOCl$_2$, prior to treatment with the compounds of formula (B), preferably in a suitable solvent (e.g., dimethylformamide, dichloromethane or tetrahydrofuran), preferably at a temperature of between 25° C. and 100° C., and optionally in the presence of a base such as triethylamine or N,N-diisopropylethylamine, or under conditions described in the literature for an amide coupling. This is shown in Scheme 1 below. For examples, see Valeur, E.; Bradley, M. *Chem. Soc. Rev.* (2009), 38, 606 and Chinchilla, R., Najera, C. *Chem. Soc. Rev.* (2011), 40, 5084. Compounds of formula (A) can be made by known methods from known compounds or are commercially available. For examples, see: Liu, K. et al. *J. Med. Chem.* (2008), 51, 7843 and WO 2013/008162 A1. Compounds of formula (B) are known compounds or are commercially available. For examples, see: Liu, K. et al. *J. Med. Chem.* (2008), 51, 7843 and WO 2009/030467 A1 and DE3306197.

Scheme 1

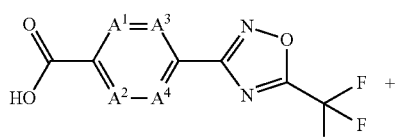

(A)

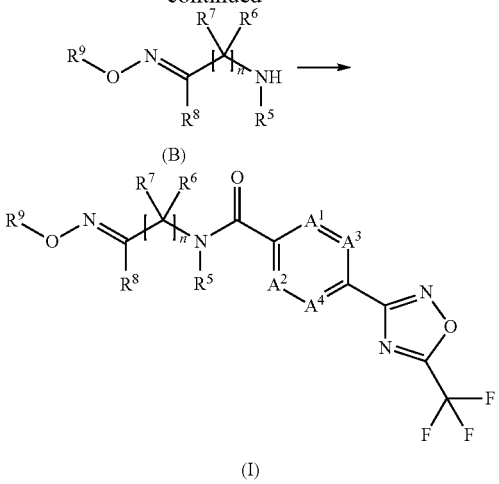

(B)

(I)

Alternatively, compounds of formula (I) can be prepared from compounds of formula (C) by treatment with trifluoroacetic anhydride, trifluoroacetyl fluoride or trifluoroacetyl chloride, in a suitable solvent, such as tetrahydrofuran, at a temperature between 0° C. and 25° C. For related examples, see Kitamura, S. et al. *Chem. Pharm. Bull.* (2001), 49, 268. This is shown in Scheme 2.

Scheme 2

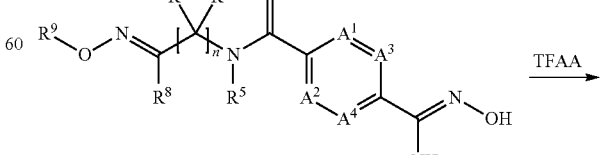

(C)

TFAA →

-continued

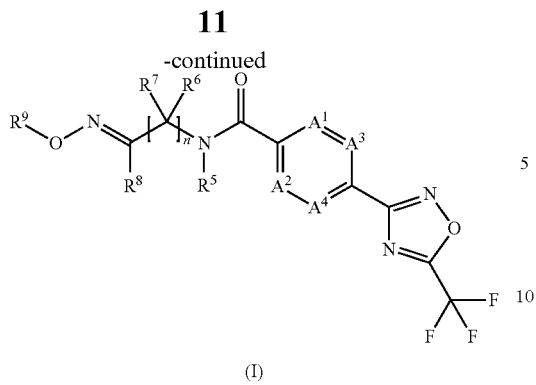

(I)

Compounds of formula (C) can be prepared from compounds of formula (D) by treating them with a hydroxylamine hydrochloride salt in the presence of a base, such as sodium carbonate, in a suitable solvent, such as methanol, at a temperature between 0° C. and 100° C. For related examples, see Kitamura, S. et al. *Chem. Pharm. Bull.* (2001), 49, 268. This is shown in Scheme 3.

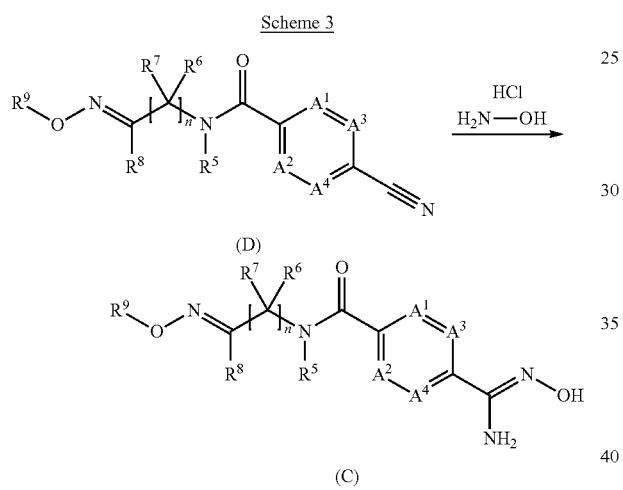

Compounds of formula (D) can be made by known methods from known compounds. For examples, see: Chobanian, H. R. et al *Tet. Lett.* (2006), 47, 3303; or Makovec, F. et al *J. Med. Chem.* (1992), 35, 3633.

Alternatively, compounds of formula (I) can be prepared from compounds of formula (E) by treating them with compounds of formula (K) in the presence of a base in a suitable solvent at a temperature between 0° C. and 50° C. This is shown in Scheme 4.

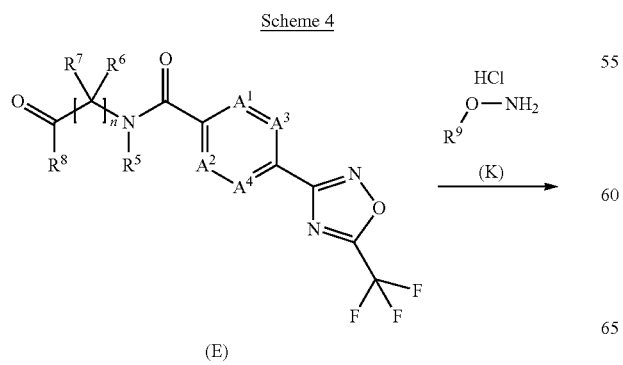

-continued

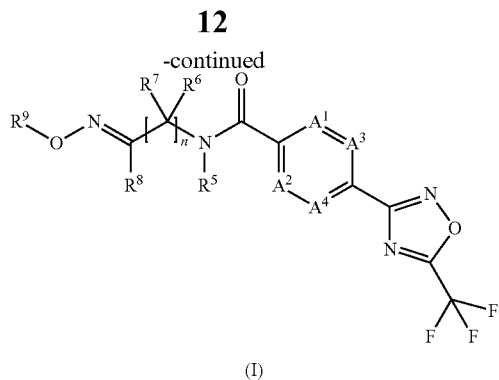

(I)

The compounds of formula (E) may be prepared by oxidizing the corresponding alcohols of formula (F). Advantageous oxidation procedures can be based on sulphur based oxidation agents (in the literature referred to, for example, as Swern-oxidation or Pfizer-Moffat-oxidation), metal based oxidation agents or hydrogen peroxide in the presence of metal catalysts, such as Na₂WO₄ (c.f., e.g., R. Noyori, Bull. *Chem. Soc. Jpn.* 1999, 72, 2287-2306). This is shown in Scheme 5.

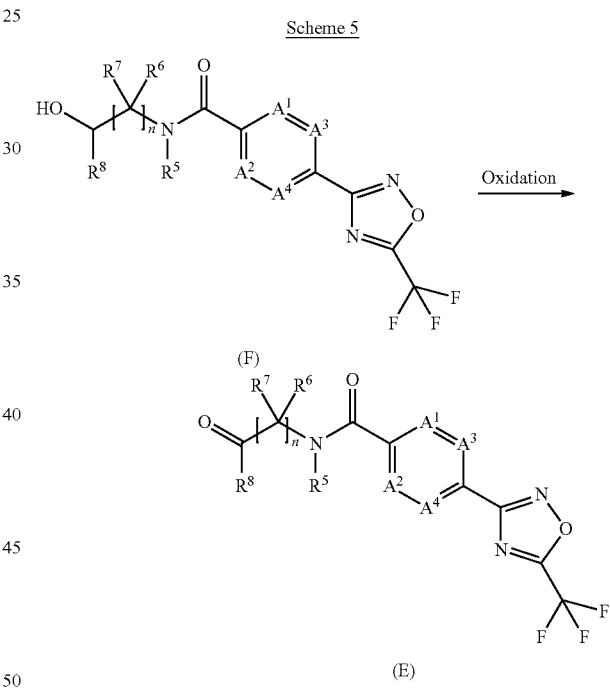

The compounds of formula (F) can be obtained by an amide coupling transformation with compounds of formula (A) and compounds of formula (G) by activating the carboxylic acid function of the compounds of formula (A) as described in scheme 1. This is shown in Scheme 6.

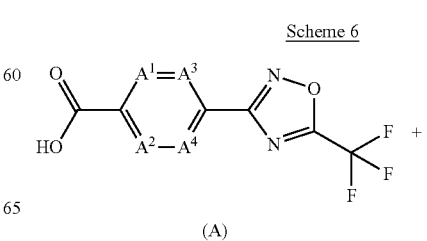

-continued

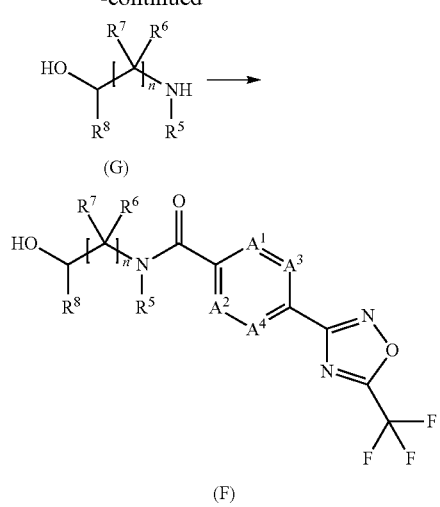

The compounds of formula (E) can also be obtained by an amide coupling transformation with compounds of formula (A) and compounds of formula (H) by activating the carboxylic acid function of the compounds of formula (A) as described in scheme 1. This is shown in Scheme 7.

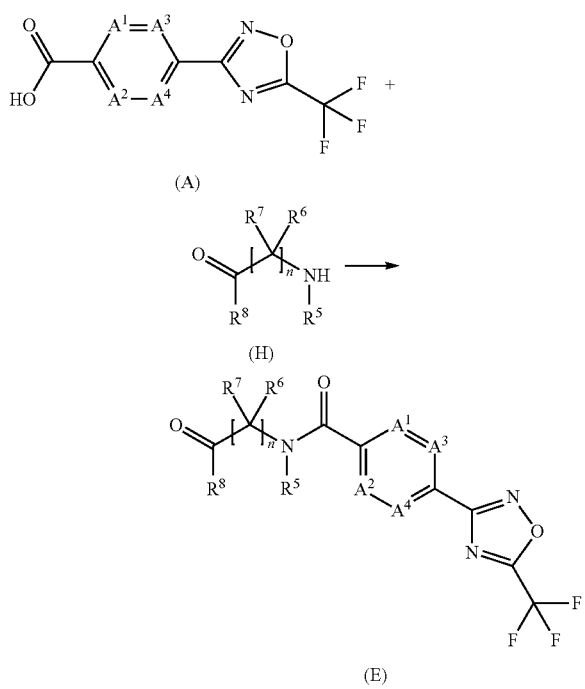

Compounds of formula (Ie) where n is 0 can be obtained from compounds of formula (i) by treating them with a compound of formula (K) in the presence of a base, such as triethylamine or N,N-diisopropylethylamine, in a suitable solvent, such as dichloromethane, preferably at a temperature of between 0° C. and 40° C. For related examples, see Petitjean, A. et al. *Organic Letters* (2011), Vol. 13, No. 19, 5160. This is shown in Scheme 8.

Scheme 8

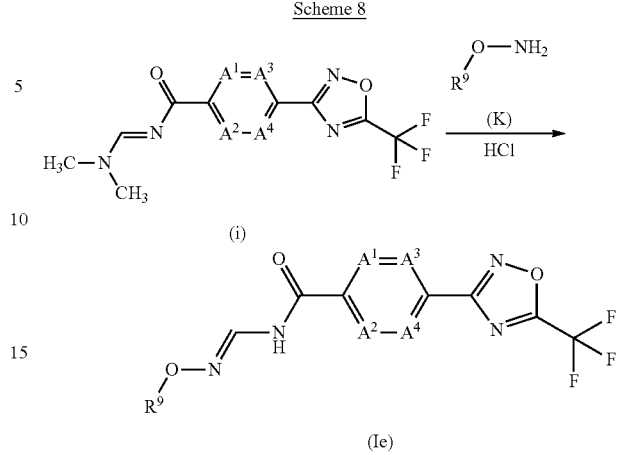

Compounds of formula (i) can be obtained from compounds of formula (L) by reacting them with N,N-dimethylformamide dimethylacetal (DMF-DMA), in a suitable solvent, such as benzene, toluene or the like, preferably at a temperature of between 50° C. and 140° C. whilst the methanol by-product is distilled off. For related examples, see Petitjean, A. et al. *Organic Letters* (2011), Vol. 13, No. 19, 5160. This is shown in Scheme 9.

Scheme 9

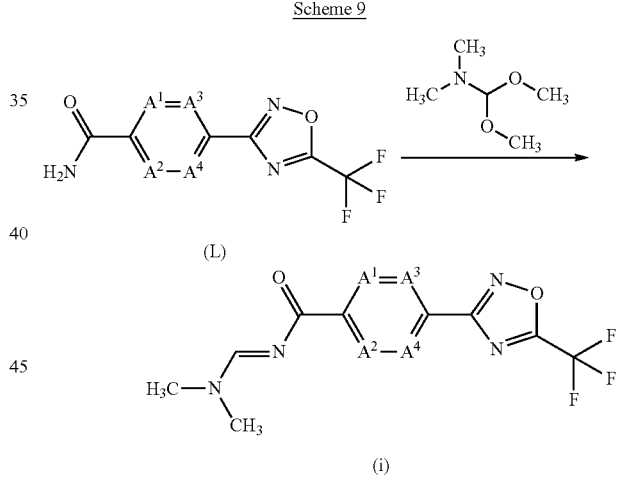

The compounds of formula (L) can be made by an amide coupling transformation with compounds of formula (A) and ammonia by activating the carboxylic acid function of the compounds of formula (A) as described in Scheme 1. This is shown in Scheme 10.

Scheme 10

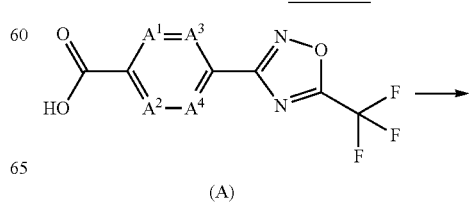

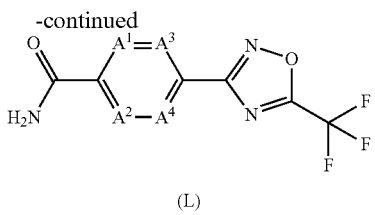

(L)

As already indicated, surprisingly, it has now been found that the novel compounds of formula (I) of the present invention have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" where used means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example:

Absidia corymbifera, Alternaria spp, Aphanomyces spp, Ascochyta spp, Aspergillus spp. including A. flavus, A. fumigatus, A. nidulans, A. niger, A. terrus, Aureobasidium spp. including A. pullulans, Blastomyces dermatitidis, Blumeria graminis, Bremia lactucae, Botryosphaeria spp. including B. dothidea, B. obtusa, Botrytis spp. including B. cinerea, Candida spp. including C. albicans, C. glabrata, C. krusei, C. lusitaniae, C. parapsilosis, C. tropicalis, Cephaloascus fragrans, Ceratocystis spp, Cercospora spp. including C. arachidicola, Cercosporidium personatum, Cladosporium spp, Claviceps purpurea, Coccidioides immitis, Cochliobolus spp, Colletotrichum spp. including C. musae, Cryptococcus neoformans, Diaporthe spp, Didymella spp, Drechslera spp, Elsinoe spp, Epidermophyton spp, Erwinia amylovora, Erysiphe spp. including E. cichoracearum, Eutypa lata, Fusarium spp. including F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium spp, Hemileia spp, Histoplasma spp. including H. capsulatum, Laetisaria fuciformis, Leptographium lindbergi, Leveillula taurica, Lophodermium seditiosum, Microdochium nivale, Microsporum spp, Monilinia spp, Mucor spp, Mycosphaerella spp. including M. graminicola, M. pomi, Oncobasidium theobromaeon, Ophiostoma piceae, Paracoccidioides spp, Penicillium spp. including P. digitatum, P. italicum, Petriellidium spp, Peronosclerospora spp. Including P. maydis, P. philippinensis and P. sorghi, Peronospora spp, Phaeosphaeria nodorum, Phakopsora pachyrhizi, Phellinus igniarus, Phialophora spp, Phoma spp, Phomopsis viticola, Phytophthora spp. including P. infestans, Plasmopara spp. including P. halstedii, P. viticola, Pleospora spp., Podosphaera spp. including P. leucotricha, Polymyxa graminis, Polymyxa betae, Pseudocercosporella herpotrichoides, Pseudomonas spp, Pseudoperonospora spp. including P. cubensis, P. humuli, Pseudopeziza tracheiphila, Puccinia Spp. including P. hordei, P. recondita, P. striiformis, P. triticina, Pyrenopeziza spp, Pyrenophora spp, Pyricularia spp. including P. oryzae, Pythium spp. including P. ultimum, Ramularia spp, Rhizoctonia spp, Rhizomucor pusillus, Rhizopus arrhizus, Rhynchosporium spp, Scedosporium spp. including S. apiospermum and S. prolificans, Schizothyrium pomi, Sclerotinia spp, Sclerotium spp, Septoria spp, including S. nodorum, S. tritici, Sphaerotheca macularis, Sphaerotheca fusca (Sphaerotheca fuliginea), Sporothorix spp, Stagonospora nodorum, Stemphylium spp., Stereum hirsutum, Thanatephorus cucumeris, Thielaviopsis basicola, Tilletia spp, Trichoderma spp. including T. harzianum, T. pseudokoningii, T. viride, Trichophyton spp, Typhula spp, Uncinula necator, Urocystis spp, Ustilago spp, Venturia spp. including V. inaequalis, Verticillium spp, and Xanthomonas spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins from Bacillus cereus or Bacillus popilliae; or insecticidal proteins from Bacillus thuringiensis, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus®

(maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50% to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuanryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N, -dimethyl-5-p-tolylimidazole-1-sulfonamide, N-allyl-4, 5,-dimethyl-2-trimethylsilylthiophene-3-carboxamide, N-(I-cyano-1,2-dimethylpropyl)-2-(2, 4-dichlorophenoxy) propionamide, N-(2-methoxy-5-pyridyl)-cyclopropane carboxamide, (.+-.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy) pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy) pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy) phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy) phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methyl-pyridin-2-yloxymethyl)phenyl]-3-methoxyacrylate, methyl (E)-2-[2-[6-(2- methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethyl pyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinylalcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenoquat, diflumetorim, O-di-iso-propyl-S-benzyl thiophosphate, difenzoquat, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino] thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, flutrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoximmethyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-AI, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

The following mixtures of the compounds of formula (I) with active ingredients are preferred. The abbreviation "TX" means one compound selected from the group consisting of the compounds described in: Tables 1.1 to 1.18 or Table T1 (below). an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime

[CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, *Bacillus subtilis* var. *amyloliquefaciens* Strain FZB24 (available from Novozymes Biologicals Inc., 5400 Corporate Circle, Salem, Va. 24153, U.S.A. and known under the trade name Taegro®)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name)

(421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, ometoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+

TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19-+ TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+ 187166-15-0]+TX, spirotetramat [203313-25-1]+TX, sulfoxaflor [946578-00-3]+TX, flufiprole [704886-18-0]+ TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of ametoctradin [865318-97-4]+TX, amisulbrom [348635-87-0]+TX, azaconazole [60207-31-0]+TX, benzovindiflupyr [1072957-71-1]+TX, bitertanol [70585-36-3]+TX, bixafen [581809-46-3]+TX, bromuconazole [116255-48-2]+TX, coumoxystrobin [850881-70-8]+TX, cyproconazole [94361-06-5]+TX, difenoconazole [119446-68-3]+TX, diniconazole [83657-24-3]+TX, enoxastrobin [238410-11-2]+TX, epoxiconazole [106325-08-0]+TX, fenbuconazole [114369-43-6]+TX, fenpyrazamine [473798-59-3]+TX, fluquinconazole [136426-54-5]+TX, flusilazole [85509-19-9]+TX, flutriafol [76674-21-0]+TX, fluxapyroxad [907204-31-3]+TX, fluopyram [658066-35-4]+TX, fenaminstrobin [366815-39-6]+TX, isofetamid [875915-78-9]+TX, hexaconazole [79983-71-4]+TX, imazalil [35554-44-0]+TX, imibenconazole [86598-92-7]+TX, ipconazole [125225-28-7]+TX, ipfentrifluconazole [1417782-08-1]+TX, isotianil [224049-04-1]+TX, mandestrobin [173662-97-0] (can be prepared according to the procedures described in WO 2010/093059)+TX, mefentrifluconazole [1417782-03-6]+TX, metconazole [125116-23-6]+TX, myclobutanil [88671-89-0]+TX, paclobutrazol [76738-62-0]+TX, pefurazoate [101903-30-4]+TX, penflufen [494793-67-8]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidin [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, fluindapyr [1383809-87-7]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, flutianil [958647-10-4]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, pyraoxystrobin [862588-11-2]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxinecopper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-

32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, picarbutrazox [500207-04-5]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyrametostrobin [915410-70-7]+TX, pyroquilon [57369-32-1]+TX, pyriofenone [688046-61-9]+TX, pyribencarb [799247-52-2]+TX, pyrisoxazole [847749-37-5]+TX, quinoxyfen [124495-18-7]+TX, quintozene [82-68-8]+TX, sulfur [7704-34-9]+TX, Timorex Gold™ (plant extract containing tea tree oil from the Stockton Group)+TX, tebufloquin [376645-78-2]+TX, tiadinil [223580-51-6]+TX, triazoxide [72459-58-6]+TX, tolprocarb [911499-62-2]+TX, triclopyricarb [902760-40-1]+TX, tricyclazole [41814-78-2]+TX, triforine [26644-46-2]+TX, validamycin [37248-47-8]+TX, valifenalate [283159-90-0]+TX, zoxamide (RH7281) [156052-68-5]+TX, mandipropamid [374726-62-2]+TX, isopyrazam [881685-58-1]+TX, phenamacril+TX, sedaxane [874967-67-6]+TX, trinexapac-ethyl [95266-40-3]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, or a biologically active compound selected from the group consisting of N-[(5-chloro-2-isopropyl-phenyl)methyl]-N-cyclopropyl-3-(difluoromethyl)-5-fluoro-1-methyl-pyrazole-4-carboxamide (can be prepared according to the procedures described in WO 2010/130767)+TX, 2,6-Dimethyl-1H,5H-[1,4]dithiino[2,3-c:5,6-c']dipyrrole-1,3,5,7(2H,6H)-tetrone (can be prepared according to the procedures described in WO 2011/138281)+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazazol-3-amine (can be prepared according to the procedures described in WO 2012/031061)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, CAS 850881-30-0+TX, 3-(3,4-dichloro-1,2-thiazol-5-ylmethoxy)-1,2-benzothiazole 1,1-dioxide (can be prepared according to the procedures described in WO 2007/129454)+TX, 2-[2-[(2,5-dimethylphenoxy) methyl]phenyl]-2-methoxy-N-methyl-acetamide+TX, 3-(4,4-difluoro-3,4-dihydro-3,3-dimethylisoquinolin-1-yl)quinolone (can be prepared according to the procedures described in WO 2005/070917)+TX, 2-[2-fluoro-6-[(8-fluoro-2-methyl-3-quinolyl)oxy]phenyl]propan-2-ol (can be prepared according to the procedures described in WO 2011/081174)+TX, 2-[2-[(7,8-difluoro-2-methyl-3-quinolyl)oxy]-6-fluoro-phenyl]propan-2-ol (can be prepared according to the procedures described in WO 2011/081174)+TX, oxathiapiprolin+TX [1003318-67-9], tert-butyl N-[6-[[[(1-methyltetrazol-5-yl)-phenyl-methylene] amino]oxymethyl]-2-pyridyl]carbamate+TX, N-[2-(3,4-difluorophenyl)phenyl]-3-(trifluoromethyl)pyrazine-2-carboxamide (can be prepared according to the procedures described in WO 2007/072999)+TX, 3-(difluoromethyl)-1-methyl-N-[(3R)-1,1,3-trimethylindan-4-yl]pyrazole-4-carboxamide (can be prepared according to the procedures described in WO 2014/013842)+TX, 2,2,2-trifluoroethyl N-[2-methyl-1-[[(4-methylbenzoyl)amino]methyl]propyl] carbamate+TX, (2RS)-2-[4-(4-chlorophenoxy)-α,α,α-trifluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3-ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine (can be prepared according to the procedures described in WO 2007/031513)+TX, [2-[3-[2-[1-[2-[3,5-bis(difluoromethyl) pyrazol-1-yl]acetyl]-4-piperidyl]thiazol-4-yl]-4,5-dihydroisoxazol-5-yl]-3-chloro-phenyl] methanesulfonate (can be prepared according to the procedures described in WO 2012/025557)+TX, but-3-ynyl N-[6-[[[(Z)-[(1-methyltetrazol-5-yl)-phenyl-methylene]amino]oxymethyl]-2-pyridyl] carbamate (can be prepared according to the procedures described in WO 2010/000841)+TX, 2-[[3-(2-chlorophenyl)-2-(2,4-difluorophenyl)oxiran-2-yl]methyl]-4H-1,2,4-triazole-3-thione (can be prepared according to the procedures described in WO 2010/146031)+TX, methyl N-[[5-[4-(2,4-dimethylphenyl)triazol-2-yl]-2-methyl-phenyl] methyl]carbamate+TX, 3-chloro-6-methyl-5-phenyl-4-(2,4,6-trifluorophenyl)pyridazine (can be prepared according to the procedures described in WO 2005/121104)+TX, 2-[2-chloro-4-(4-chlorophenoxy)phenyl]-1-(1,2,4-triazol-1-yl) propan-2-ol (can be prepared according to the procedures described in WO 2013/024082)+TX, 3-chloro-4-(2,6-difluorophenyl)-6-methyl-5-phenyl-pyridazine (can be prepared according to the procedures described in WO 2012/020774)+TX, 4-(2,6-difluorophenyl)-6-methyl-5-phenyl-pyridazine-3-carbonitrile (can be prepared according to the procedures described in WO 2012/020774)+TX, (R)-3-(difluoromethyl)-1-methyl-N-[1,1,3-trimethylindan-4-yl]pyrazole-4-carboxamide (can be prepared according to the procedures described in WO 2011/162397)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, 1-[2-[[1-(4-chlorophenyl)pyrazol-3-yl]oxymethyl]-3-methyl-phenyl]-4-methyl-tetrazol-5-one (can be prepared according to the procedures described in WO 2013/162072)+TX, 1-methyl-4-[3-methyl-2-[[2-methyl-4-(3,4,5-trimethylpyrazol-1-yl)phenoxy]methyl]phenyl]tetrazol-5-one (can be prepared according to the procedures described in WO 2014/051165)+TX, (Z,2E)-5-[1-(4-chlorophenyl) pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-(5-chloro-2- isopropylbenzyl)-N-cyclopropyl-3-(difluoromethyl)-5-fluoro-1-methylpyrazole-4-carboxamide [1255734-28-1] (can be prepared according to the procedures described in WO 2010/130767)+TX, 3-(difluoromethyl)-N-[(R)-2,3-dihydro-1,1,3-trimethyl-1H-inden-4-yl]-1-methylpyrazole-4-carboxamide [1352994-67-2]+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX,

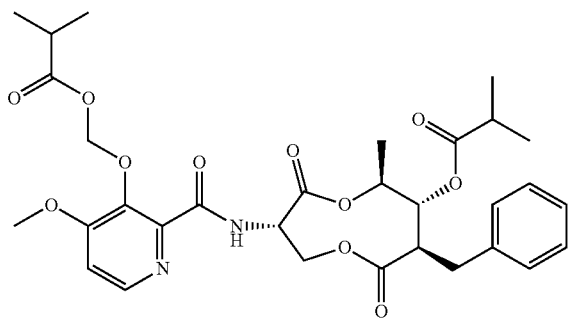 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(fenpicoxamid [517875-34-2])+TX (as described in WO 2003/035617), 2-(difluoromethyl)-N-(1,1,3-trimethylindan-4-yl)pyridine-3-carboxamide+TX, 2-(difluoromethyl)-N-(3-ethyl-1,1-dimethyl-indan-4-yl)pyridine-3-carboxamide+TX, 2-(difluoromethyl)-N-(1,1-dimethyl-3-propyl-indan-4-yl)pyridine-3-carboxamide+TX, 2-(difluoromethyl)-N-(3-isobutyl-1,1-dimethyl-indan-4-yl)pyridine-3-carboxamide+TX, 2-(difluoromethyl)-N-[(3R)-1,1,3-trimethylindan-4-yl]pyridine-3-carboxamide+TX, 2-(difluoromethyl)-N-[(3R)-3-ethyl-1,1-dimethyl-indan-4-yl]pyridine-3-carboxamide+TX, and 2-(difluoromethyl)-N-[(3R)-1,1-dimethyl-3-propyl-indan-4-yl]pyridine-3-carboxamide+TX, wherein each of these carboxamide compounds can be prepared according to the procedures described in WO 2014/095675 and/or WO 2016/139189.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from a compound 1.1 to 1.171 described in Table T1 (below) or a compound of formula (I) described in Tables 1.1 to 1.18 (below), and an active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from one of Tables 1.1 to 1.18 (below), or Table T1 (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Tables 1.1 to 1.18 (below), or Table T1 (below), and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds of formula (I) for the preparation of these compositions are also a subject of the invention.

Another aspect of the invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of the invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 g to 50 g of a compound of formula I per kg of seed, preferably from 0.01 g to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

TABLE 1.1

This table discloses 44 specific compounds of the formula (T-1):

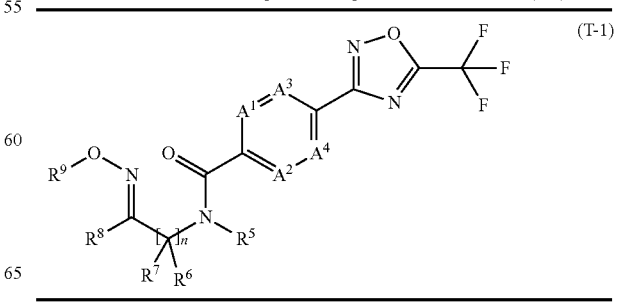

wherein n is 1, $A^1$ is $C-R^1$, $A^2$ is $C-R^2$, $A^3$ is $C-R^3$, $A^4$ is $C-R^4$ and $R^1$, $R^2$, $R^3$, $R^4$, $R^5$, $R^6$, $R^7$ and $R^8$ are hydrogen, and $R^9$ is as defined below in Table 1.

Each of Tables 1.2 to 1.18 (which follow Table 1.1) make available 44 individual compounds of the formula (T-1) in which n, $A^1$, $A^2$, $A^3$, $A^4$, $R^1$, $R^2$, $R^3$, $R^4$, $R^5$, $R^6$, $R^7$ and $R^8$ are as specifically defined in Tables 1.2 to 1.18, which refer to Table 1 wherein $R^9$ is specifically defined.

TABLE 1

| Compound no. | $R^9$ |
|---|---|
| 1.001 | (tetrahydropyran-2-yl) |
| 1.002 | —CH₂CH₃ |
| 1.003 | —(CH₂)₁₁CH₃ |
| 1.004 | (2,6-dichlorophenyl-methyl) |
| 1.005 | (benzyl) |
| 1.006 | (2-chlorobenzyl) |
| 1.007 | (4-methoxybenzyl) |
| 1.008 | —CH₂CH=CHCl |
| 1.009 | (3-methoxybenzyl) |
| 1.010 | (2-(methoxycarbonylmethyl)benzyl) |
| 1.011 | —CH₂CH=CH₂ |
| 1.012 | —CH₂CH=C(CH₃)₂ |
| 1.013 | —CH₂CH=C(Cl)₂ |
| 1.014 | —CH(CH₃)₂ |
| 1.015 | —CH(CH₃)C(O)OCH₂CH₃ ((R) and (S)) |

TABLE 1-continued

| Compound no. | $R^9$ |
|---|---|
| 1.016 | —CH₂CH(CH₃)₂ |
| 1.017 | (4-chlorobenzyl) |
| 1.018 | —CH₃ |
| 1.019 | (phenyl) |
| 1.020 | —C(CH₃)₃ |
| 1.021 | (pentafluorobenzyl) |
| 1.022 | (4-nitrobenzyl) |
| 1.023 | (2,4,5-trichlorobenzyl) |
| 1.024 | —(CH₂)₅CH₃ |
| 1.025 | —CH₂CH=CHCl ((E) and (Z)) |
| 1.026 | —CH₂CH₂CH₂CH₃ |
| 1.027 | —CH₂CH₂OH |
| 1.028 | —CH₂C(=CH₂)Cl |
| 1.029 | (4-fluorobenzyl) |
| 1.030 | (4-bromobenzyl) |
| 1.031 | —CH₂CH₂CH₃ |
| 1.032 | (4-methylbenzyl) |
| 1.033 | (3-chlorobenzyl) |

TABLE 1-continued

| Compound no. | R⁹ |
|---|---|
| 1.034 | 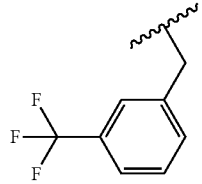 [SMILES: *Cc1cccc(C(F)(F)F)c1] |
| 1.035 |  |
| 1.036 | —CH(CH$_3$)C(O)OH |
| 1.037 | 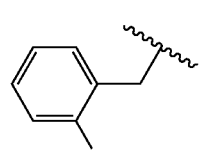 |
| 1.038 | 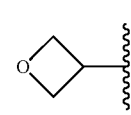 [SMILES: *C1COC1] |
| 1.039 | 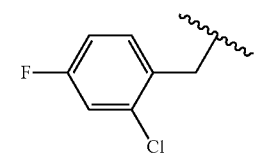 |
| 1.040 | —CH$_2$C≡CH |
| 1.041 | —CH$_2$CF$_3$ |
| 1.042 | 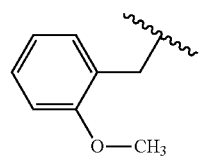 |
| 1.043 | 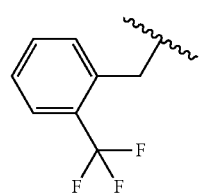 [SMILES: *Cc1ccccc1C(F)(F)F] |
| 1.044 | H |

Table 1.2:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, $R^6$, $R^7$ and $R^8$ are hydrogen, $R^1$ is fluorine, and $R^9$ is as defined above in Table 1.

Table 1.3:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^4$, $R^5$, $R^6$, $R^7$ and $R^8$ are hydrogen, $R^3$ is fluorine, and $R^9$ is as defined above in Table 1.

Table 1.4:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^4$, $R^5$, $R^6$, $R^7$ and $R^8$ are hydrogen, $R^1$ and $R^3$ are fluorine, and $R^9$ is as defined above in Table 1.

Table 1.5:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^3$, $R^4$, $R^5$, $R^6$, $R^7$ and $R^8$ are hydrogen, $R^1$ and $R^2$ are fluorine, and $R^9$ is as defined above in Table 1.

Table 1.6:
This table discloses 44 specific compounds of formula (T-1) wherein n is 2, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$, $R^7$ and $R^8$ are hydrogen, and $R^9$ is as defined above in Table 1.

Table 1.7:
This table discloses 44 specific compounds of formula (T-1) wherein n is 2, $A^1$ is C—$R^1$, $A^2$ is C—$R^2$, $A^3$ is C—$R^3$, $A^4$ is C—$R^4$ and $R^2$, $R^3$, $R^4$, $R^5$, $R^6$, $R^7$ and $R^8$ are hydrogen, $R^1$ is fluorine, and $R^9$ is as defined above in Table 1.

Table 1.8:
This table discloses 44 specific compounds of formula (T-1) wherein n is 2, $A^1$ is C—$R^1$, $A^2$ is C—$R^2$, $A^3$ is C—$R^3$, $A^4$ is C—$R^4$ and $R^1$, $R^2$, $R^4$, $R^5$, $R^6$, $R^7$ and $R^8$ are hydrogen, $R^3$ is fluorine, and $R^9$ is as defined above in Table 1.

Table 1.9:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^7$ and $R^8$ are hydrogen, $R^6$ is methyl, and $R^9$ is as defined below in Table 1.

Table 1.10:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, $R^7$ and $R^8$ are hydrogen, $R^1$ is fluorine, $R^6$ is methyl, and $R^9$ is as defined above in Table 1.

Table 1.11:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^4$, $R^5$, $R^7$ and $R^8$ are hydrogen, $R^3$ is fluorine, $R^6$ is methyl, and $R^9$ is as defined above in Table 1.

Table 1.12:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, $R^6$ and $R^7$ are hydrogen, $R^8$ is methyl, and $R^9$ is as defined above in Table 1.

Table 1.13:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^2$, $R^3$, $R^4$, $R^5$, $R^6$ and $R^7$ are hydrogen, $R^1$ is fluorine, $R^8$ is methyl, and $R^9$ is as defined above in Table 1.

Table 1.14:
This table discloses 44 specific compounds of formula (T-1) wherein n is 1, $A^1$ is C—$R^1$, $A^2$ is C—$R^2$, $A^3$ is C—$R^3$, $A^4$ is C—$R^4$ and $R^1$, $R^2$, $R^4$, $R^5$, $R^6$ and $R^7$ are hydrogen, $R^3$ is fluorine, $R^8$ is methyl, and $R^9$ is as defined above in Table 1.

Table 1.15:
This table discloses 44 specific compounds of formula (T-1) wherein n is 0, $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$ and $R^8$ are hydrogen, and $R^9$ is as defined above in Table 1.

Table 1.16:
This table discloses 44 specific compounds of formula (T-1) wherein n is 0, $A^1$ is C—$R^1$, $A^2$ is C—$R^2$, $A^3$ is C—$R^3$, $A^4$ is C—$R^4$ and $R^2$, $R^3$, $R^4$, $R^5$ and $R^8$ are hydrogen, $R^1$ is fluorine, and $R^9$ is as defined above in Table 1.

Table 1.17:

This table discloses 44 specific compounds of formula (T-1) wherein n is 0, $A^1$ is C—$R^1$, $A^2$ is C—$R^2$, $A^3$ is C—$R^3$, $A^4$ is C—$R^4$ and $R^1$, $R^2$, $R^4$, $R^5$ and $R^8$ are hydrogen, $R^3$ is fluorine, and $R^9$ is as defined above in Table 1.

Table 1.18:

This table discloses 44 specific compounds of formula (T-1) wherein n is 0, $A^1$ is C—$R^1$, $A^2$ is C—$R^2$, $A^3$ is C—$R^3$, $A^4$ is C—$R^4$ and $R^1$, $R^2$, $R^3$, $R^4$, and $R^5$ are hydrogen, $R^8$ is methyl, and $R^9$ is as defined above in Table 1.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm, or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, LC/MS means Liquid Chromatography Mass Spectrometry and the description of the apparatus and the method (Methods A, B, C and D) is as follows:

The Description of the Apparatus and the Method A is:
SQ Detector 2 from Waters
Ionisation method: Electrospray
Polarity: positive and negative ions
Capillary (kV) 3.0, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650
Mass range: 100 to 900 Da
DAD Wavelength range (nm): 210 to 500
Method Waters ACQUITY UPLC with the Following HPLC Gradient Conditions
(Solvent A: Water/Methanol 20:1+0.05% formic acid and Solvent B: Acetonitrile+0.05% formic acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.
The Description of the Apparatus and the Method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the Following HPLC Gradient Conditions
(Solvent A: Water/Methanol 9:1+0.1% formic acid and Solvent B: Acetonitrile+0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
The Description of the Apparatus and the Method C is:
6410 Triple quadrupole Mass Spectrometer from Agilent Technologies
Agilent 1200 Series HPLC
Ionisation method: Electrospray
Polarity: positive and negative polarity switch
Capillary (kV) 4.0, Cone (V) 100, Extractor (V) 4.00, Desolvation Temperature (° C.) 300, Cone Gas Flow (psi) 45, Desolvation Gas Flow (L/min.) 11
Mass range: 140 to 800 Da
DAD Wavelength range (nm): 210 to 400
HPLC Gradient Conditions
(Solvent A: Water, 0.1% formic acid and Solvent B: Acetonitrile, 0.1% formic acid)

| Time (minutes) | A (%) | B (%) | Flow rate (ml/min) |
|---|---|---|---|
| 0 | 90 | 10 | 1.8 |
| 0.9 | 0 | 100 | 1.80 |
| 1.8 | 0 | 100 | 1.80 |
| 2.2 | 90 | 10 | 1.80 |

Type of column: KINETEX EVO C18; Column length: 50 mm; Internal diameter of column: 4.6 mm; Particle Size: 2.6μ; Temperature: 40° C.
The Description of the Apparatus and the Method D is:
Mass Spectrometer: ACQUITY SQD Mass Spectrometer from Waters
Ionisation method: Electrospray
Polarity: Positive and Negative Polarity Switch
Capillary (kV): 3.0, Cone Voltage (V): 41, Source Temperature (° C.) 150,
Desolvation Gas Flow (L/Hr) 1000, Desolvation Temperature (° C.500, Gas Flow @ Cone (L/Hr)50, Mass range1 110 to 800 Da, PDA Wavelength range (nm) 210 to 400
Gradient Conditions:
Solvent A: Water with 0.1% formic acid:Acetonitrile 95:5 v/v
Solvent B: Acetonitrile with 0.05% formic acid

| Time (minutes) | A (%) | B (%) | Flow rate (ml/min) |
|---|---|---|---|
| 0 | 90 | 10 | 0.8 |
| 0.2 | 50 | 50 | 0.8 |
| 0.7 | 0 | 100 | 0.8 |
| 1.3 | 0 | 100 | 0.8 |
| 1.4 | 90 | 10 | 0.8 |
| 1.6 | 90 | 10 | 0.8 |

Type of column: Waters ACQUITY UPLC HSS T3 C18; Column length: 30 mm; Internal diameter of column: 2.1 mm; Particle Size: 1.8μ; Temperature: 40° C.

Where necessary, enantiomerically pure final compounds may be obtained from racemic materials as appropriate via standard physical separation techniques, such as reverse phase chiral chromatography, or through stereoselective synthetic techniques, e.g., by using chiral starting materials.

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

LIST OF ABBREVIATIONS

CDCl₃=chloroform-d
° C.=degrees Celsius
d=doublet
EtOAc=ethyl acetate
h=hour(s)
HCl=hydrochloric acid
M=molar
min=minutes
MHz=mega hertz
mp=melting point
m=multiplet
M=molar
N=normal
ppm=parts per million
RT=room temperature
R$_t$=retention time
s=singlet
t=triplet
TFAA=trifluoroacetic acid anhydride
LC/MS=Liquid Chromatography Mass Spectrometry (description of the apparatus and the methods used for LC/MS analysis are given above)

PREPARATION EXAMPLES

Example 1: Preparation of 2-fluoro-N-(2-methoxy-imino-1,1-dimethyl-ethyl)-4-[5-(trifluoromethyl)-1,2,4-oxadiazol-3-yl]benzamide (Compound 1.2 of Table T1)

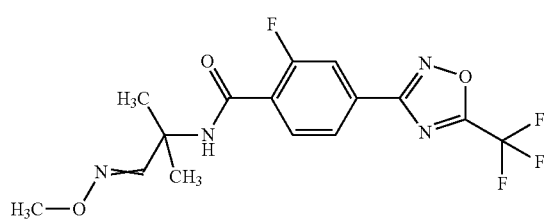 [SMILES: CON=CC(C)(C)NC(=O)c1ccc(-c2noc(C(F)(F)F)n2)cc1F]

To a stirring solution of 1-methoxyimino-2-methyl-propan-2-amine hydrochloride (0.070 g, 0.46 mmol) in dichloromethane (11.0 mL) under an atmosphere of nitrogen was added triethylamine (0.25 mL, 1.77 mmol) at room temperature, followed by the addition of 2-fluoro-4-[5-(trifluoromethyl)-1,2,4-oxadiazol-3-yl]benzoyl chloride (0.13 g, 0.44 mmol). The reaction mixture was allowed to react for 18 hours at room temperature. The solvent was removed under reduced pressure and the resultant crude residue was subjected to flash chromatography over silica gel (heptane: ethyl acetate (EtOAc) eluent 99:1 to 1:99) to afford 0.093 g of 2-fluoro-N-(2-methoxyimino-1,1-dimethyl-ethyl)-4-[5-(trifluoromethyl)-1,2,4-oxadiazol-3-yl]benzamide as an oil. LC-MS method A [1.11 min.; 375 (M+H)].

¹H NMR (400 MHz, CDCl₃) δ ppm: 8.26 (m, 1H), 8.04 (m, 1H), 7.92 (d, 1H), 7.71 (d, 1H), 4.51 (s, 1H), 3.91 (s, 3H), 1.68 (s, 6H).

Example 2: Preparation of N-(2-methoxyimino-1-methyl-ethyl)-4-[5-(trifluoromethyl)-1,2,4-oxadiazol-3-yl] benzamide (Compound 1.3 of Table T1)

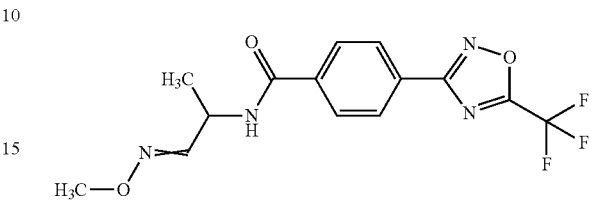

Step 1: Preparation of N-(2-hydroxy-1-methyl-ethyl)-4-[5-(trifluoromethyl)-1,2,4-oxadiazol-3-yl] benzamide

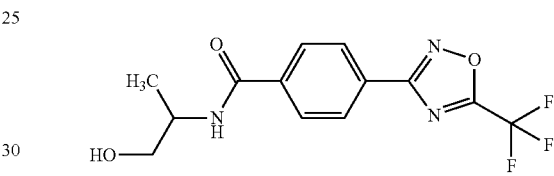

To a stirring solution of 2-aminopropan-1-ol (0.95 g, 13.0 mmol) in dichloromethane (25.0 mL) under an atmosphere of nitrogen was added triethylamine (1.50 g, 15.0 mmol) at room temperature, followed by the addition of 4-[5-(trifluoromethyl)-1,2,4-oxadiazol-3-yl] benzoyl chloride (3.70 g, 9.8 mmol) in dichloromethane (5.0 mL). The reaction mixture was allowed to react for 18 hours at room temperature. The solvent was removed under reduced pressure and the resultant crude residue was subjected to flash chromatography over silica gel (dichloromethane: EtOAc eluent 1:3) to afford 1.61 g of N-(2-hydroxy-1-methyl-ethyl)-4-[5-(trifluoromethyl)-1,2,4-oxadiazol-3-yl] benzamide as a white solid (melting point: 168-169° C.).

Step 2: Preparation of N-(1-methyl-2-oxo-ethyl)-4-[5-(trifluoromethyl)-1,2,4-oxadiazol-3-yl]benzamide

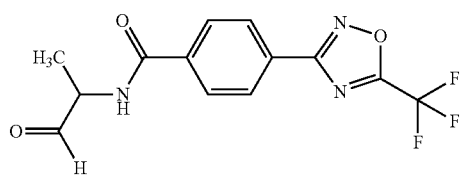 [SMILES: CC(C=O)NC(=O)c1ccc(-c2noc(C(F)(F)F)n2)cc1]

To a stirring solution of N-(2-hydroxy-1-methyl-ethyl)-4-[5-(trifluoromethyl)-1,2,4-oxadiazol-3-yl] benzamide (0.10 g, 0.32 mmol) in dichloromethane (4.0 mL) under an atmosphere of nitrogen was added trichloroisocyanuric acid (0.08 g, 3.3 mmol) at 5° C. followed by addition of 1-piperidinyloxy-2,2,6,6-tetramethyl (0.05 mg, 0.003 mmol). The reaction mixture was allowed to react for 15 minutes at 5° C., then filtered over silica gel and evaporated the solvent to afford 0.089 g of N-(1-methyl-2-oxo-ethyl)-4-[5-(trifluoromethyl)-1,2,4-oxadiazol-3-yl] benzamide as a gum.

$^1$H NMR (400 MHz, CDCl$_3$) δ ppm: 9.70 (s, 1H), 8.24 (d, 2H), 7.81 (d, 2H), 6.95 (m, 1H), 4.75 (m, 1H), 1.53 (d, 3H).

Step 3: Preparation of N-(2-methoxyimino-1-methyl-ethyl)-4-[5-(trifluoromethyl)-1,2,4-oxadiazol-3-yl] benzamide To a stirring solution of N-(1-methyl-2-oxo-ethyl)-4-[5-(trifluoromethyl)-1,2,4-oxadiazol-3-yl] benzamide (0.10 g, 0.31 mmol) in dichloromethane (6.0 mL) under an atmosphere of nitrogen was added O-methylhydroxylamine chloride (0.03 g, 0.30 mmol) followed by triethylamine (0.07 mL, 0.48 mmol) at room temperature. The reaction mixture was allowed to react for 16 hours at room temperature. The reaction mixture was washed with saturated aqueous sodium bicarbonate solution, 1N HCl and water. The organic layer was dried over sodium sulfate, and filtered. The solvent was removed under reduced pressure and the resultant crude residue was subjected to flash chromatography over silica gel (heptane:ethyl acetate eluent 99:1 to 1:99) to afford the desired N-(2-methoxyimino-1-methyl-ethyl)-4-[5-(trifluoromethyl)-1,2,4-oxadiazol-3-yl]benzamide as an oil.

$^1$H NMR (400 MHz, CDCl$_3$) δ ppm: 8.24 (d, 2H), 7.76 (d, 2H), 7.51 (m, 1H), 6.85 (d, 1H), 4.88 (m, 1H), 3.89 (s, 3H), 1.48 (d, 3H).

Example 3a: Preparation of (Z)-N-(methoxyiminomethyl)-4-[5-(trifluoromethyl)-1,2,4-oxadiazol-3-yl] benzamide (Compound 1.5 of Table T1)

Example 3b: Preparation of (E)-N-(methoxyiminomethyl)-4-[5-(trifluoromethyl)-1,2,4-oxadiazol-3-yl] benzamide

Step 1: Preparation N-(dimethylaminomethylene)-4-[5-(trifluoromethyl)-1,2,4-oxadiazol-3-yl]benzamide

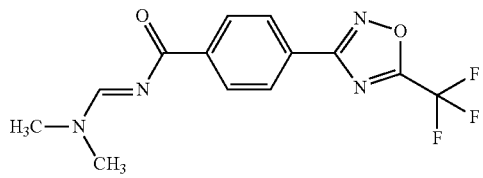 [SMILES: CN(C)/C=N/C(=O)c1ccc(-c2noc(C(F)(F)F)n2)cc1]

To a stirring suspension of 4-[5-(trifluoromethyl)-1,2,4-oxadiazol-3-yl] benzamide (1.00 g, 3.89 mmol) in toluene (6.2 mL) under an atmosphere of nitrogen was added dimethylformamide dimethylacetate (0.72 g, 5.84 mmol) at room temperature. The reaction mixture was allowed to react for 16 hours at 90° C. whilst the methanol by-product was distilled off. The solvent was removed under reduced pressure to afford crude N-(dimethylaminomethylene)-4-[5-(trifluoromethyl)-1,2,4-oxadiazol-3-yl]benzamide as a beige solid (melting point: 127-132° C.).

$^1$H NMR (400 MHz, CDCl$_3$) δ ppm: 8.69 (s, 1H), 8.42 (d, 2H), 8.18 (d, 2H), 3.23 (s, 3H), 3.27 (s, 3H).

Step 2: Preparation N-(methoxyiminomethyl)-4-[5-(trifluoromethyl)-1,2,4-oxadiazol-3-yl]benzamide

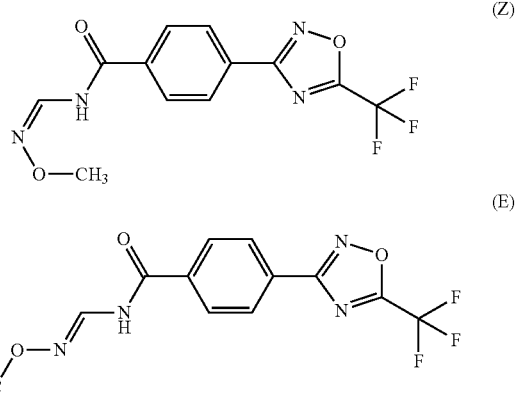

To a stirring suspension of O-methylhydroxylamine chloride (0.35 g, 4.20 mmol) in dichloromethane (4.0 mL) under an atmosphere of nitrogen was added triethylamine (0.43 g, 4.20 mmol) at room temperature. After 5 minutes crude N-(dimethylaminomethylene)-4-[5-(trifluoromethyl)-1,2,4-oxadiazol-3-yl] benzamide (1.3 g, 4.2 mmol) was added. The reaction mixture was allowed to react for 16 hours at room temperature. The crude was washed with 1N NaOH and dried over sodium sulfate. The solvent was removed under reduced pressure. The crude residue was subjected to flash chromatography over silica gel (dichloromethane:diisopropyl ether eluent 1:99) to afford an E/Z-mixture of N-(methoxyiminomethyl)-4-[5-(trifluoromethyl)-1,2,4-oxadiazol-3-yl] benzamide.

(Z)-N-(methoxyiminomethyl)-4-[5-(trifluoromethyl)-1,2,4-oxadiazol-3-yl] benzamide (melting point: 135-140° C.)—$^1$H NMR (400 MHz, CDCl$_3$) δ ppm: 8.90 (d, 1H), 8.28 (d, 2H), 8.03 (d, 2H), 7.83 (d, 1H), 3.96 (s, 3H).

(E)-N-(methoxyiminomethyl)-4-[5-(trifluoromethyl)-1,2,4-oxadiazol-3-yl] benzamide—$^1$H NMR (400 MHz, CDCl$_3$) δ ppm: 8.64 (d, 1H), 8.28 (d, 2H), 7.99 (d, 2H), 7.83 (d, 1H), 3.81 (s, 3H).

Example 4a: Preparation of N-[(Z)-prop-2-ynoxyiminomethyl)-4-[5-(trifluoromethyl)-1,2,4-oxadiazol-3-yl] benzamide (Compound 1.6 of Table T1)

Example 4b: Preparation of N-[(E)-prop-2-ynoxyiminomethyl)-4-[5-(trifluoromethyl)-1,2,4-oxadiazol-3-yl] benzamide

Step 2: Preparation N-[(Z)-prop-2-ynoxyiminomethyl)-4-[5-(trifluoromethyl)-1,2,4-oxadiazol-3-yl] benzamide

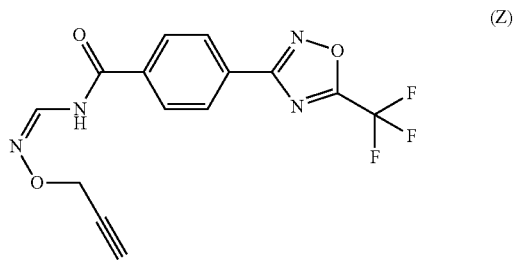

-continued

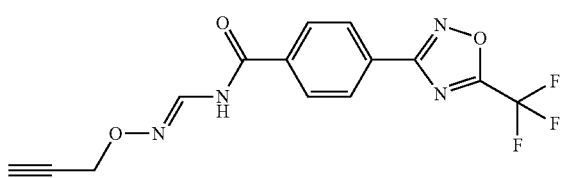

(E)

To a stirring suspension of O-propynylhydroxylamine chloride (0.22 g, 1.92 mmol) in dichloromethane (4.0 mL) under an atmosphere of nitrogen was added triethylamine (0.27 mL, 1.92 mmol) at room temperature. After 5 minutes crude N-(dimethylaminomethylene)-4-[5-(trifluoromethyl)-1,2,4-oxadiazol-3-yl] benzamide (0.6 g, 1.92 mmol) was added. The reaction mixture was allowed to react for 16 hours at room temperature. The organic phase was washed with 1N NaOH (3.5 mL) and dried over sodium sulfate. The solvent was removed under reduced pressure. The crude residue was subjected to flash chromatography over silica gel (dichloromethane:diisopropyl ether eluent 1:99) to afford a 4:1 E/Z-mixture of N-[(E/Z)-prop-2-ynoxyiminomethyl]-4-[5-(trifluoromethyl)-1,2,4-oxadiazol-3-yl] benzamide.

N-[(Z)-prop-2-ynoxyiminomethyl]-4-[5-(trifluoromethyl)-1,2,4-oxadiazol-3-yl] benzamide (melting point: 114-119° C.)—$^1$H NMR (400 MHz, CDCl$_3$) δ ppm: 8.89 (d, 1H), 8.27 (d, 2H), 8.02 (d, 2H), 7.93 (d, 1H), 4.73 (d, 2H), 2.53 (t, 1H).

N-[(E)-prop-2-ynoxyiminomethyl]-4-[5-(trifluoromethyl)-1,2,4-oxadiazol-3-yl] benzamide—$^1$H NMR (400 MHz, CDCl$_3$) δ ppm: 8.71 (d, 1H), 8.25 (d, 2H), 8.01 (d, 2H), 7.93 (d, 1H), 4.60 (d, 2H), 2.51 (t, 1H).

Example 5: Preparation of N-[3-ethoxyiminopropyl]-4-[5-(trifluoromethyl)-1,2,4-oxadiazol-3-yl]benzamide (Compound 1.153 of Table T1)

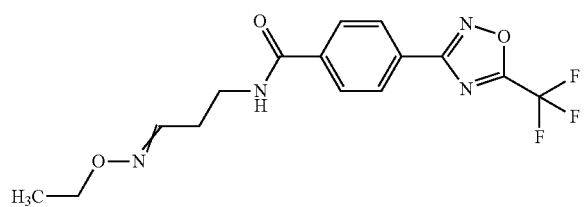 [SMILES: CCON=CCCNC(=O)c1ccc(-c2noc(C(F)(F)F)n2)cc1]

Step 1: Preparation of N-(3-hydroxypropyl)-4-[5-(trifluoromethyl)-1,2,4-oxadiazol-3-yl]benzamide

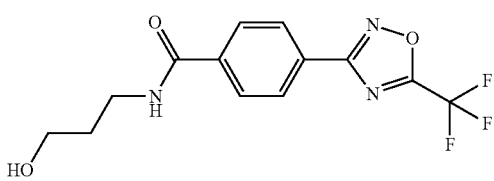 [SMILES: O=C(NCCCO)c1ccc(-c2noc(C(F)(F)F)n2)cc1]

To a solution of 4-[5-(trifluoromethyl)-1,2,4-oxadiazol-3-yl]benzoic acid (2.5 g, 9.7 mmol) in dichloromethane (29 mL) was added at ambient temperature, N-(3-dimethylaminopropyl)-N'-ethylcarbodiimide hydrochloride (2.8 g, 15 mmol) followed by trimethylamine (4 mL, 29.1 mmol), 1-hydroxybenzotriazole hydrate (0.74 g, 4.8 mmol) and 3-amino-1-propanol (0.88 g, 12 mmol). After stirring overnight at ambient temperature for 24 hours, water (25 mL) was added and the organics were extracted using dichloromethane. The solvent was removed under reduced pressure to afford the title compound (2.3 g, 75% of theoretical yield) as pale yellow solid. LC/MS (Method C) retention time (R$_t$)=1.33 minutes, 316 (M+H).

Step 2: Preparation of N-(3-oxopropyl)-4-[5-(trifluoromethyl)-1,2,4-oxadiazol-3-yl]benzamide

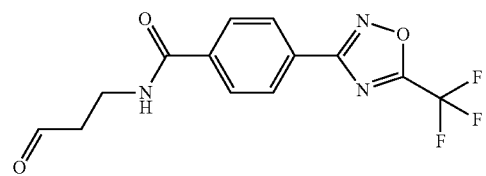 [SMILES: O=CCCNC(=O)c1ccc(-c2noc(C(F)(F)F)n2)cc1]

To a solution of N-(3-hydroxypropyl)-4-[5-(trifluoromethyl)-1,2,4-oxadiazol-3-yl]benzamide (0.60 g, 1.90 mmol) in chloroform (5.712 mL) was added at 0° C., Dess-Martin Periodinane (1.22 g, 2.86 mmol). After stirring overnight at ambient temperature, saturated sodium thiosulfate (15 mL) was added and the organics were extracted using dichloromethane. The solvent was removed under reduced pressure and the resultant crude material was purified by flash chromatography over silica gel (cyclohexane:EtOAc eluent gradient 1:0 to 1:1) to afford the title compound as a white solid. LC/MS (Method C) retention time (R$_t$)=1.36 minutes, 313.9 (M+H).

Step 3: Preparation of N-[3-ethoxyiminopropyl]-4-[5-(trifluoromethyl)-1,2,4-oxadiazol-3-yl]benzamide

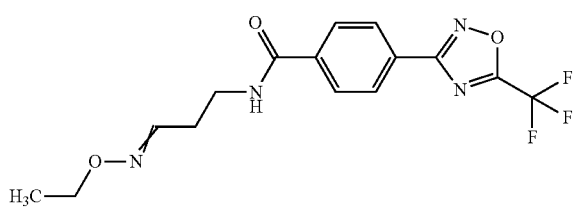 [SMILES: CCON=CCCNC(=O)c1ccc(-c2noc(C(F)(F)F)n2)cc1]

To a solution of N-(3-oxopropyl)-4-[5-(trifluoromethyl)-1,2,4-oxadiazol-3-yl]benzamide (150 mg, 0.479 mmol) in ethanol (1.44 mL) was added at room temperature ethoxylamine hydrochloride (140.1 mg 1.44 mmol) and sodiumacetate (117.9 mg, 1.44 mmol). The reaction mixture was heated at 80° C. for 16 hours. The mixture was cooled to room temperature, filtered and the filtrate was evaporated under reduced pressure to obtain crude material. The resultant crude material was purified by flash chromatography over silica gel (cyclohexane:EtOAc eluent gradient 1:0 to 1:0.5) to afford the title compound as white solid. LC/MS (Method C) retention time (R$_t$)=1.53 minutes, 370.9 (M+H).

Example 6: Preparation of 2-fluoro-N-[2-methoxy-iminopropyl]-4-[5-(trifluoromethyl)-1,2,4-oxadiazol-3-yl]benzamide (Compound 1.157 of Table T1)

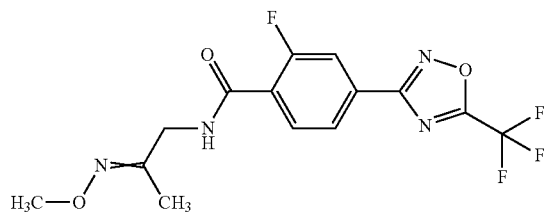 [SMILES: CON=C(C)CNC(=O)c1ccc(-c2noc(C(F)(F)F)n2)cc1F]

Step 1: Preparation of 2-fluoro-N-(2-hydroxypropyl)-4-[5-(trifluoromethyl)-1,2,4-oxadiazol-3-yl]benzamide

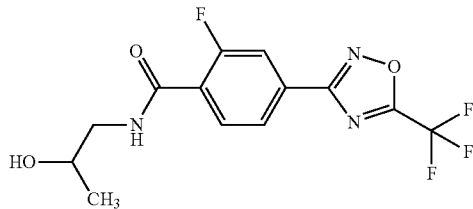 [SMILES: CC(O)CNC(=O)c1ccc(-c2noc(C(F)(F)F)n2)cc1F]

To a solution of 2-fluoro-4-[5-(trifluoromethyl)-1,2,4-oxadiazol-3-yl]benzoic acid (0.600 g, 2.173 mmol) in dichloromethane (6.51 mL) was added at ambient temperature, N-(3-dimethylaminopropyl)-N'-ethylcarbodiimide hydrochloride (0.638 g, 3.26 mmol) followed by trimethylamine (0.91 mL, 6.52 mmol), 1-hydroxybenzotriazole hydrate (0.166 g, 1.09 mmol) and 1-aminopropan-2-ol (0.196 g 2.61 mmol). After stirring at ambient temperature for 24 hours, water (25 mL) was added and the organics were extracted using dichloromethane. The solvent was removed under reduced pressure to give crude material. The resultant crude material was purified by flash chromatography over silica gel (cyclohexane:EtOAc eluent gradient 1:0 to 1:1) to afford the title compound as a white solid. LC/MS (Method C) retention time ($R_t$)=1.08 minutes, 333.8 (M+H).

Step 2: Preparation of N-acetonyl-2-fluoro-4-[5-(trifluoromethyl)-1,2,4-oxadiazol-3-yl]benzamide

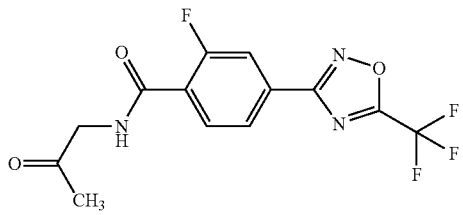 [SMILES: CC(=O)CNC(=O)c1ccc(-c2noc(C(F)(F)F)n2)cc1F]

To a solution of 2-fluoro-N-(2-hydroxypropyl)-4-[5-(trifluoromethyl)-1,2,4-oxadiazol-3-yl]benzamide (0.460 g, 1.38 mmol) in chloroform (4.14 mL) was added at 0° C., Dess-Martin Periodinane (0.887 g, 2.07 mmol). After stirring overnight at ambient temperature, saturated sodium thiosulfate (15 mL) was added and the organics were extracted using dichloromethane. The solvent was removed under reduced pressure and the resultant crude material was purified by flash chromatography over silica gel (cyclohexane:EtOAc eluent gradient 1:0 to 1:1) to afford the title compound as white a solid. LC/MS (Method C) retention time ($R_t$)=1.54 minutes, 332 (M+H).

Step 3: Preparation of N-[3-ethoxyiminopropyl]-4-[5-(trifluoromethyl)-1,2,4-oxadiazol-3-yl]benzamide

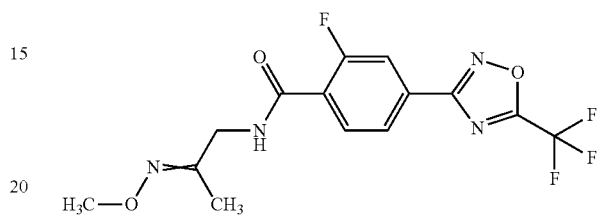

To a solution of N-acetonyl-2-fluoro-4-[5-(trifluoromethyl)-1,2,4-oxadiazol-3-yl]benzamide (120 mg, 0.362 mmol) in ethanol (1.1 mL) was added at room temperature methoxylamine hydrochloride (93 mg 1.08 mmol) and sodium acetate (89.1 mg, 1.09 mmol). The reaction mixture was heated at 80° C. for 16 hours. The mixture was cooled to room temperature, filtered and the filtrate was evaporated under reduced pressure to obtain crude material. The resultant crude material was purified by flash chromatography over silica gel (cyclohexane/EtOAc eluent gradient 1:0 to 1:0.5) to afford the title compound as a white solid. LC/MS (Method C) retention time ($R_t$)=1.89 minutes, 361.1 (M+H).

Example 7: Preparation of N-[3-ethoxyiminopropyl]-3-fluoro-4-[5-(trifluoromethyl)-1,2,4-oxadiazol-3-yl]benzamide (Compound 1.161 of Table T1)

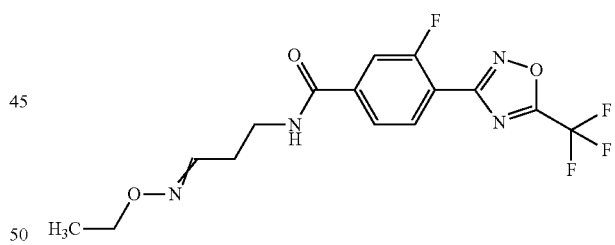

Step 1: Preparation of 3-fluoro-N-(3-hydroxypropyl)-4-[5-(trifluoromethyl)-1,2,4-oxadiazol-3-yl]benzamide

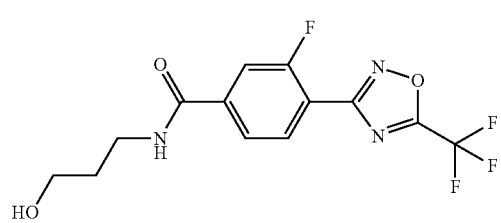 [SMILES: O=C(NCCCO)c1ccc(-c2noc(C(F)(F)F)n2)c(F)c1]

To a solution of 3-fluoro-4-[5-(trifluoromethyl)-1,2,4-oxadiazol-3-yl]benzoic acid (700 mg, 2.535 mmol) in dichloromethane (7.6 mL) was added at ambient temperature, N-(3-dimethylaminopropyl)-N'-ethylcarbodiimide hydrochloride (743.8 mg, 3.802 mmol) followed by triethylamine (1.07 mL, 7.605 mmol), 1-hydroxybenzotriazole hydrate (194.1 mg, 1.268 mmol) and 3-amino-1-propanol (230.8 mg 3.042 mmol). After stirring at ambient temperature for 24 hours, water (25 mL) was added and the organics were extracted using dichloromethane. The solvent was removed under reduced pressure to give crude material. The resultant crude material was purified by flash chromatography over silica gel (cyclohexane:EtOAc eluent gradient 1:0 to 1:1) to afford the title compound as a white solid. LC/MS (Method D) retention time ($R_t$)=0.79 minutes, 334.25 (M+H).

Step 2: Preparation of 3-fluoro-N-(3-oxopropyl)-4-[5-(trifluoromethyl)-1,2,4-oxadiazol-3-yl]benzamide

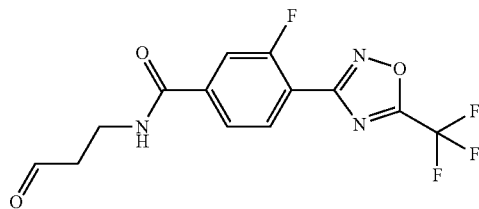 [SMILES: O=CCCNC(=O)c1ccc(-c2noc(C(F)(F)F)n2)c(F)c1]

To a solution of 3-fluoro-N-(3-hydroxypropyl)-4-[5-(trifluoromethyl)-1,2,4-oxadiazol-3-yl]benzamide (0.800 g, 2.40 mmol) in chloroform (7.20 mL) was added at 0° C., Dess-Martin Periodinane (1.23 g, 2.88 mmol). After stirring overnight at ambient temperature, saturated sodium thiosulfate (15 mL) was added and the organics were extracted using dichloromethane. The solvent was removed under reduced pressure and the resultant crude material was purified by flash chromatography over silica gel (cyclohexane:EtOAc eluent gradient 1:0 to 1:0.5) to afford the title compound as a white solid. LC/MS (Method D) retention time ($R_t$)=0.86 minutes, 332.27 (M+H).

Step 3: Preparation of N-[3-ethoxyiminopropyl]-3-fluoro-4-[5-(trifluoromethyl)-1,2,4-oxadiazol-3-yl]benzamide

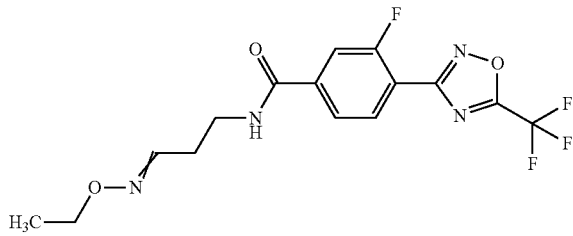 [SMILES: CCON=CCCNC(=O)c1ccc(-c2noc(C(F)(F)F)n2)c(F)c1]

To a solution of 3-fluoro-N-(3-oxopropyl)-4-[5-(trifluoromethyl)-1,2,4-oxadiazol-3-yl]benzamide (200 mg, 0.60 mmol) in ethanol (1.81 mL) was added at room temperature ethoxylamine hydrochloride (186 mg 1.81 mmol) and sodium acetate (148.6 mg, 1.81 mmol). The reaction mixture was heated at 80° C. for 16 h. The mixture was cooled to room temperature, filtered and the filtrate was evaporated under reduced pressure to obtain crude material. The resultant crude material was purified by flash chromatography over silica gel (cyclohexane:EtOAc eluent gradient 1:0 to 1:0.5) to afford the title compound as a white solid. LC/MS (Method D) retention time ($R_t$)=1.00 minutes, 375.27 (M+H).

Example 8: Preparation of N-cyclopropyl-N-[(2E)-2-methoxyiminoethyl]-4-[5-(trifluoromethyl)-1,2,4-oxadiazol-3-yl]benzamide (Compound 1.170 of Table T1)

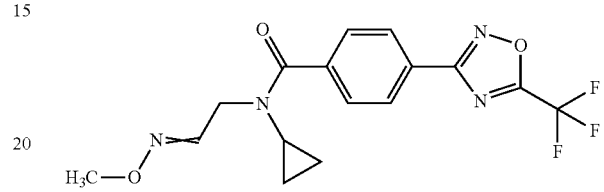

Step 1: Preparation of 2-(cyclopropylamino)ethanol

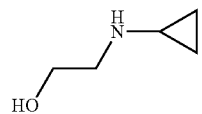

To a solution of 2-bromoethanol (2.19 g, 17.5 mmol,) in ethanol (20 mL) was added at ambient temperature, cyclopropylamine (1 g, 17.5 mmol). After stirring at ambient temperature for 24 hours, the solvent was removed under reduced pressure to give crude material. The resultant crude material was taken to next step without further purification.

Step 2: Preparation of N-cyclopropyl-N-(2-hydroxyethyl)-4-[5-(trifluoromethyl)-1,2,4-oxadiazol-3-yl]benzamide

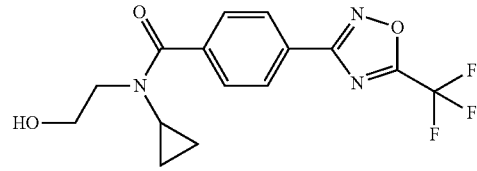 [SMILES: O=C(c1ccc(-c2noc(C(F)(F)F)n2)cc1)N(CCO)C1CC1]

To a solution of 4-[5-(trifluoromethyl)-1,2,4-oxadiazol-3-yl]benzoic acid (1 g, 3.87 mmol) in dichloromethane (10 mL) was added at ambient temperature, N-(3-dimethylaminopropyl)-N'-ethylcarbodiimide hydrochloride (0.99 g, 3.80 mmol) followed by triethylamine (1.64 mL, 11.6 mmol), 1-hydroxybenzotriazole hydrate (0.30 g, 1.94 mmol) and 2-(cyclopropylamino)ethanol (0.47 g, 4.65 mmol). After stirring at ambient temperature for 24 hours, water (25 mL) was added and the organics were extracted using dichloromethane. The solvent was removed under reduced pressure to give crude material. The resultant crude material was purified by flash chromatography over silica gel (cyclohexane:EtOAc eluent gradient 1:0 to 1:1) to afford the title compound as a white solid. LC/MS (Method C) retention time (R$_t$)=1.34 minutes, 341.9 (M+H).

Step 3: Preparation of N-cyclopropyl-N-(2-oxoethyl)-4-[5-(trifluoromethyl)-1,2,4-oxadiazol-3-yl]benzamide

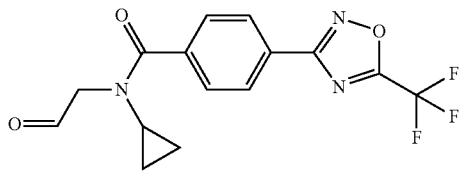 [SMILES: O=CCN(C(=O)c1ccc(-c2noc(C(F)(F)F)n2)cc1)C1CC1]

To a solution of N-cyclopropyl-N-(2-hydroxyethyl)-4-[5-(trifluoromethyl)-1,2,4-oxadiazol-3-yl]benzamide (100 mg, 0.29 mmol) in chloroform (0.88 mL) was added at 0° C., Dess-Martin Periodinane (188 mg, 0.44 mmol). After stirring overnight at ambient temperature, saturated sodium thiosulfate (10 mL) was added and the organics were extracted using dichloromethane. The solvent was removed under reduced pressure and the resultant crude material was purified by flash chromatography over silica gel (cyclohexane:EtOAc eluent gradient 1:0 to 1:1) to afford the title compound as a colorless gummy mass. LC/MS (Method C) retention time (R$_t$)=1.32 minutes, 337.7 (M–H).

Step 4: Preparation of N-cyclopropyl-N-[(2E)-2-methoxyiminoethyl]-4-[5-(trifluoromethyl)-1,2,4-oxadiazol-3-yl]benzamide To a solution of N-cyclopropyl-N-(2-oxoethyl)-4-[5-(trifluoromethyl)-1,2,4-oxadiazol-3-yl]benzamide (60 mg, 0.177 mmol) in ethanol (0.53 mL) was added at room temperature methoxyamine hydrochloride (45.2 mg 0.53 mmol) and sodium acetate (43.5 mg, 0.55 mmol). The reaction mixture was heated at 80° C. for 2 hours. The mixture was cooled to room temperature, filtered and the filtrate was evaporated under reduced pressure to obtain crude material. The resultant crude material was purified by flash chromatography over silica gel (cyclohexane:EtOAc eluent gradient 1:0 to 1:0.5) to afford the title compound as a white solid. LC/MS (Method C) retention time (R$_t$)=1.55 minutes, 369 (M+H).

Where necessary, enantiomerically pure final compounds may be obtained from racemic materials as appropriate via standard physical separation techniques, such as reverse phase chiral chromatography, or through stereoselective synthetic techniques, e.g., by using chiral starting materials.

TABLE T1

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.1 | N-(2-methoxyimino-1,1-dimethyl-ethyl)-4-[5-(trifluoromethyl)-1,2,4-oxadiazol-3-yl]benzamide | 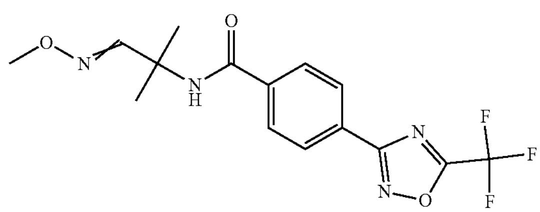 [SMILES: CON=CC(C)(C)NC(=O)c1ccc(-c2noc(C(F)(F)F)n2)cc1] | 1.65 | 356.11 | B | |
| 1.2 | 2-fluoro-N-(2-methoxyimino-1,1-dimethyl-ethyl)-4-[5-(trifluoromethyl)-1,2,4-oxadiazol-3-yl]benzamide | 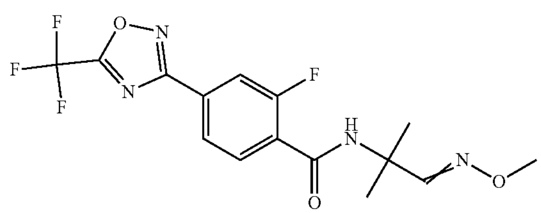 [SMILES: CON=CC(C)(C)NC(=O)c1ccc(-c2noc(C(F)(F)F)n2)cc1F] | 1.74<br>1.11 | 374.96<br>375 | B<br>A | |
| 1.3 | N-(2-methoxyimino-1-methyl-ethyl)-4-[5-(trifluoromethyl)-1,2,4-oxadiazol-3-yl]benzamide | 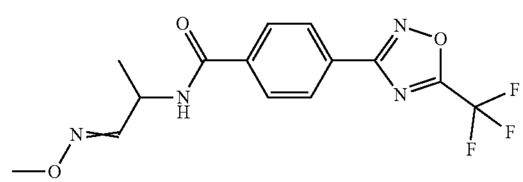 [SMILES: CON=CC(C)NC(=O)c1ccc(-c2noc(C(F)(F)F)n2)cc1] | 1.55 | 343.1 | A | 164-165 |
| 1.4 | 2-fluoro-N-[(2E)-2-methoxyimino-ethyl]-4-[5-(trifluoromethyl)-1,2,4-oxadiazol-3-yl]benzamide | 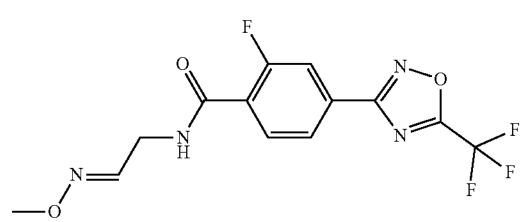 [SMILES: CO/N=C/CNC(=O)c1ccc(-c2noc(C(F)(F)F)n2)cc1F] | 0.97 | 347 | A | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.5 | N-[(Z)-methoxyimino methyl]-4-[5-(trifluoromethyl)-1,2,4-oxadiazol-3-yl]benzamide | 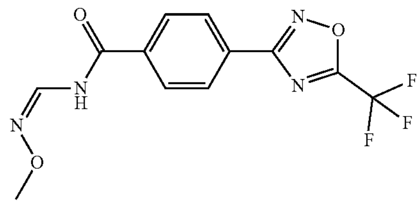 [SMILES: CO/N=C\NC(=O)c1ccc(-c2noc(C(F)(F)F)n2)cc1] | 1.56 | 315.2 | A | 135-140 |
| 1.6 | N-[(Z)-prop-2-ynoxyimino-methyl]-4-[5-(trifluoromethyl)-1,2,4-oxadiazol-3-yl]benzamide | 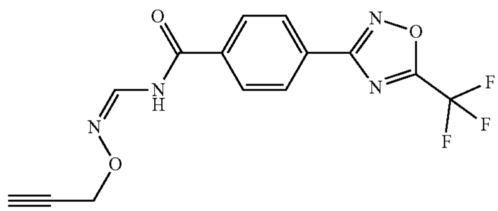 [SMILES: C#CCO/N=C\NC(=O)c1ccc(-c2noc(C(F)(F)F)n2)cc1] | 1.63 | 339.2 | A | 114-119 |
| 1.7 | N-[(2E)-1-methoxy-2-methoxyimino-propyl]-4-[5-(trifluoromethyl)-1,2,4-oxadiazol-3-yl]benzamide | 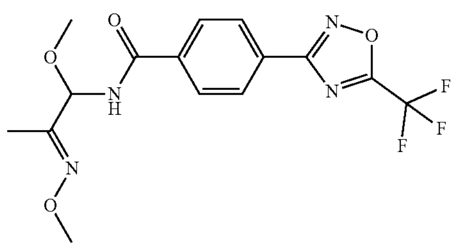 [SMILES: CO/N=C(\C)C(NC(=O)c1ccc(-c2noc(C(F)(F)F)n2)cc1)OC] | 1.03 | 373 | A | 100.7-106.9 |
| 1.8 | N-[(2E)-2-ethoxyimino-1-methyl-ethyl]-4-[5-(trifluoromethyl)-1,2,4-oxadiazol-3-yl]benzamide | 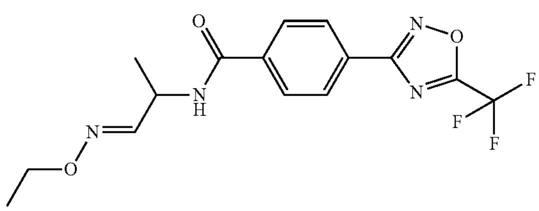 [SMILES: CCO/N=C/C(C)NC(=O)c1ccc(-c2noc(C(F)(F)F)n2)cc1] | | | | 142-143 |
| 1.9 | N-[(2Z)-2-ethoxyimino-1-methyl-ethyl]-4-[5-(trifluoromethyl)-1,2,4-oxadiazol-3-yl]benzamide | 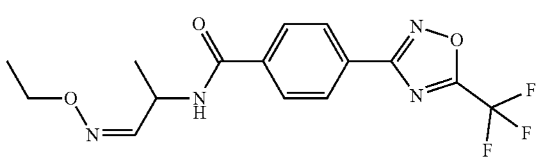 [SMILES: CCO/N=C\C(C)NC(=O)c1ccc(-c2noc(C(F)(F)F)n2)cc1] | | | | 173-174 |
| 1.10 | N-(2-methoxyimino-ethyl)-4-[5-(trifluoromethyl)-1,2,4-oxadiazol-3-yl]benzamide | 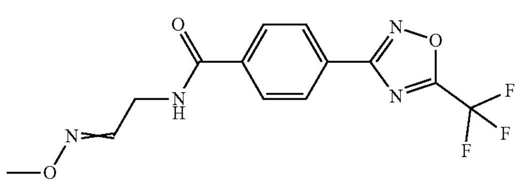 [SMILES: CON=CCNC(=O)c1ccc(-c2noc(C(F)(F)F)n2)cc1] | | | | 155-157 |
| 1.11 | N-(2-ethoxyiminoethyl)-4-[5-(trifluoromethyl)-1,2,4-oxadiazol-3-yl]benzamide | 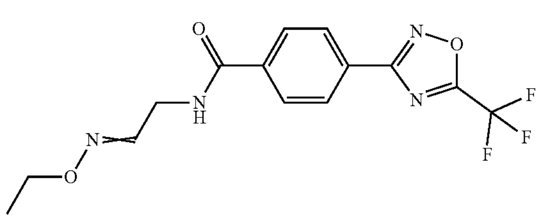 [SMILES: CCON=CCNC(=O)c1ccc(-c2noc(C(F)(F)F)n2)cc1] | | | | 156-158 |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.12 | N-(2-ethoxyimino-propyl)-4-[5-(trifluoromethyl)-1,2,4-oxadiazol-3-yl]benzamide | 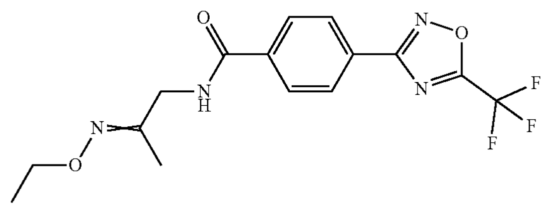 [SMILES: CCON=C(C)CNC(=O)c1ccc(-c2noc(C(F)(F)F)n2)cc1] | | | | 135-136 |
| 1.13 | N-[(2E)-2-methoxyimino-propyl]-4-[5-(trifluoromethyl)-1,2,4-oxadiazol-3-yl]benzamide | 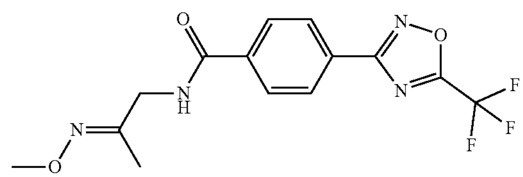 [SMILES: CO/N=C(\C)CNC(=O)c1ccc(-c2noc(C(F)(F)F)n2)cc1] | | | | 145-146 |
| 1.14 | N-[(2Z)-2-methoxyimino-propyl]-4-[5-(trifluoromethyl)-1,2,4-oxadiazol-3-yl]benzamide | 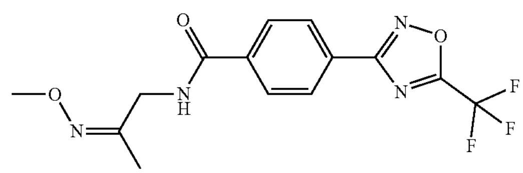 [SMILES: CO/N=C(/C)CNC(=O)c1ccc(-c2noc(C(F)(F)F)n2)cc1] | | | | 151-152 |
| 1.15 | N-[2-(2-hydroxyethoxy-imino)-1-methyl-ethyl]-4-[5-(trifluoromethyl)-1,2,4-oxadiazol-3-yl]benzamide | 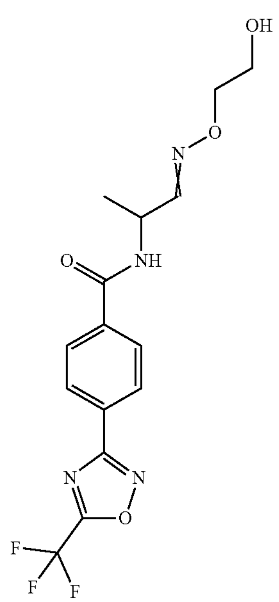 [SMILES: CC(C=NOCCO)NC(=O)c1ccc(-c2noc(C(F)(F)F)n2)cc1] | 1.29 | 373.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.16 | N-[1-methyl-2-[(4-nitrophenyl)methoxyimino]ethyl]-4-[5-(trifluoromethyl)-1,2,4-oxadiazol-3-yl]benzamide | 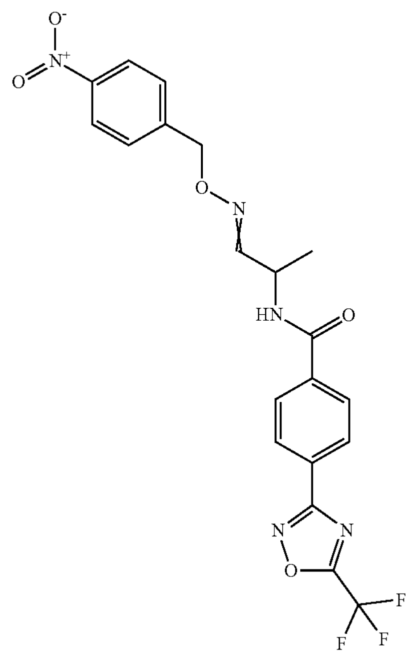 [SMILES: CC(C=NOCc1ccc([N+](=O)[O-])cc1)NC(=O)c1ccc(-c2noc(C(F)(F)F)n2)cc1] | 1.78 | 464.27 | B | |
| 1.17 | N-[2-[(3-methoxyphenyl)methoxyimino]-1-methyl-ethyl]-4-[5-(trifluoromethyl)-1,2,4-oxadiazol-3-yl]benzamide | 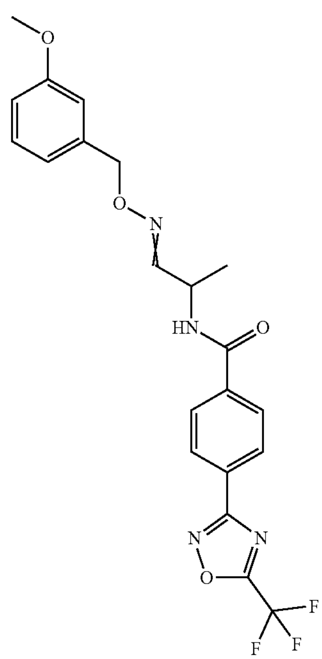 [SMILES: COc1cccc(CON=CC(C)NC(=O)c2ccc(-c3noc(C(F)(F)F)n3)cc2)c1] | 1.82 | 449.28 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.18 | N-[1-methyl-2-(p-tolylmethoxyimino)ethyl]-4-[5-(trifluoromethyl)-1,2,4-oxadiazol-3-yl]benzamide | 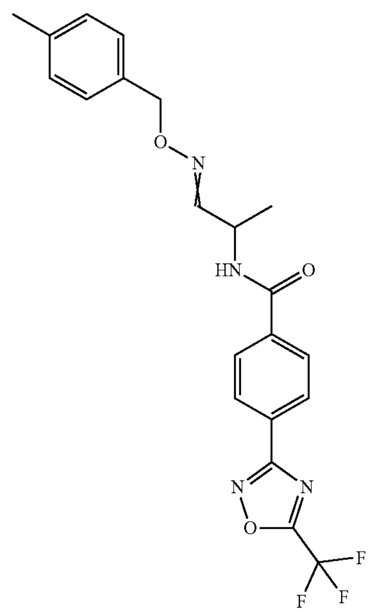 [SMILES: Cc1ccc(CON=CC(C)NC(=O)c2ccc(-c3noc(C(F)(F)F)n3)cc2)cc1] | 1.92 | 433.28 | B | |
| 1.19 | N-[2-[(4-methoxyphenyl)methoxyimino]-1-methyl-ethyl]-4-[5-(trifluoromethyl)-1,2,4-oxadiazol-3-yl]benzamide | 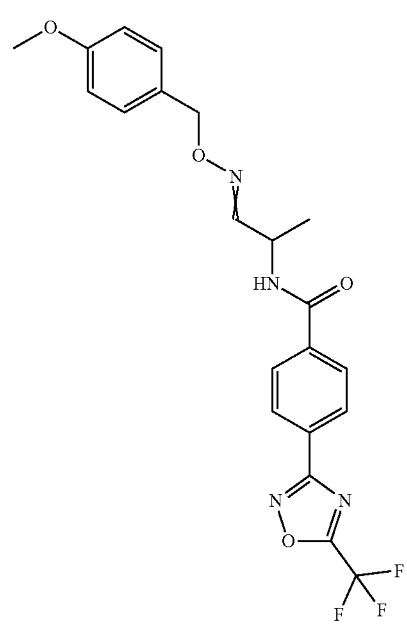 [SMILES: COc1ccc(CON=CC(C)NC(=O)c2ccc(-c3noc(C(F)(F)F)n3)cc2)cc1] | 1.81 | 449.29 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.20 | 2-[2-[[4-[5-(trifluoromethyl)-1,2,4-oxadiazol-3-yl]benzoyl]amino]propylidene-amino]oxyacetic acid | 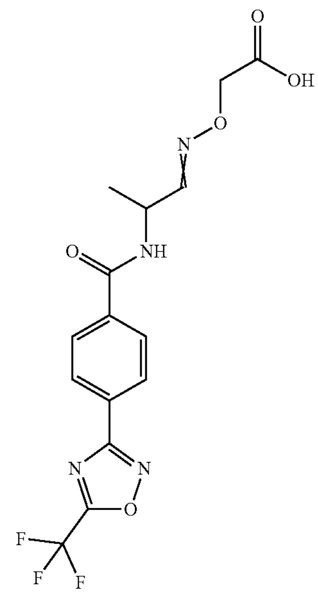 [SMILES: CC(C=NOCC(=O)O)NC(=O)c1ccc(-c2noc(C(F)(F)F)n2)cc1] | 1.29 | 387.2 | B | |
| 1.21 | N-[2-(2-aminoethoxy-imino)-1-methyl-ethyl]-4-[5-(trifluoromethyl)-1,2,4-oxadiazol-3-yl]benzamide | 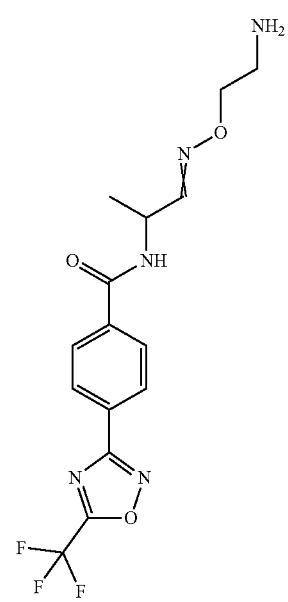 [SMILES: CC(C=NOCCN)NC(=O)c1ccc(-c2noc(C(F)(F)F)n2)cc1] | 0.93 | 372.23 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.22 | N-[2-[(2-chlorophenyl)methoxyimino]-1-methyl-ethyl]-4-[5-(trifluoromethyl)-1,2,4-oxadiazol-3-yl]benzamide | 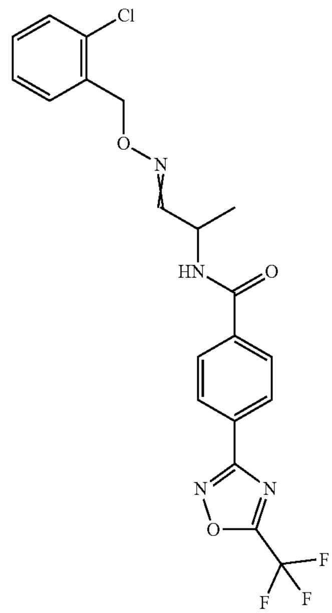 [SMILES: CC(C=NOCc1ccccc1Cl)NC(=O)c1ccc(-c2noc(C(F)(F)F)n2)cc1] | 1.93 | 453.24 | B | |
| 1.23 | N-[2-[(2-methoxyphenyl)methoxyimino]-1-methyl-ethyl]-4-[5-(trifluoromethyl)-1,2,4-oxadiazol-3-yl]benzamide | 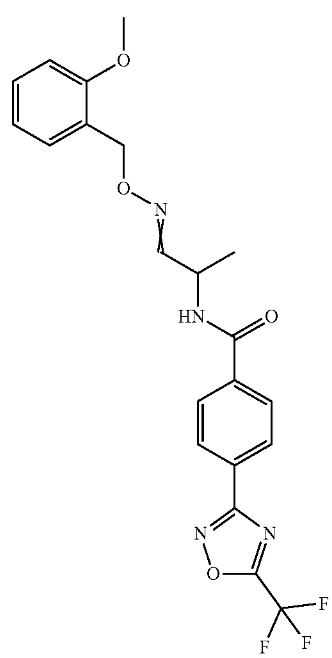 [SMILES: COc1ccccc1CON=CC(C)NC(=O)c1ccc(-c2noc(C(F)(F)F)n2)cc1] | 1.81 | 449.27 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.24 | N-[2-[(2-fluorophenyl)methoxyimino]-1-methyl-ethyl]-4-[5-(trifluoromethyl)-1,2,4-oxadiazol-3-yl]benzamide | 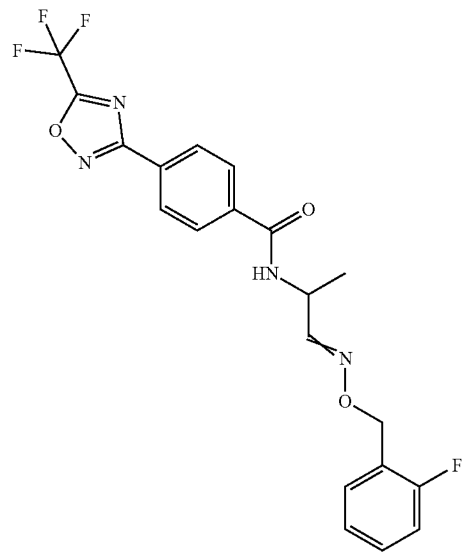 [SMILES: CC(C=NOCc1ccccc1F)NC(=O)c1ccc(-c2noc(C(F)(F)F)n2)cc1] | 1.84 | 437.26 | B | |
| 1.25 | N-(1-methyl-2-tetrahydropyran-2-yloxyimino-ethyl)-4-[5-(trifluoromethyl)-1,2,4-oxadiazol-3-yl]benzamide | 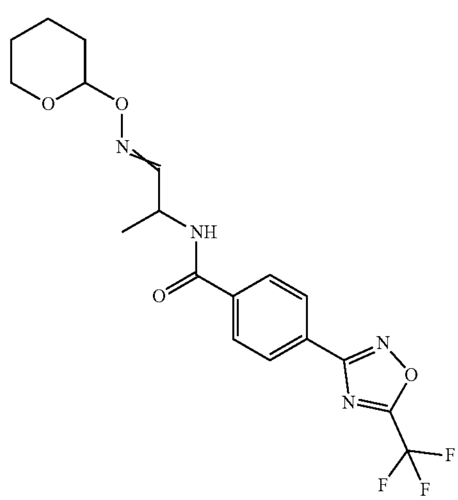 [SMILES: CC(C=NOC1CCCCO1)NC(=O)c1ccc(-c2noc(C(F)(F)F)n2)cc1] | 1.65 | 413.26 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.26 | N-[2-[(2-chloro-4-fluoro-phenyl)methoxy-imino]-1-methyl-ethyl]-5-[5-(trifluoromethyl)-1,2,4-oxadiazol-3-yl]benzamide | 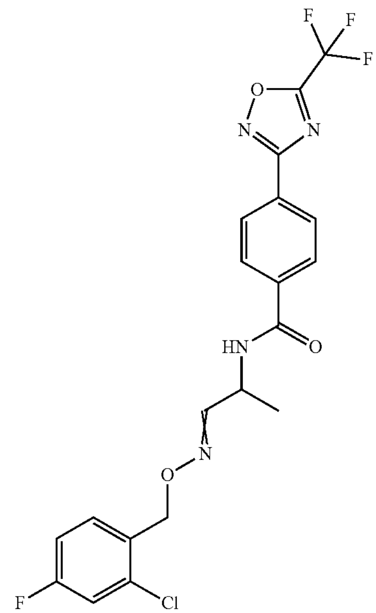 [SMILES: CC(C=NOCc1ccc(F)cc1Cl)NC(=O)c1ccc(-c2noc(C(F)(F)F)n2)cc1] | 1.96 | 471.23 | B | |
| 1.27 | N-(1-methyl-2-propoxyimino-ethyl)-4-[5-(trifluoromethyl)-1,2,4-oxadiazol-3-yl]benzamide | 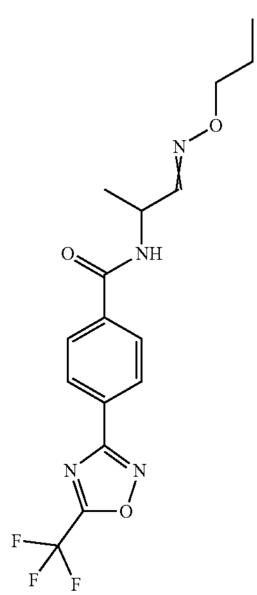 [SMILES: CCCON=CC(C)NC(=O)c1ccc(-c2noc(C(F)(F)F)n2)cc1] | 1.74 | 371.24 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.28 | N-(2-dodecoxyimino-1-methyl-ethyl)-4-[5-(trifluoromethyl)-1,2,4-oxadiazol-3-yl]benzamide | 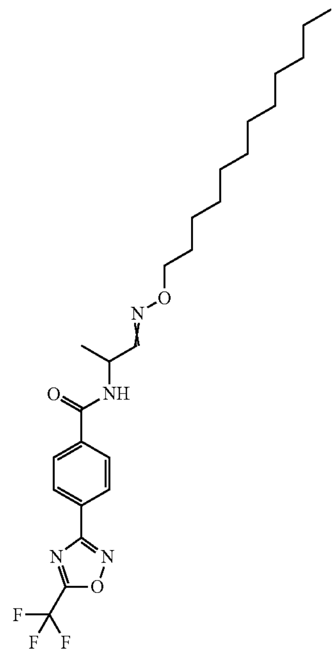 [SMILES: CCCCCCCCCCCCON=CC(C)NC(=O)c1ccc(-c2noc(C(F)(F)F)n2)cc1] | 2.57 | 497.43 | B | |
| 1.29 | (2R)-2-[2-[[4-[5-(trifluoromethyl)-1,2,4-oxadiazol-3-yl]benzoyl]amino]propylideneamino]oxypropanoic acid | 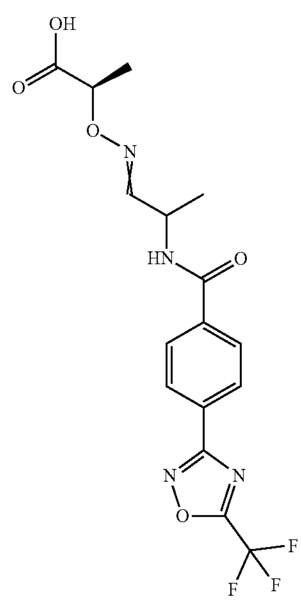 [SMILES: CC(C=NO[C@H](C)C(=O)O)NC(=O)c1ccc(-c2noc(C(F)(F)F)n2)cc1] | 1.68 | 429.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.30 | ethyl (2R)-2-[2-[[4-[5-(trifluoromethyl)-1,2,4-oxadiazol-3-yl]benzoyl]amino]propylideneamino]oxypropanoate | 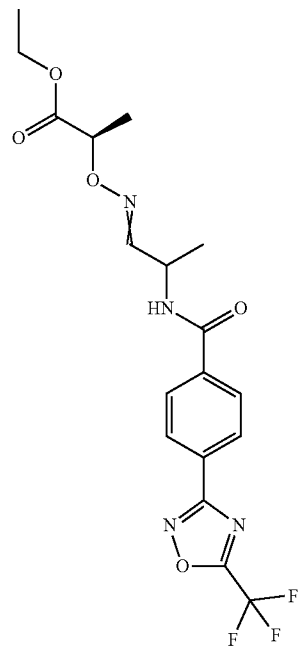 [SMILES: CCOC(=O)[C@@H](C)ON=CC(C)NC(=O)c1ccc(-c2noc(C(F)(F)F)n2)cc1] | 1.37 | 401.23 | B | |
| 1.31 | N-[2-[(4-bromophenyl)methoxyimino]-1-methyl-ethyl]-4-[5-(trifluoromethyl)-1,2,4-oxadiazol-3-yl]benzamide | 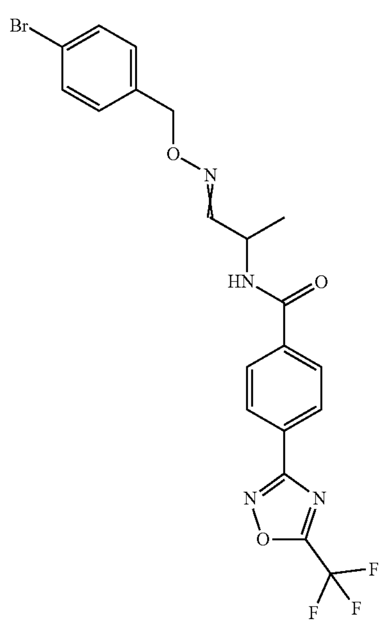 | 1.96 | 497.2 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.32 | (2S)-2-[2-[[4-[5-(trifluoromethyl)-1,2,4-oxadiazol-3-yl]benzoyl]amino]propylideneamino]oxypropanoic acid | 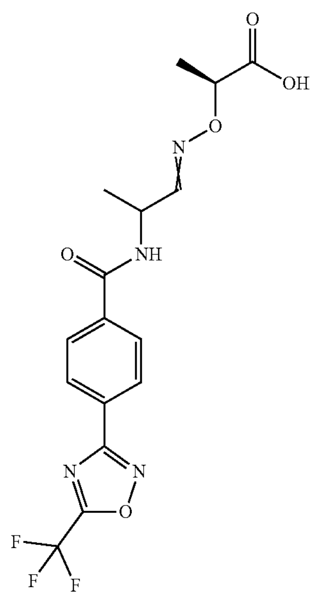 [SMILES: CC(C=NO[C@@H](C)C(=O)O)NC(=O)c1ccc(-c2noc(C(F)(F)F)n2)cc1] | 1.37 | 401.23 | B | |
| 1.33 | N-[2-(3-chloroallyloxyimino)-1-methylethyl]-4-[5-(trifluoromethyl)-1,2,4-oxadiazol-3-yl]benzamide | 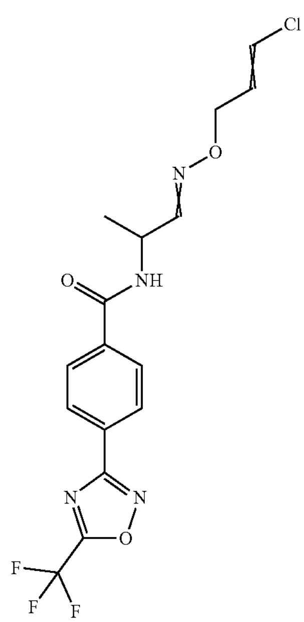 [SMILES: CC(C=NOCC=CCl)NC(=O)c1ccc(-c2noc(C(F)(F)F)n2)cc1] | 1.75 | 403.21 | B | |

TABLE T1-continued
Melting point (mp) and/or LC/MS data for compounds for Formula (I):
| Entry | Compound name | Structure | R$_t$ (min) | [M + H] (measured) | Method | mp (° C.) |
|---|---|---|---|---|---|---|
| 1.34 | N-[2-(3,3-dichloroallyl-oxyimino)-1-methyl-ethyl]-4-[5-(trifluoromethyl)-1,2,4-oxadiazol-3-yl]benzamide | 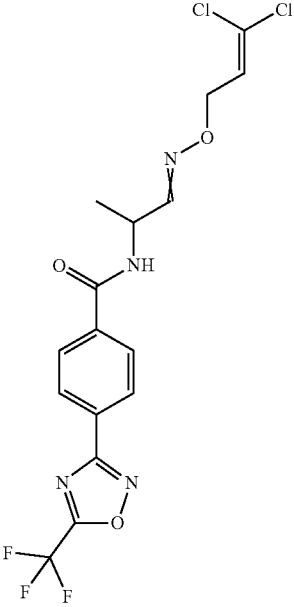 [SMILES: CC(C=NOCC=C(Cl)Cl)NC(=O)c1ccc(-c2noc(C(F)(F)F)n2)cc1] | 1.89 | 437.19 | B | |
| 1.35 | N-[1-methyl-2-(3-methylbut-2-enoxyimino)ethyl]-4-[5-(trifluoromethyl)-1,2,4-oxadiazol-3-yl]benzamide | 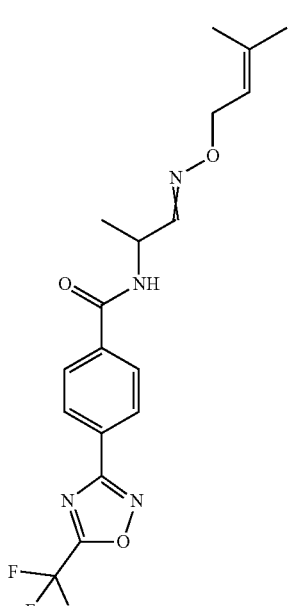 | 1.85 | 397.27 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.36 | N-[2-[(Z)-3-chloroallyloxy]imino-1-methyl-ethyl]-4-[5-(trifluoromethyl)-1,2,4-oxadiazol-3-yl]benzamide | 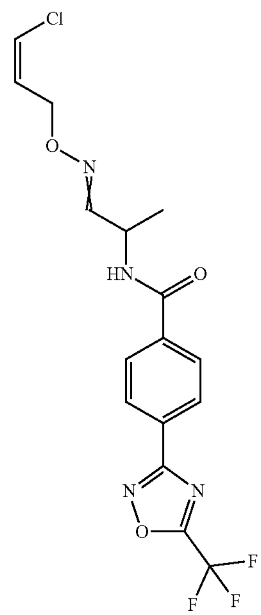 [SMILES: CC(C=NOC/C=C\Cl)NC(=O)c1ccc(-c2noc(C(F)(F)F)n2)cc1] | 1.75 | 403.2 | B | |
| 1.37 | 2-[2-[[4-[5-(trifluoromethyl)-1,2,4-oxadiazol-3-yl]benzoyl]amino]propylideneamino]oxypropanoic acid | 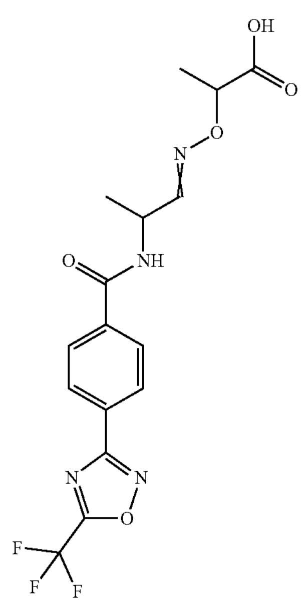 [SMILES: CC(C=NOC(C)C(=O)O)NC(=O)c1ccc(-c2noc(C(F)(F)F)n2)cc1] | 1.67 | 429.29 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.38 | ethyl 2-[2-[[4-[5-(trifluoromethyl)-1,2,4-oxadiazol-3-yl]benzoyl]amino]propylideneamino]oxypropanoate | 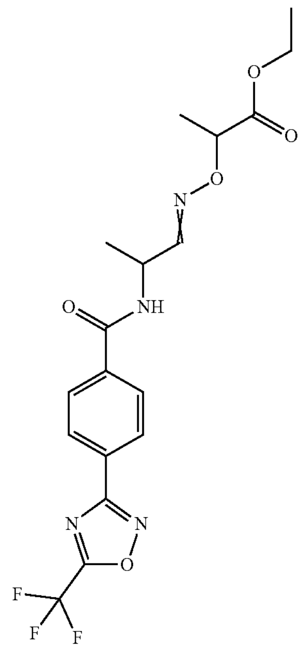 [SMILES: CCOC(=O)C(C)ON=CC(C)NC(=O)c1ccc(-c2noc(C(F)(F)F)n2)cc1] | 1.37 | 401.23 | B | |
| 1.39 | N-[2-[(2,6-dichlorophenyl)methoxyimino]-1-methyl-ethyl]-4-[5-(trifluoromethyl)-1,2,4-oxadiazol-3-yl]benzamide | 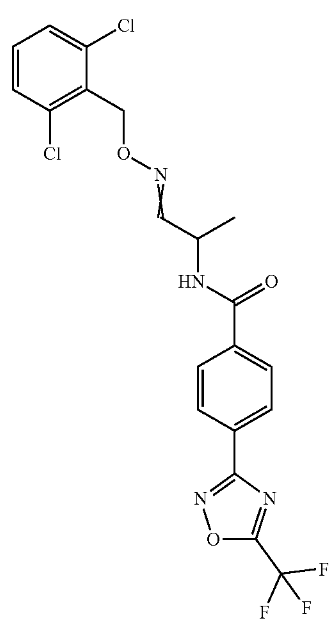 [SMILES: CC(C=NOCc1c(Cl)cccc1Cl)NC(=O)c1ccc(-c2noc(C(F)(F)F)n2)cc1] | 2 | 487.21 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.40 | N-(2-butoxyimino-1-methyl-ethyl)-4-[5-(trifluoromethyl)-1,2,4-oxadiazol-3-yl]benzamide | 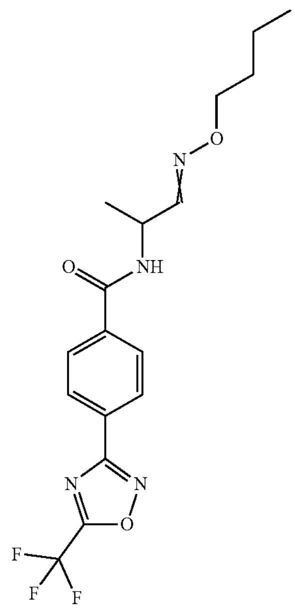 [SMILES: CCCCON=CC(C)NC(=O)c1ccc(-c2noc(C(F)(F)F)n2)cc1] | 1.86 | 385.26 | B | |
| 1.41 | N-(2-hexoxyimino-1-methyl-ethyl)-4-[5-(trifluoromethyl)-1,2,4-oxadiazol-3-yl]benzamide | 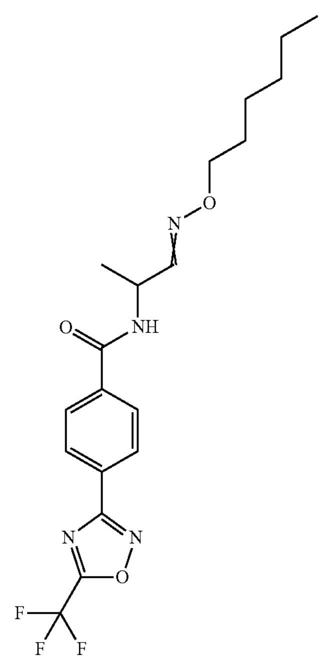 [SMILES: CCCCCCON=CC(C)NC(=O)c1ccc(-c2noc(C(F)(F)F)n2)cc1] | 2.06 | 413.31 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.42 | N-[1-methyl-2-[(2,3,4,5,6-pentafluorophenyl)methoxyimino]ethyl]-4-[5-(trifluoromethyl)-1,2,4-oxadiazol-3-yl]benzamide | 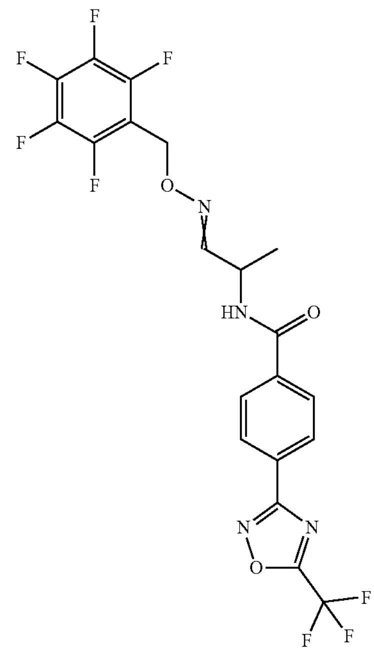 [SMILES: CC(C=NOCc1c(F)c(F)c(F)c(F)c1F)NC(=O)c1ccc(-c2noc(C(F)(F)F)n2)cc1] | 1.96 | 509.24 | B | |
| 1.43 | N-(2-ethoxyimino-1-methyl-ethyl)-4-[5-(trifluoromethyl)-1,2,4-oxadiazol-3-yl]benzamide | 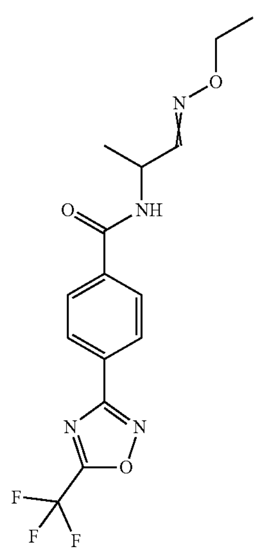 [SMILES: CCON=CC(C)NC(=O)c1ccc(-c2noc(C(F)(F)F)n2)cc1] | 1.62 | 357.22 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.44 | N-[1-methyl-2-[(2,4,5-trichlorophenyl)methoxyimino]ethyl]-4-[5-(trifluoromethyl)-1,2,4-oxadiazol-3-yl]benzamide | 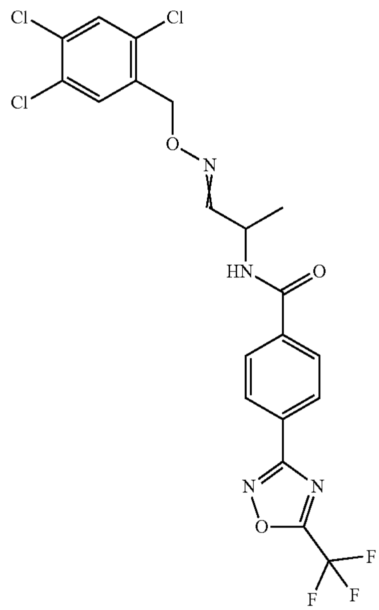 [SMILES: CC(C=NOCc1cc(Cl)c(Cl)cc1Cl)NC(=O)c1ccc(-c2noc(C(F)(F)F)n2)cc1] | 2.16 | 521.22 | B | |
| 1.45 | N-(2-tert-butoxyimino-1-methyl-ethyl)-4-[5-(trifluoromethyl)-1,2,4-oxadiazol-3-yl]benzamide | 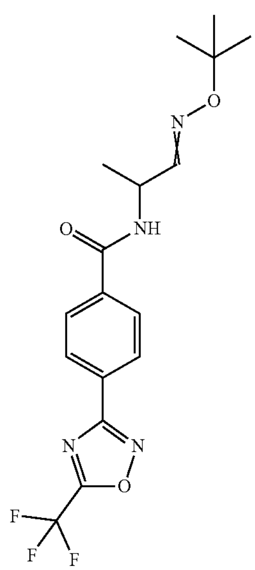 [SMILES: CC(C=NOC(C)(C)C)NC(=O)c1ccc(-c2noc(C(F)(F)F)n2)cc1] | 1.85 | 385.27 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.46 | N-(2-allyloxyimino-1-methyl-ethyl)-4-[5-(trifluoromethyl)-1,2,4-oxadiazol-3-yl]benzamide | 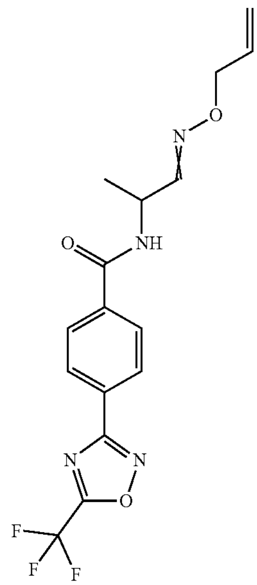 [SMILES: C=CCON=CC(C)NC(=O)c1ccc(-c2noc(C(F)(F)F)n2)cc1] | 1.67 | 369.23 | B | |
| 1.47 | N-(2-benzyloxyimino-1-methyl-ethyl)-4-[5-(trifluoromethyl)-1,2,4-oxadiazol-3-yl]benzamide | 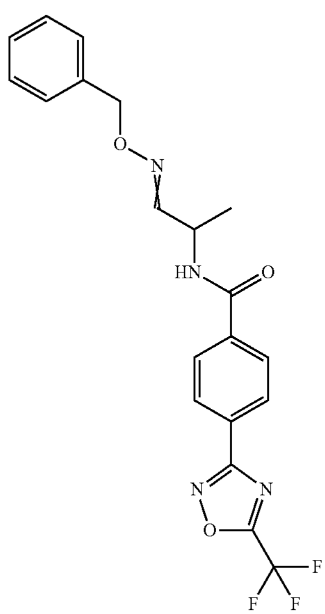 [SMILES: CC(C=NOCc1ccccc1)NC(=O)c1ccc(-c2noc(C(F)(F)F)n2)cc1] | 1.83 | 419.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.48 | 2-[2-[[2-[[4-[5-(trifluoromethyl)-1,2,4-oxadiazol-3-yl]benzoyl]amino]propylideneamino]oxymethyl]phenyl]acetic acid | 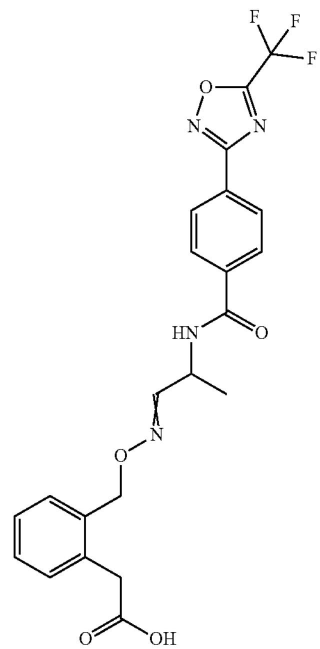 [SMILES: CC(C=NOCc1ccccc1CC(=O)O)NC(=O)c1ccc(-c2noc(C(F)(F)F)n2)cc1] | 1.78 | 491.34 | B | |
| 1.49 | methyl 2-[2-[[2-[[4-[5-(trifluoromethyl)-1,2,4-oxadiazol-3-yl]benzoyl]amino]propylideneamino]oxymethyl]phenyl]acetate | 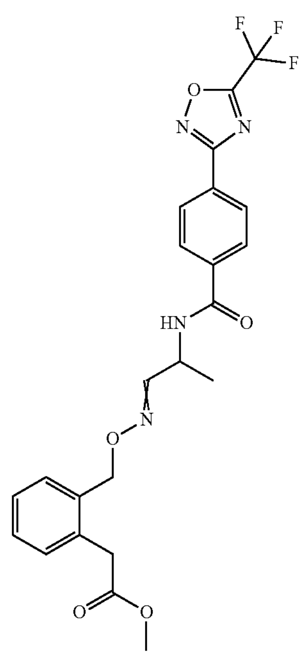 [SMILES: COC(=O)Cc1ccccc1CON=CC(C)NC(=O)c1ccc(-c2noc(C(F)(F)F)n2)cc1] | 1.58 | 477.3 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.50 | N-(2-isopropoxyimino-1-methyl-ethyl)-4-[5-(trifluoromethyl)-1,2,4-oxadiazol-3-yl]benzamide | 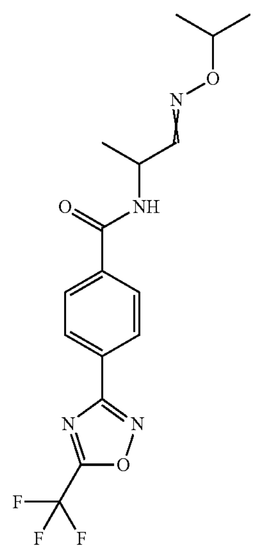 [SMILES: CC(C=NOC(C)C)NC(=O)c1ccc(-c2noc(C(F)(F)F)n2)cc1] | 1.73 | 371.24 | B | |
| 1.51 | N-[1-methyl-2-(2,2,2-trifluoroethoxy-imino)ethyl]-4-[5-(trifluoromethyl)-1,2,4-oxadiazol-3-yl]benzamide | 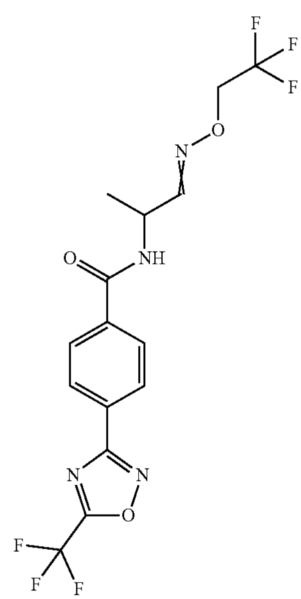 [SMILES: CC(C=NOCC(F)(F)F)NC(=O)c1ccc(-c2noc(C(F)(F)F)n2)cc1] | 1.71 | 411.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.52 | N-[2-[(4-fluorophenyl)methoxyimino]-1-methyl-ethyl]-4-[5-(trifluoromethyl)-1,2,4-oxadiazol-3-yl]benzamide | 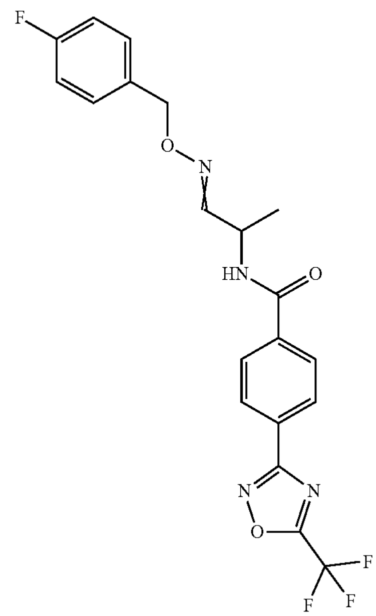 [SMILES: CC(C=NOCc1ccc(F)cc1)NC(=O)c1ccc(-c2noc(C(F)(F)F)n2)cc1] | 1.83 | 437.27 | B | |
| 1.53 | N-[2-[(3-chlorophenyl)methoxyimino]-1-methyl-ethyl]-4-[5-(trifluoromethyl)-1,2,4-oxadiazol-3-yl]benzamide | 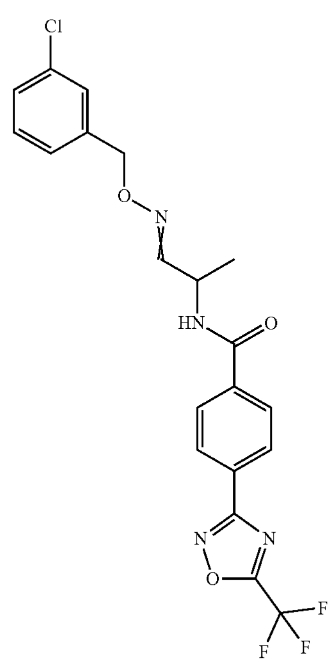 [SMILES: CC(C=NOCc1cccc(Cl)c1)NC(=O)c1ccc(-c2noc(C(F)(F)F)n2)cc1] | 1.94 | 453.24 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.54 | N-[1-methyl-2-[[3-(trifluoromethyl)phenyl]methoxyimino]ethyl-4-[5-(trifluoromethyl)-1,2,4-oxadiazol-3-yl]benzamide | 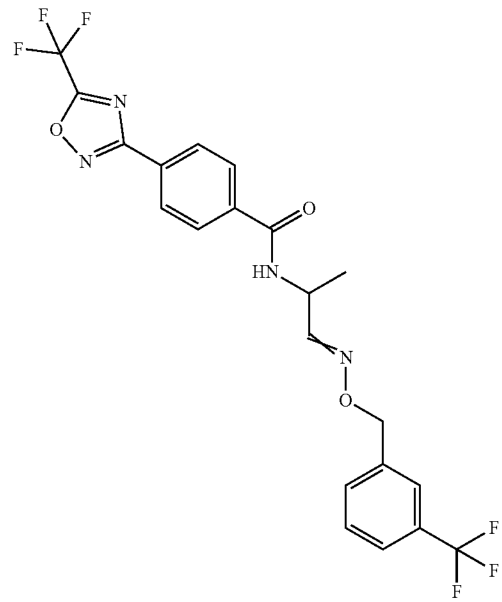 [SMILES: CC(C=NOCc1cccc(C(F)(F)F)c1)NC(=O)c1ccc(-c2noc(C(F)(F)F)n2)cc1] | 1.96 | 487.28 | B | |
| 1.55 | N-[1-methyl-2-[[2-(trifluoromethyl)phenyl]methoxyimino]ethyl]-4-[5-(trifluoromethyl)-1,2,4-oxadiazol-3-yl]benzamide | 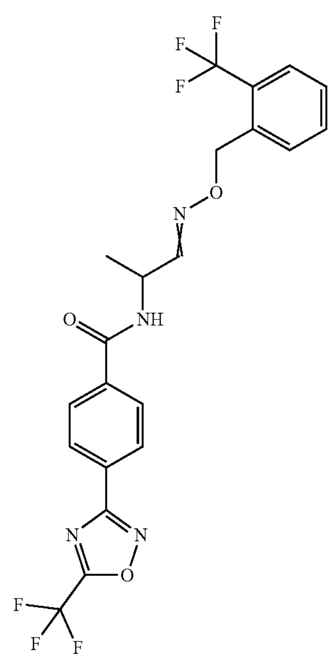 [SMILES: CC(C=NOCc1ccccc1C(F)(F)F)NC(=O)c1ccc(-c2noc(C(F)(F)F)n2)cc1] | 1.97 | 487.28 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.56 | N-[2-(2-chloroallyloxy-imino)-1-methyl-ethyl]-4-[5-(trifluoromethyl)-1,2,4-oxadiazol-3-yl]benzamide | 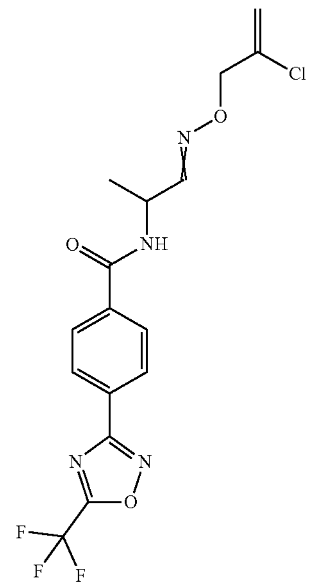 | 1.76 | 403.21 | B | |
| 1.57 | N-[2-(cyclopropyl-methoxyimino)-1-methyl-ethyl]-4-[5-(trifluoromethyl)-1,2,4-oxadiazol-3-yl]benzamide | 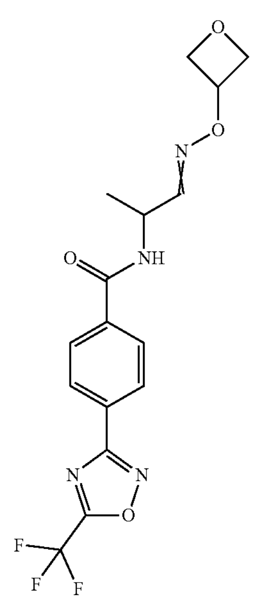 [SMILES: CC(C=NOC1COC1)NC(=O)c1ccc(-c2noc(C(F)(F)F)n2)cc1] | 1.73 | 383.25 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.58 | N-[1-methyl-2-(oxetan-3-yloxyimino)ethyl]-4-[5-(trifluoromethyl)-1,2,4-oxadiazol-3-yl]benzamide | 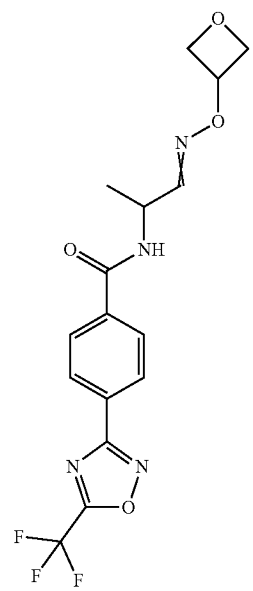 [SMILES: CC(C=NOC1COC1)NC(=O)c1ccc(-c2noc(C(F)(F)F)n2)cc1] | 1.42 | 385.23 | B | |
| 1.59 | N-[2-[(4-chlorophenyl)methoxyimino]-1-methyl-ethyl]-4-[5-(trifluoromethyl)-1,2,4-oxadiazol-3-yl]benzamide | 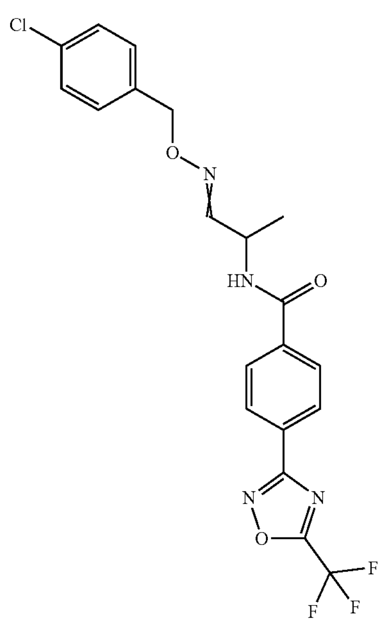 [SMILES: CC(C=NOCc1ccc(Cl)cc1)NC(=O)c1ccc(-c2noc(C(F)(F)F)n2)cc1] | 1.93 | 453.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.60 | N-[2-(2-hydroxyethoxyimino)ethyl]-4-[5-(trifluoromethyl)-1,2,4-oxadiazol-3-yl]benzamide | 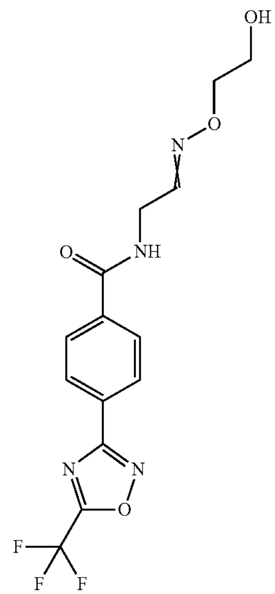 [SMILES: O=C(NCC=NOCCO)c1ccc(-c2noc(C(F)(F)F)n2)cc1] | 1.2 | 359.2 | B | |
| 1.61 | N-[2-[(4-nitrophenyl)methoxyimino]ethyl]-4-[5-(trifluoromethyl)-1,2,4-oxadiazol-3-yl]benzamide | 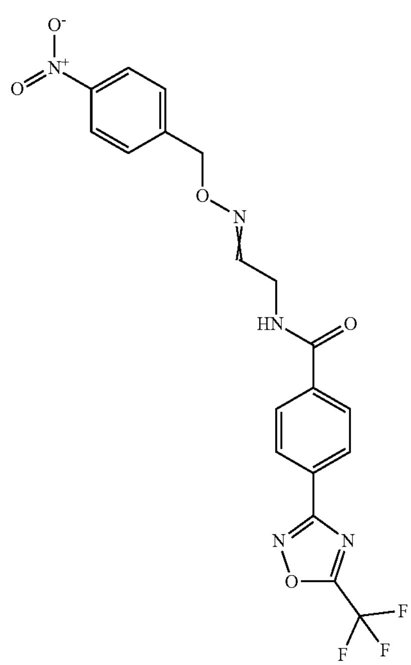 [SMILES: O=C(NCC=NOCc1ccc([N+](=O)[O-])cc1)c1ccc(-c2noc(C(F)(F)F)n2)cc1] | 1.71 | 450.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.62 | N-[2-[(3-methoxyphenyl)methoxyimino]ethyl]-4-[5-(trifluoromethyl)-1,2,4-oxadiazol-3-yl]benzamide | 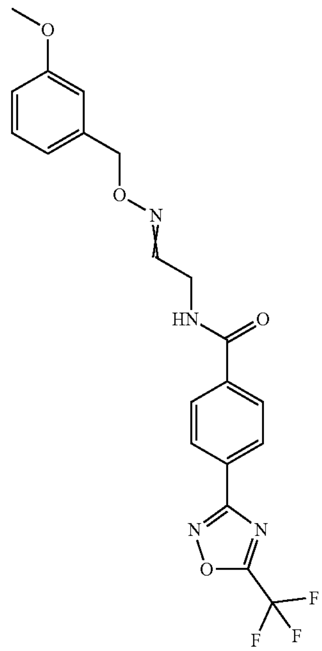 [SMILES: COc1cccc(CON=CCNC(=O)c2ccc(-c3noc(C(F)(F)F)n3)cc2)c1] | 1.74 | 435.27 | B | |
| 1.63 | N-[2-(p-tolylmethoxy-imino)ethyl]-4-[5-(trifluoromethyl)-1,2,4-oxadiazol-3-yl]benzamide | 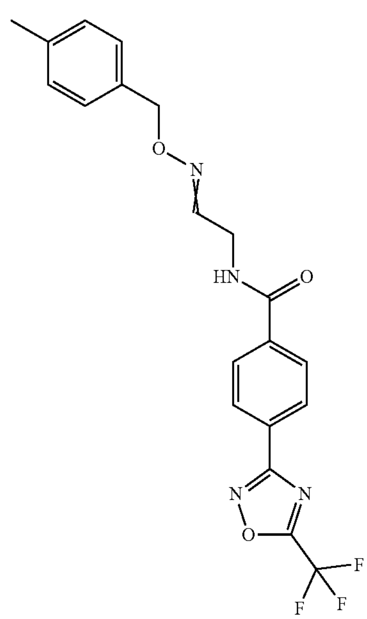 [SMILES: Cc1ccc(CON=CCNC(=O)c2ccc(-c3noc(C(F)(F)F)n3)cc2)cc1] | 1.84 | 419.28 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.64 | N-[2-[(4-methoxyphenyl)methoxyimino]ethyl]-4-[5-(trifluoromethyl)-1,2,4-oxadiazol-3-yl]benzamide | 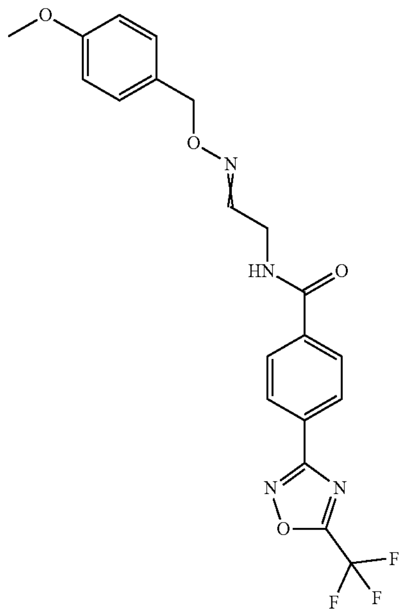 [SMILES: COc1ccc(CON=CCNC(=O)c2ccc(-c3noc(C(F)(F)F)n3)cc2)cc1] | 1.72 | 435.28 | B | |
| 1.65 | 2-[2-[[4-[5-(trifluoromethyl)-1,2,4-oxadiazol-3-yl]benzoyl]amino]ethylideneamino]oxyacetic acid | 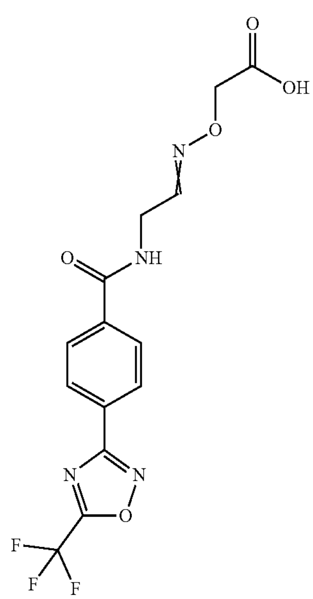 [SMILES: O=C(O)CON=CCNC(=O)c1ccc(-c2noc(C(F)(F)F)n2)cc1] | 1.21 | 373.19 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.66 | N-[2-(2-aminoethoxyimino)ethyl]-4-[5-(trifluoromethyl)-1,2,4-oxadiazol-3-yl]benzamide | 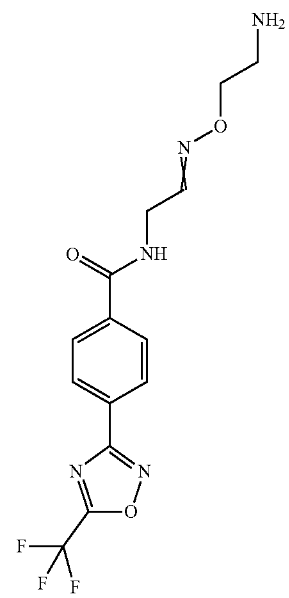 [SMILES: NCCON=CCNC(=O)c1ccc(-c2noc(C(F)(F)F)n2)cc1] | 0.87 | 358.23 | B | |
| 1.67 | N-[2-[(2-chlorophenyl)methoxyimino]ethyl]-4-[5-(trifluoromethyl)-1,2,4-oxadiazol-3-yl]benzamide | 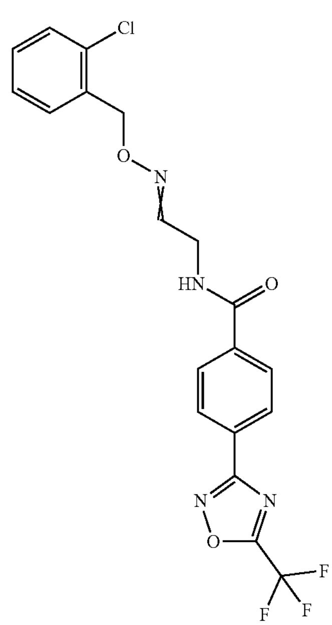 [SMILES: O=C(NCC=NOCc1ccccc1Cl)c1ccc(-c2noc(C(F)(F)F)n2)cc1] | 1.85 | 439.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.68 | N-[2-[(2-methoxyphenyl)methoxyimino]ethyl]-4-[5-(trifluoromethyl)-1,2,4-oxadiazol-3-yl]benzamide | 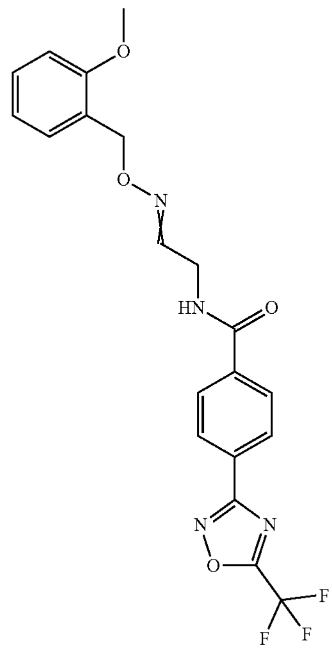 [SMILES: COc1ccccc1CON=CCNC(=O)c1ccc(-c2noc(C(F)(F)F)n2)cc1] | 1.72 | 435.27 | B | |
| 1.69 | N-[2-[(2-fluorophenyl)methoxyimino]ethyl]-4-[5-(trifluoromethyl)-1,2,4-oxadiazol-3-yl]benzamide | 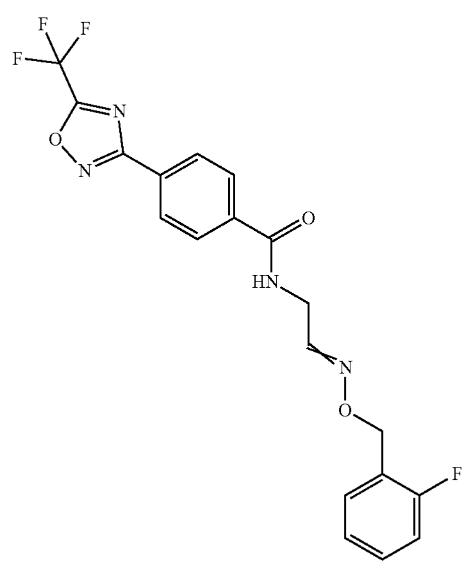 [SMILES: O=C(NCC=NOCc1ccccc1F)c1ccc(-c2noc(C(F)(F)F)n2)cc1] | 1.76 | 423.25 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.70 | N-(2-tetrahydropyran-2-yloxyiminoethyl)-4-[5-(trifluoromethyl)-1,2,4-oxadiazol-3-yl]benzamide | 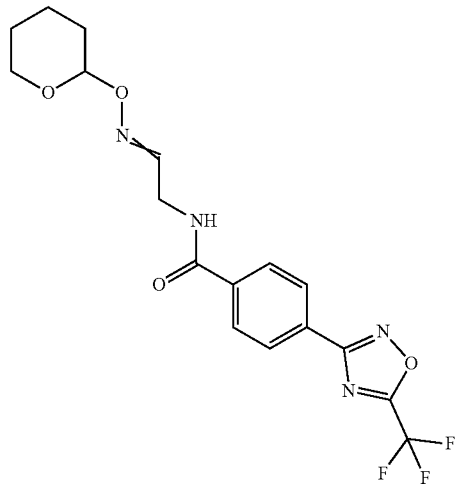 [SMILES: O=C(NCC=NOC1CCCCO1)c1ccc(-c2noc(C(F)(F)F)n2)cc1] | 1.56 | 399.26 | B | |
| 1.71 | N-[2-[(2-chloro-4-fluorophenyl)methoxyimino]ethyl]-4-[5-(trifluoromethyl)-1,2,4-oxadiazol-3-yl]benzamide | 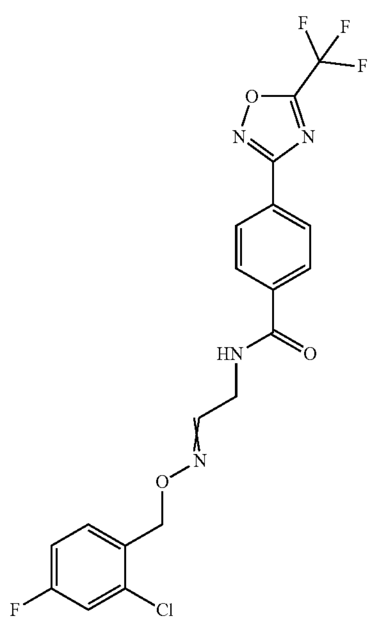 [SMILES: O=C(NCC=NOCc1ccc(F)cc1Cl)c1ccc(-c2noc(C(F)(F)F)n2)cc1] | 1.88 | 457.23 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.72 | N-(2-propoxyiminoethyl)-4-[5-(trifluoromethyl)-1,2,4-oxadiazol-3-yl]benzamide | 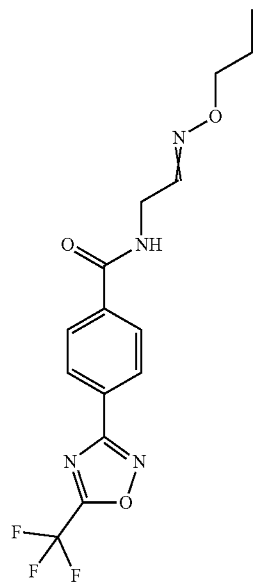 [SMILES: CCCON=CCNC(=O)c1ccc(-c2noc(C(F)(F)F)n2)cc1] | 1.64 | 357.23 | B | |
| 1.73 | N-(2-dodecoxyiminoethyl)-4-[5-(trifluoromethyl)-1,2,4-oxadiazol-3-yl]benzamide | 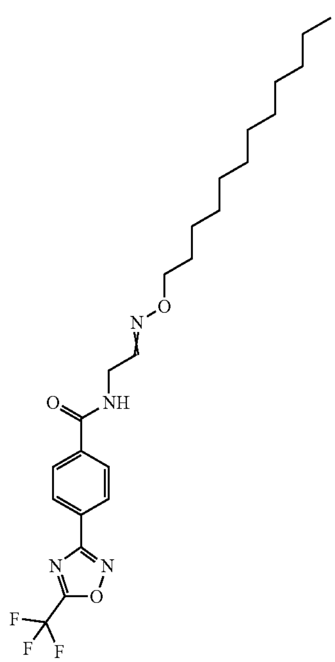 [SMILES: CCCCCCCCCCCCON=CCNC(=O)c1ccc(-c2noc(C(F)(F)F)n2)cc1] | 2.51 | 483.42 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.74 | (2R)-2-[2-[[4-[5-(trifluoromethyl)-1,2,4-oxadiazol-3-yl]benzoyl]amino]ethylideneamino]oxypropanoic acid | 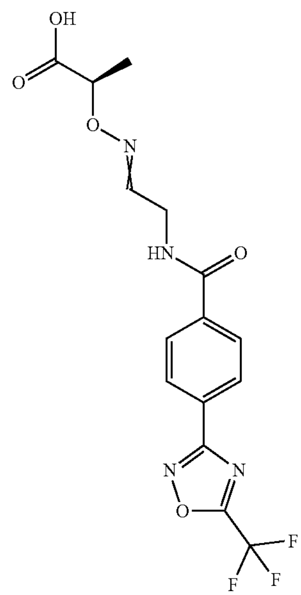 [SMILES: C[C@@H](ON=CCNC(=O)c1ccc(-c2noc(C(F)(F)F)n2)cc1)C(=O)O] | 1.6 | 415.24 | B | |
| 1.75 | ethyl (2R)-2-[2-[[4-[5-(trifluoromethyl)-1,2,4-oxadiazol-3-yl]benzoyl]amino]ethylideneamino]oxypropanoate | 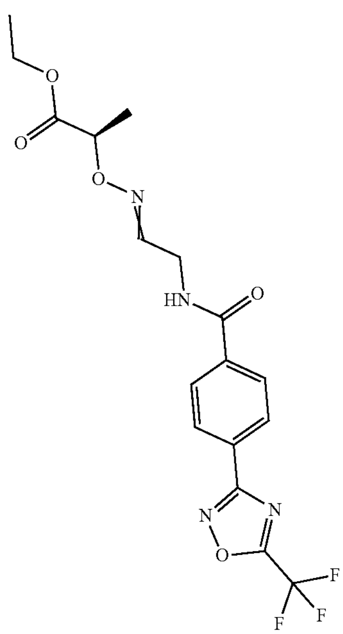 [SMILES: CCOC(=O)[C@@H](C)ON=CCNC(=O)c1ccc(-c2noc(C(F)(F)F)n2)cc1] | 1.32 | 387.21 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.76 | N-[2-[(4-bromophenyl)methoxyimino]ethyl]-4-[5-(trifluoromethyl)-1,2,4-oxadiazol-3-yl]benzamide | 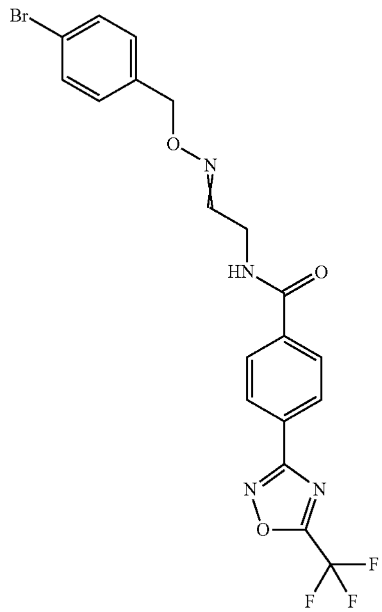 [SMILES: O=C(NCC=NOCc1ccc(Br)cc1)c1ccc(-c2noc(C(F)(F)F)n2)cc1] | 1.88 | 483.19 | B | |
| 1.77 | (2S)-2-[2-[[4-[5-(trifluoromethyl)-1,2,4-oxadiazol-3-yl]benzoyl]amino]ethylideneamino]oxypropanoic acid | 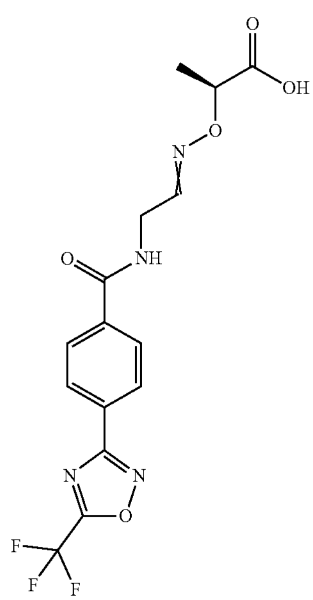 [SMILES: C[C@H](ON=CCNC(=O)c1ccc(-c2noc(C(F)(F)F)n2)cc1)C(=O)O] | 1.29 | 387.21 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.78 | N-[2-(3-chloroallyloxyimino)ethyl]-4-[5-(trifluoromethyl)-1,2,4-oxadiazol-3-yl]benzamide | 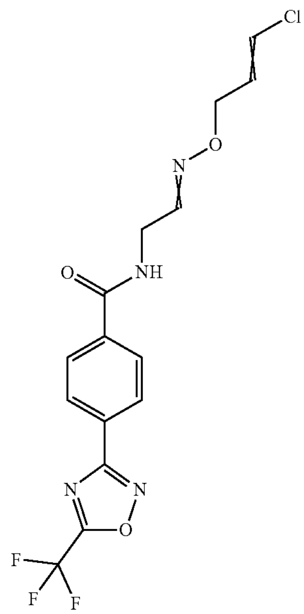 [SMILES: O=C(NCC=NOCC=CCl)c1ccc(-c2noc(C(F)(F)F)n2)cc1] | 1.66 | 389.19 | B | |
| 1.79 | N-[2-(3,3-dichloroallyloxyimino)ethyl]-4-[5-(trifluoromethyl)-1,2,4-oxadiazol-3-yl]benzamide | 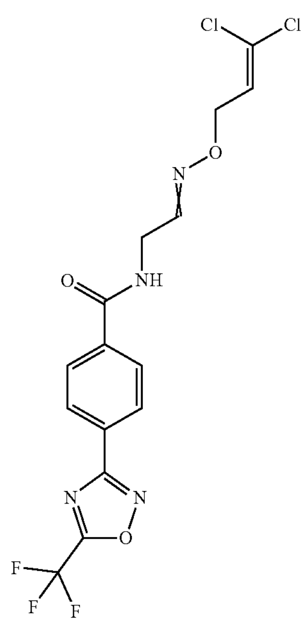 [SMILES: O=C(NCC=NOCC=C(Cl)Cl)c1ccc(-c2noc(C(F)(F)F)n2)cc1] | 1.8 | 423.17 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.80 | N-[2-(3-methylbut-2-enoxyimino)ethyl]-4-[5-(trifluoromethyl)-1,2,4-oxadiazol-3-yl]benzamide | 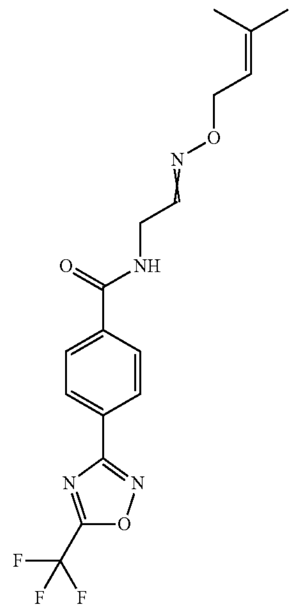 [SMILES: CC(C)=CCON=CCNC(=O)c1ccc(-c2noc(C(F)(F)F)n2)cc1] | 1.75 | 383.24 | B | |
| 1.81 | N-[2-[(Z)-3-chloroallyloxy]iminoethyl]-4-[5-(trifluoromethyl)-1,2,4-oxadiazol-3-yl]benzamide | 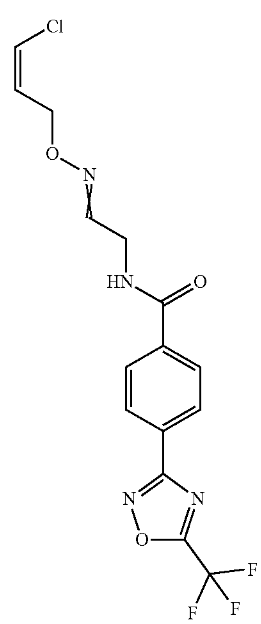 [SMILES: O=C(NCC=NOC/C=C\Cl)c1ccc(-c2noc(C(F)(F)F)n2)cc1] | 1.66 | 389.18 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.82 | 2-[2-[[4-[5-(trifluoromethyl)-1,2,4-oxadiazol-3-yl]benzoyl]amino]ethylideneamino]oxypropanoic acid | 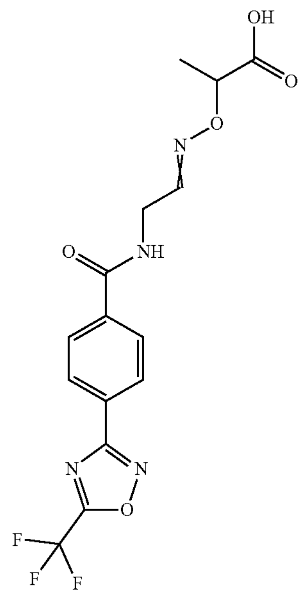 [SMILES: CC(ON=CCNC(=O)c1ccc(-c2noc(C(F)(F)F)n2)cc1)C(=O)O] | 1.59 | 415.25 | B | |
| 1.83 | ethyl 2-[2-[[4-[5-(trifluoromethyl)-1,2,4-oxadiazol-3-yl]benzoyl]amino]ethylideneamino]oxypropanoate | 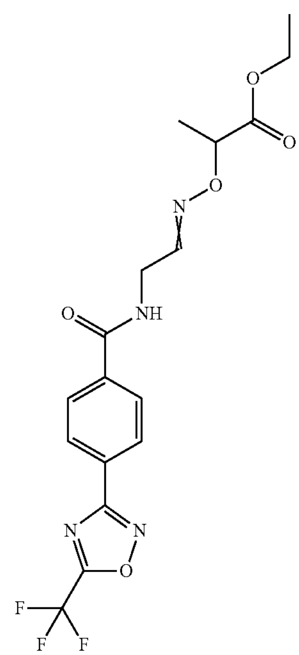 [SMILES: CCOC(=O)C(C)ON=CCNC(=O)c1ccc(-c2noc(C(F)(F)F)n2)cc1] | 1.32 | 387.21 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.84 | N-[2-[(2,6-dichlorophenyl)methoxyimino]ethyl]-4-[5-(trifluoromethyl)-1,2,4-oxadiazol-3-yl]benzamide | 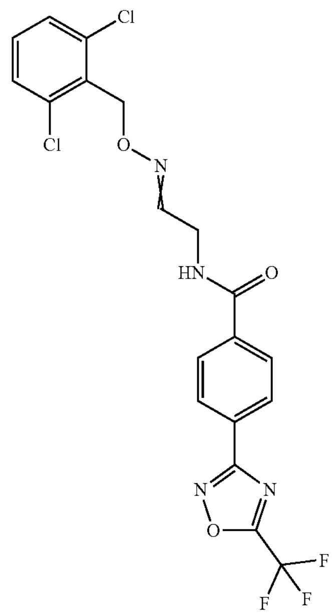 [SMILES: O=C(NCC=NOCc1c(Cl)cccc1Cl)c1ccc(-c2noc(C(F)(F)F)n2)cc1] | 1.91 | 473.2 | B | |
| 1.85 | N-(2-butoxyiminoethyl)-4-[5-(trifluoromethyl)-1,2,4-oxadiazol-3-yl]benzamide | 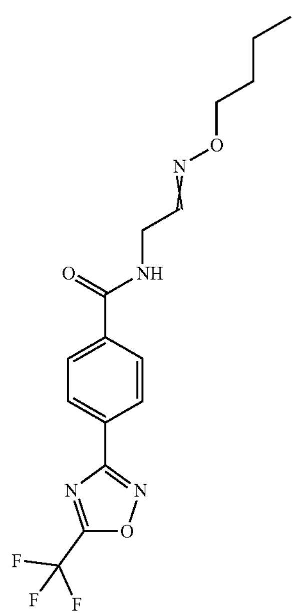 [SMILES: CCCCON=CCNC(=O)c1ccc(-c2noc(C(F)(F)F)n2)cc1] | 1.76 | 371.25 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.86 | N-(2-hexoxyiminoethyl)-4-[5-(trifluoromethyl)-1,2,4-oxadiazol-3-yl]benzamide | 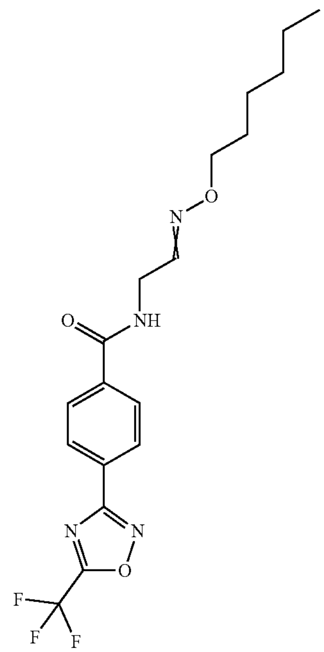 [SMILES: CCCCCCON=CCNC(=O)c1ccc(-c2noc(C(F)(F)F)n2)cc1] | 1.98 | 399.29 | B | |
| 1.87 | N-[2-[(2,3,4,5,6-pentafluorophenyl)methoxyimino]ethyl]-4-[5-(trifluoromethyl)-1,2,4-oxadiazol-3-yl]benzamide | 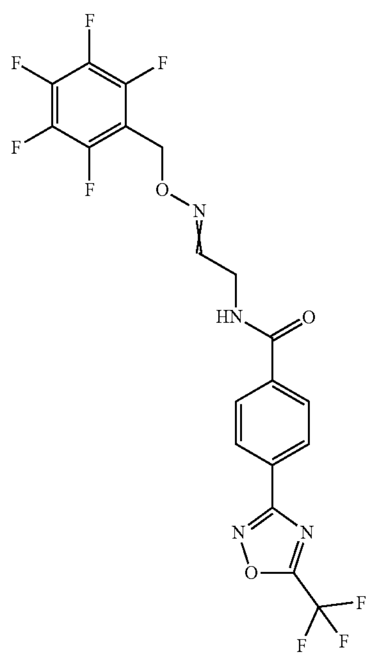 [SMILES: O=C(NCC=NOCc1c(F)c(F)c(F)c(F)c1F)c1ccc(-c2noc(C(F)(F)F)n2)cc1] | 1.88 | 495.25 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.88 | N-[2-[(2,4,5-trichlorophenyl)methoxyimino]ethyl]-4-[5-(trifluoromethyl)-1,2,4-oxadiazol-3-yl]benzamide | 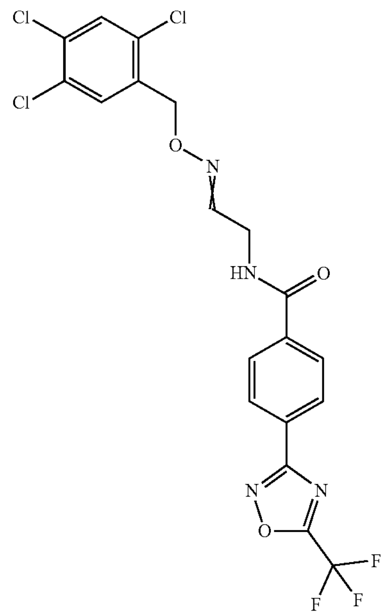 [SMILES: O=C(NCC=NOCc1cc(Cl)c(Cl)cc1Cl)c1ccc(-c2noc(C(F)(F)F)n2)cc1] | 2.09 | 507.19 | B | |
| 1.89 | N-(2-tert-butoxyiminoethyl)-4-[5-(trifluoromethyl)-1,2,4-oxadiazol-3-yl]benzamide | 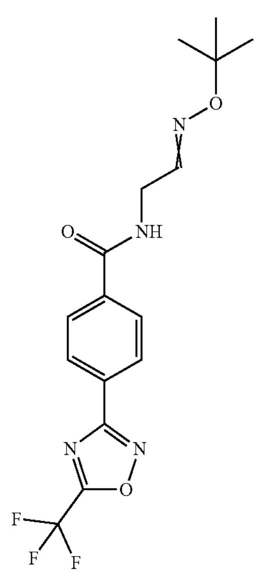 | 1.75 | 371.24 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.90 | N-(2-benzyloxyimino-ethyl)-4-[5-(trifluoromethyl)-1,2,4-oxadiazol-3-yl]benzamide | 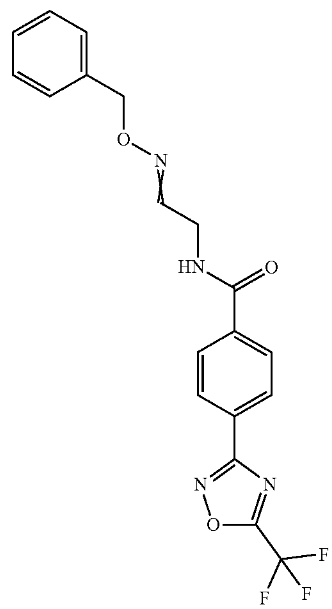 [SMILES: O=C(NCC=NOCc1ccccc1)c1ccc(-c2noc(C(F)(F)F)n2)cc1] | 1.74 | 405.24 | B | |
| 1.91 | N-(2-allyloxyiminoethyl)-4-[5-(trifluoromethyl)-1,2,4-oxadiazol-3-yl]benzamide | 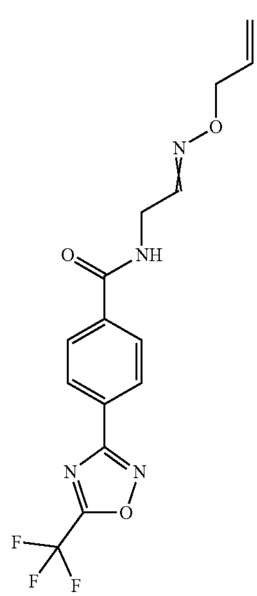 [SMILES: C=CCON=CCNC(=O)c1ccc(-c2noc(C(F)(F)F)n2)cc1] | 1.57 | 355.2 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.92 | 2-[2-[[2-[[4-[5-(trifluoromethyl)-1,2,4-oxadiazol-3-yl]benzoyl]amino]ethylideneamino]oxymethyl]phenyl]acetic acid | 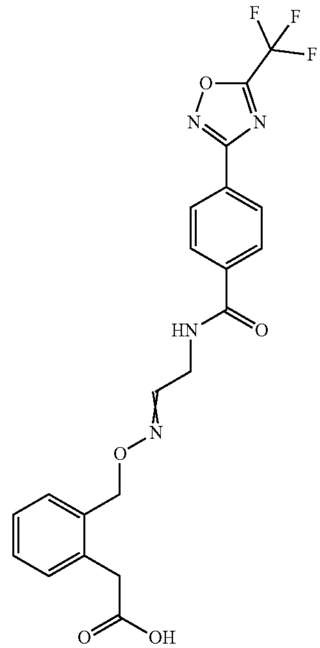 [SMILES: O=C(O)Cc1ccccc1CON=CCNC(=O)c1ccc(-c2noc(C(F)(F)F)n2)cc1] | 1.71 | 477.3 | B | |
| 1.93 | methyl 2-[2-[[2-[[4-[5-(trifluoromethyl)-1,2,4-oxadiazol-3-yl]benzoyl]amino]ethylideneamino]oxymethyl]phenyl]acetate | 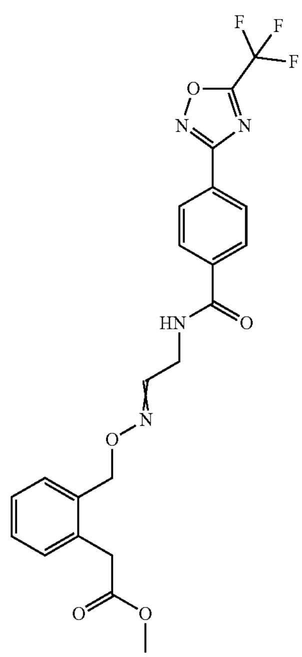 [SMILES: COC(=O)Cc1ccccc1CON=CCNC(=O)c1ccc(-c2noc(C(F)(F)F)n2)cc1] | 1.52 | 463.29 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.94 | N-(2-isopropoxyimino-ethyl)-4-[5-(trifluoromethyl)-1,2,4-oxadiazol-3-yl]benzamide | 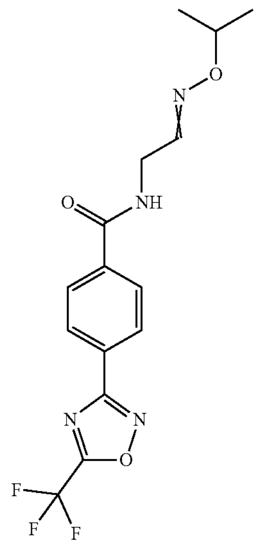 [SMILES: CC(C)ON=CCNC(=O)c1ccc(-c2noc(C(F)(F)F)n2)cc1] | 1.63 | 357.22 | B | |
| 1.95 | N-[2-(2,2,2-trifluoroethoxy-imino)ethyl]-4-[5-(trifluoromethyl)-1,2,4-oxadiazol-3-yl]benzamide | 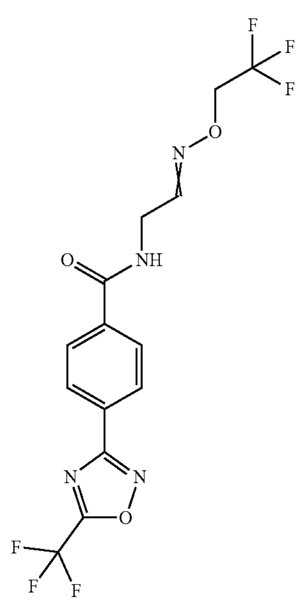 [SMILES: O=C(NCC=NOCC(F)(F)F)c1ccc(-c2noc(C(F)(F)F)n2)cc1] | 1.63 | 397.19 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.96 | N-[2-[(4-fluorophenyl)methoxyimino]ethyl]-4-[5-(trifluoromethyl)-1,2,4-oxadiazol-3-yl]benzamide | 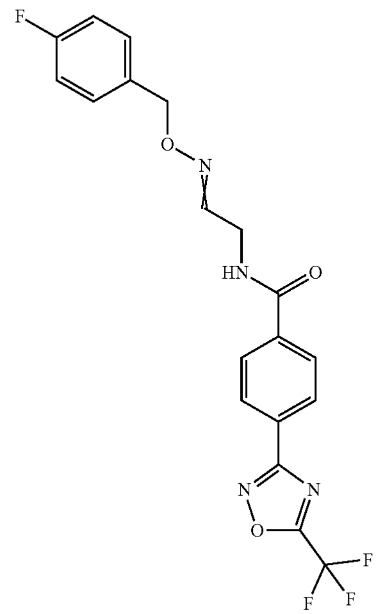 [SMILES: O=C(NCC=NOCc1ccc(F)cc1)c1ccc(-c2noc(C(F)(F)F)n2)cc1] | 1.75 | 423.24 | B | |
| 1.97 | N-[2-[(3-chlorophenyl)methoxyimino]ethyl]-4-[5-(trifluoromethyl)-1,2,4-oxadiazol-3-yl]benzamide | 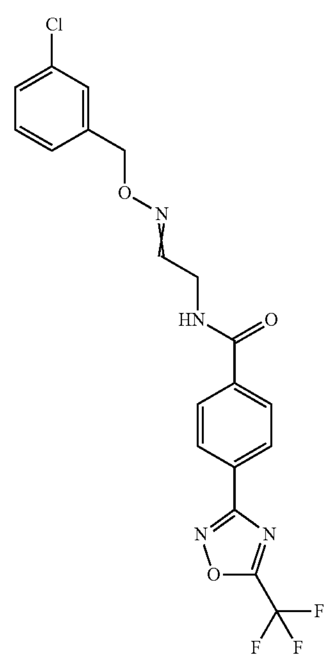 [SMILES: O=C(NCC=NOCc1cccc(Cl)c1)c1ccc(-c2noc(C(F)(F)F)n2)cc1] | 1.85 | 439.2 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.98 | 4-[5-(trifluoromethyl)-1,2,4-oxadiazol-3-yl]-N-[2-[[3-(trifluoromethyl)phenyl]methoxyimino]ethyl]benzamide | 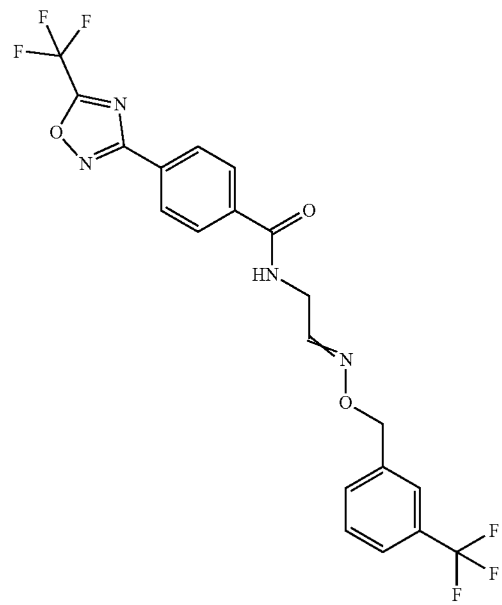 [SMILES: O=C(NCC=NOCc1cccc(C(F)(F)F)c1)c1ccc(-c2noc(C(F)(F)F)n2)cc1] | 1.89 | 473.25 | B | |
| 1.99 | 4-[5-(trifluoromethyl)-1,2,4-oxadiazol-3-yl]-N-[2-[[2-(trifluoromethyl)phenyl]methoxyimino]ethyl]benzamide | 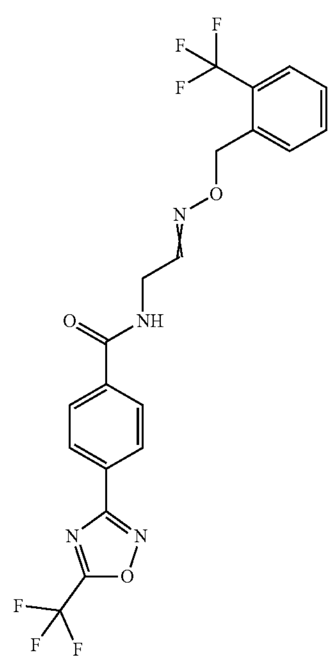 [SMILES: O=C(NCC=NOCc1ccccc1C(F)(F)F)c1ccc(-c2noc(C(F)(F)F)n2)cc1] | 1.9 | 473.25 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.100 | N-[2-(2-chloroallyloxy-imino)ethyl]-4-[5-(trifluoromethyl)-1,2,4-oxadiazol-3-yl]benzamide | 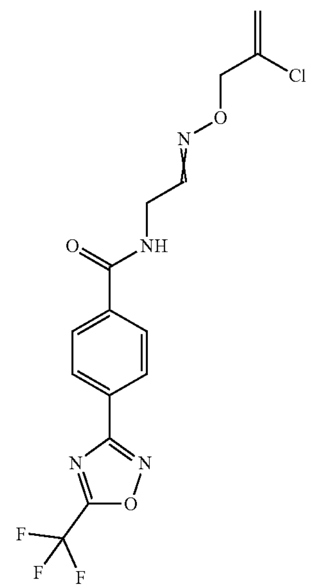 [SMILES: C=C(Cl)CON=CCNC(=O)c1ccc(-c2noc(C(F)(F)F)n2)cc1] | 1.66 | 389.17 | B | |
| 1.101 | N-[2-(cyclopropyl-methoxyimino)ethyl]-4-[5-(trifluoromethyl)-1,2,4-oxadiazol-3-yl]benzamide | 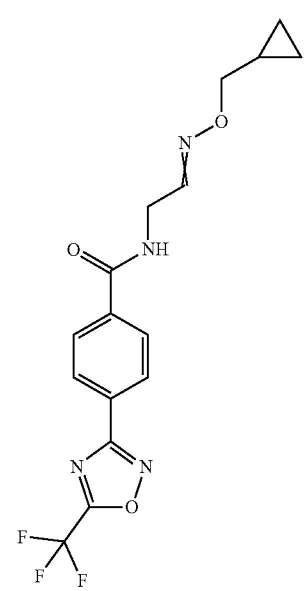 [SMILES: O=C(NCC=NOCC1CC1)c1ccc(-c2noc(C(F)(F)F)n2)cc1] | 1.64 | 369.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.102 | N-[2-(oxetan-3-yloxyimino)ethyl]-4-[5-(trifluoromethyl)-1,2,4-oxadiazol-3-yl]benzamide | 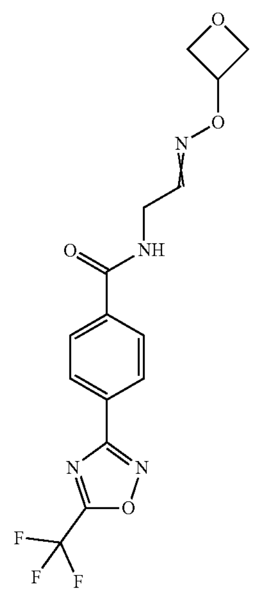 [SMILES: O=C(NCC=NOC1COC1)c1ccc(-c2noc(C(F)(F)F)n2)cc1] | 1.33 | 371.2 | B | |
| 1.103 | N-[2-[(4-chlorophenyl)methoxyimino]ethyl]-4-[5-(trifluoromethyl)-1,2,4-oxadiazol-3-yl]benzamide | 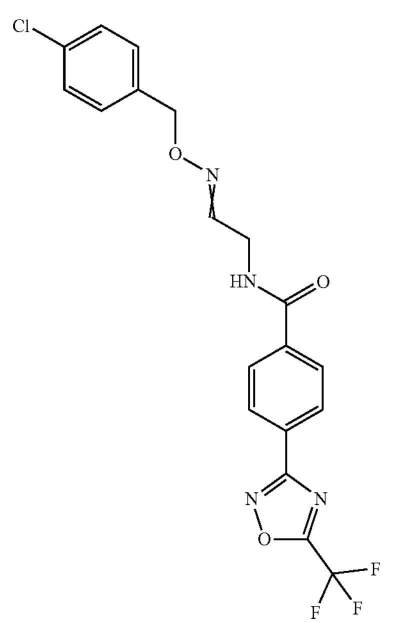 | 1.85 | 439.21 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.104 | N-[2-(2-hydroxyethoxy-imino)propoxy]-4-[5-(trifluoromethyl)-1,2,4-oxadiazol-3-yl]benzamide | 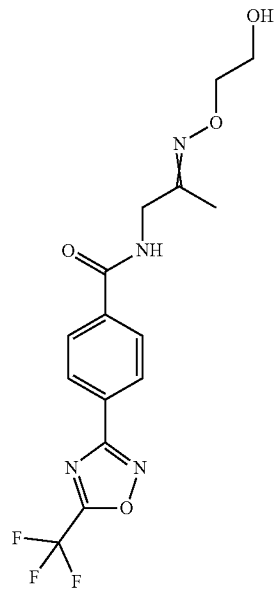 [SMILES: CC(CNC(=O)c1ccc(-c2noc(C(F)(F)F)n2)cc1)=NOCCO] | 1.26 | 373.21 | B | |
| 1.105 | N-[2-[(4-nitrophenyl)methoxyimino]propyl]-4-[5-(trifluoromethyl)-1,2,4-oxadiazol-3-yl]benzamide | 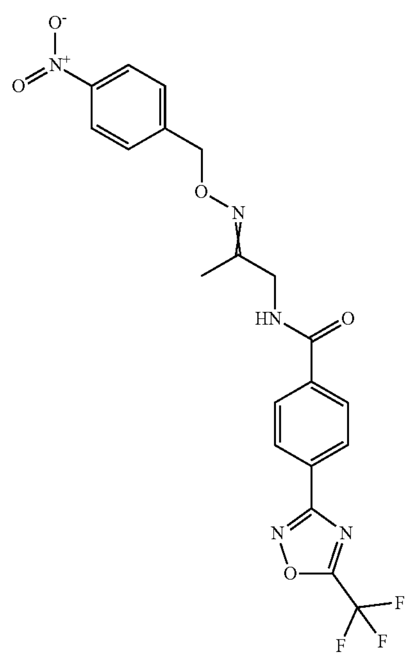 [SMILES: CC(CNC(=O)c1ccc(-c2noc(C(F)(F)F)n2)cc1)=NOCc1ccc([N+](=O)[O-])cc1] | 1.78 | 464.26 | B | |

TABLE T1-continued
Melting point (mp) and/or LC/MS data for compounds for Formula (I):
| Entry | Compound name | Structure | R$_t$ (min) | [M + H] (measured) | Method | mp (° C.) |
|---|---|---|---|---|---|---|
| 1.106 | N-[2-[(3-methoxyphenyl)methoxyimino]propyl]-4-[5-(trifluoromethyl)-1,2,4-oxadiazol-3-yl]benzamide | 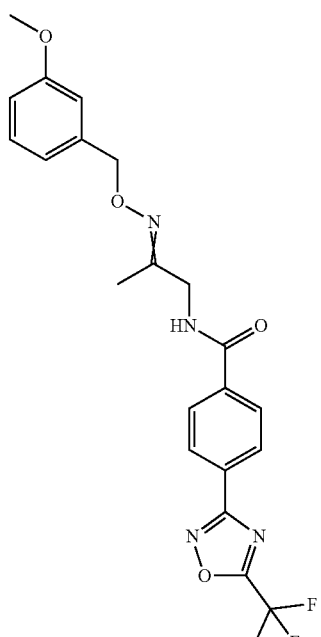 | 1.81 | 449.28 | B | |
| 1.107 | N-[2-(p-tolylmethoxyimino)propyl]-4-[5-(trifluoromethyl)-1,2,4-oxadiazol-3-yl]benzamide | 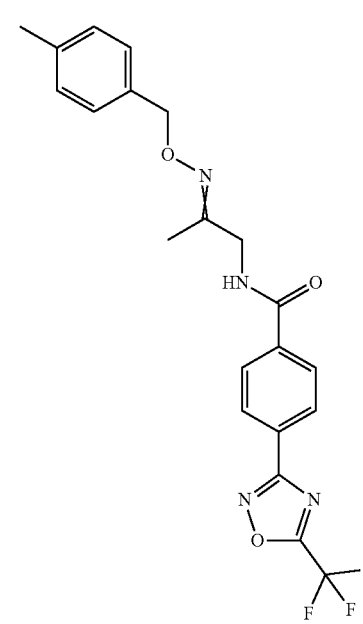 | 1.91 | 433.27 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.108 | N-[2-[(4-methoxyphenyl)methoxyimino]propyl]-4-[5-(trifluoromethyl)-1,2,4-oxadiazol-3-yl]benzamide | 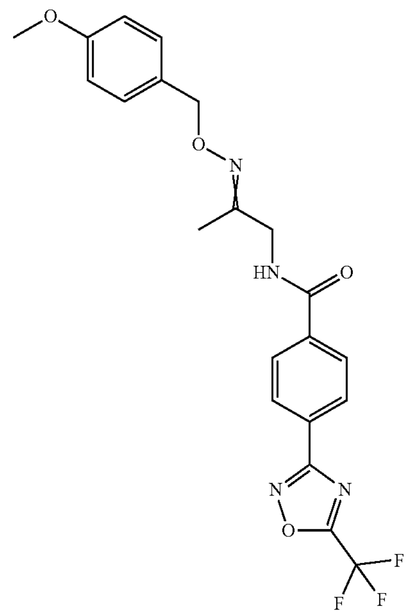 [SMILES: COc1ccc(CON=C(C)CNC(=O)c2ccc(-c3noc(C(F)(F)F)n3)cc2)cc1] | 1.79 | 449.28 | B | |
| 1.109 | 2-[[1-methyl-2-[[4-[5-(trifluoromethyl)-1,2,4-oxadiazol-3-yl]benzoyl]amino]ethylidene]amino]oxyacetic acid | 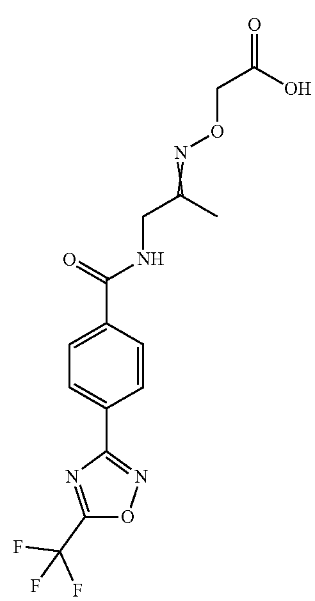 [SMILES: CC(CNC(=O)c1ccc(-c2noc(C(F)(F)F)n2)cc1)=NOCC(=O)O] | 1.27 | 387.19 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.110 | N-[2-(2-aminoethoxy-imino)propyl]-4-[5-(trifluoromethyl)-1,2,4-oxadiazol-3-yl]benzamide | 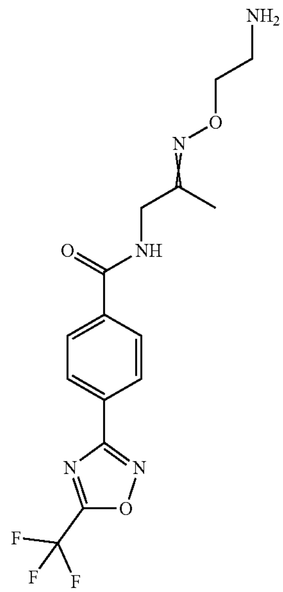 [SMILES: CC(CNC(=O)c1ccc(-c2noc(C(F)(F)F)n2)cc1)=NOCCN] | 0.89 | 372.25 | B | |
| 1.111 | N-[2-[(2-chlorophenyl)methoxyimino]propyl]-4-[5-(trifluoromethyl)-1,2,4-oxadiazol-3-yl]benzamide | 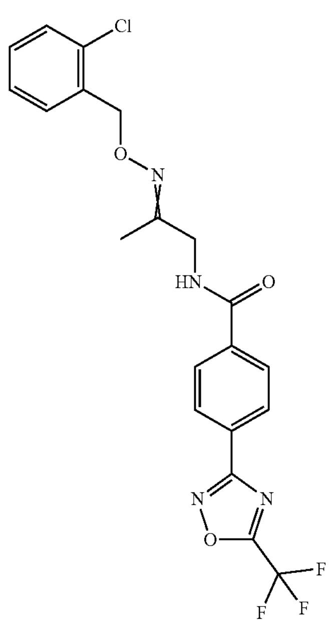 [SMILES: CC(CNC(=O)c1ccc(-c2noc(C(F)(F)F)n2)cc1)=NOCc1ccccc1Cl] | 1.93 | 453.22 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.112 | N-[2-[(2-methoxyphenyl)methoxyimino]propyl]-4-[5-(trifluoromethyl)-1,2,4-oxadiazol-3-yl]benzamide | 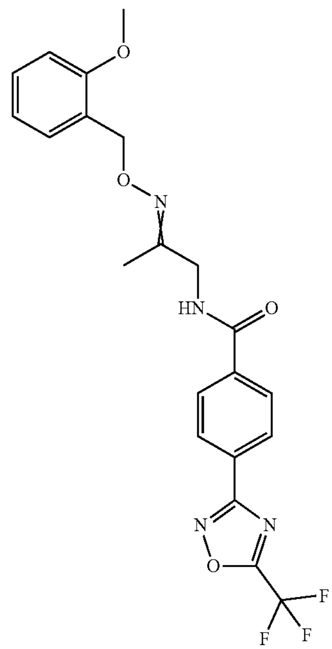 [SMILES: COc1ccccc1CON=C(C)CNC(=O)c1ccc(-c2noc(C(F)(F)F)n2)cc1] | 1.8 | 449.27 | B | |
| 1.113 | N-[2-[(2-fluorophenyl)methoxyimino]propyl]-4-[5-(trifluoromethyl)-1,2,4-oxadiazol-3-yl]benzamide | 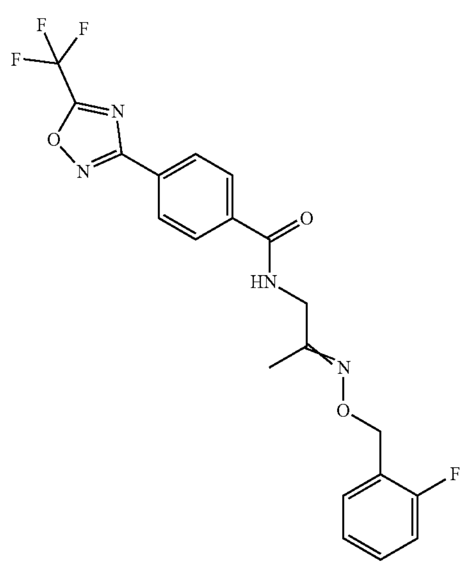 [SMILES: CC(CNC(=O)c1ccc(-c2noc(C(F)(F)F)n2)cc1)=NOCc1ccccc1F] | 1.84 | 437.24 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.114 | N-(2-tetrahydropyran-2-yloxyiminopropyl)-4-[5-(trifluoromethyl)-1,2,4-oxadiazol-3-yl]benzamide | 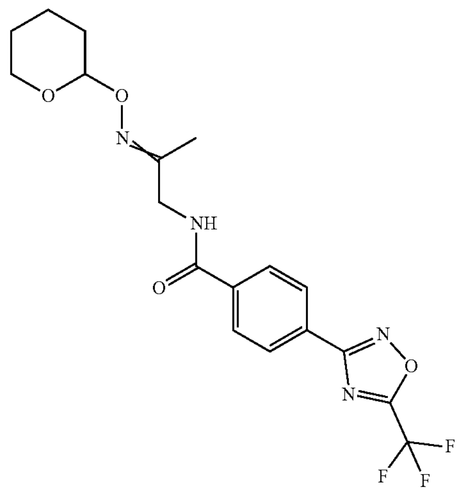 [SMILES: CC(CNC(=O)c1ccc(-c2noc(C(F)(F)F)n2)cc1)=NOC1CCCCO1] | 1.65 | 413.27 | B | |
| 1.115 | N-[2-[(2-chloro-4-fluorophenyl)methoxyimino]propyl]-4-[5-(trifluoromethyl)-1,2,4-oxadiazol-3-yl]benzamide | 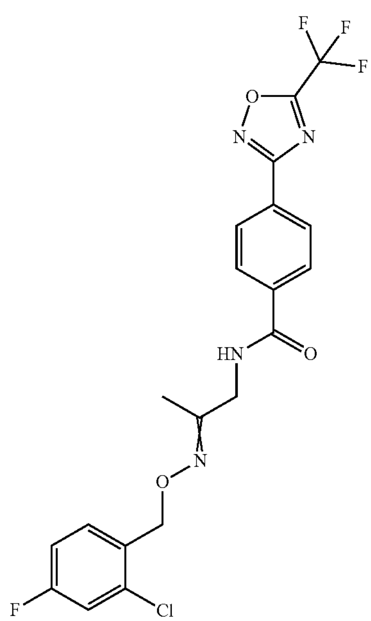 [SMILES: CC(CNC(=O)c1ccc(-c2noc(C(F)(F)F)n2)cc1)=NOCc1ccc(F)cc1Cl] | 1.96 | 471.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.116 | N-(2-propoxyimino-propyl)-4-[5-(trifluoromethyl)-1,2,4-oxadiazol-3-yl]benzamide | 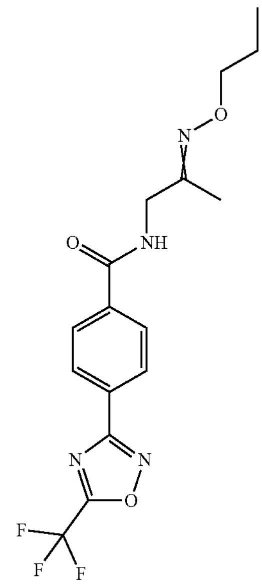 [SMILES: CCCON=C(C)CNC(=O)c1ccc(-c2noc(C(F)(F)F)n2)cc1] | 1.74 | 371.22 | B | |
| 1.117 | (2R)-2-[[1-methyl-2-[[4-[5-(trifluoromethyl)-1,2,4-oxadiazol-3-yl]benzoyl]amino]ethylidene]amino]oxypropanoic acid | 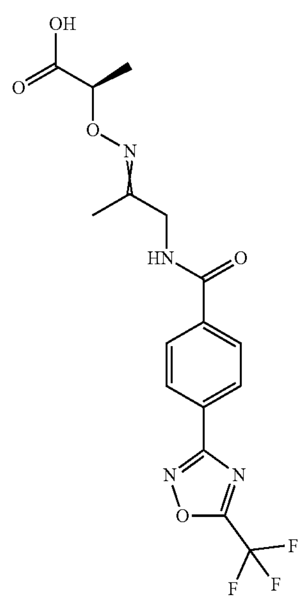 [SMILES: CC(CNC(=O)c1ccc(-c2noc(C(F)(F)F)n2)cc1)=NO[C@H](C)C(=O)O] | 1.67 | 429.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.118 | ethyl (2R)-2-[[1-methyl-2-[[4-[5-(trifluoromethyl)-1,2,4-oxadiazol-3-yl]benzoyl]amino]ethylidene]amino]oxypropanoate | 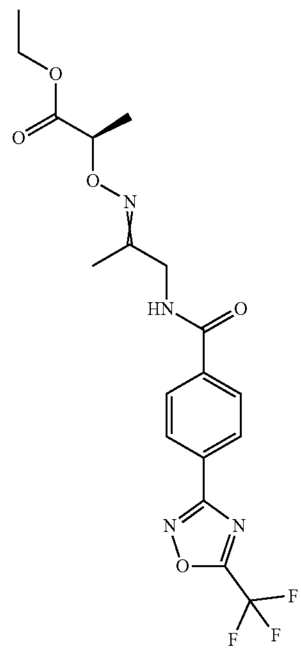 [SMILES: CCOC(=O)[C@@H](C)ON=C(C)CNC(=O)c1ccc(-c2noc(C(F)(F)F)n2)cc1] | 1.36 | 401.2 | B | |
| 1.119 | N-[2-[(4-bromophenyl)methoxyimino]propyl]-4-[5-(trifluoromethyl)-1,2,4-oxadiazol-3-yl]benzamide | 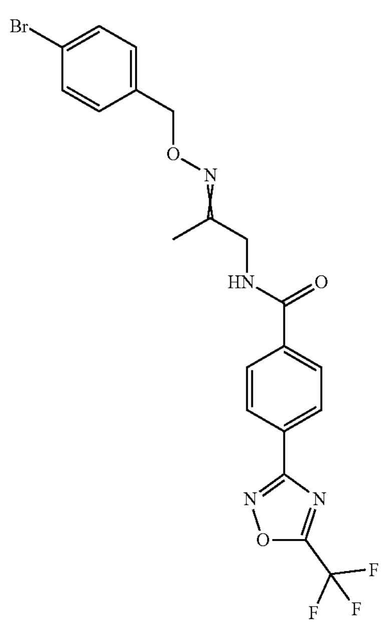 | 1.96 | 497.18 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.120 | (2S)-2-[[1-methyl-2-[[4-[5-(trifluoromethyl)-1,2,4-oxadiazol-3-yl]benzoyl]amino]ethylidene]amino]oxypropanoic acid | 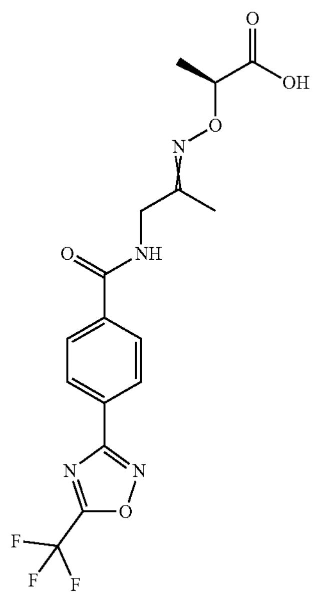 [SMILES: CC(CNC(=O)c1ccc(-c2noc(C(F)(F)F)n2)cc1)=NO[C@@H](C)C(=O)O] | 1.36 | 401.22 | B | |
| 1.121 | N-[2-(3-chloroallyloxy-imino)propyl]-4-[5-(trifluoromethyl)-1,2,4-oxadiazol-3-yl]benzamide | 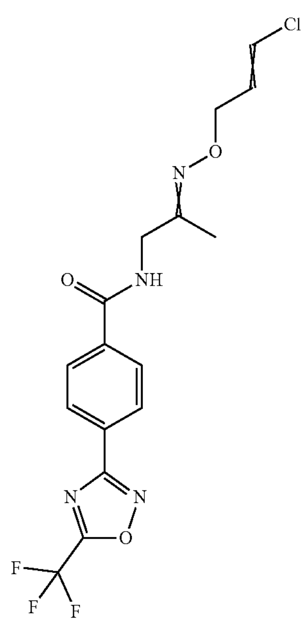 [SMILES: CC(CNC(=O)c1ccc(-c2noc(C(F)(F)F)n2)cc1)=NOCC=CCl] | 1.74 | 403.2 | B | |

TABLE T1-continued
Melting point (mp) and/or LC/MS data for compounds for Formula (I):
| Entry | Compound name | Structure | R$_t$ (min) | [M + H] (measured) | Method | mp (° C.) |
|---|---|---|---|---|---|---|
| 1.122 | N-[2-(3,3-dichloroallyloxy-imino)propyl]-4-[5-(trifluoromethyl)-1,2,4-oxadiazol-3-yl]benzamide | 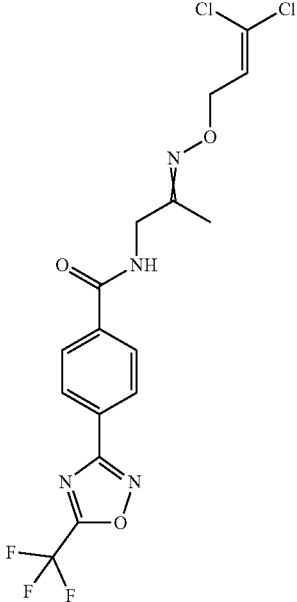 [SMILES: CC(CNC(=O)c1ccc(-c2noc(C(F)(F)F)n2)cc1)=NOCC=C(Cl)Cl] | 1.88 | 437.17 | B | |
| 1.123 | N-[2-(3-methylbut-2-enoxyimino)propyl]-4-[5-(trifluoromethyl)-1,2,4-oxadiazol-3-yl]benzamide | 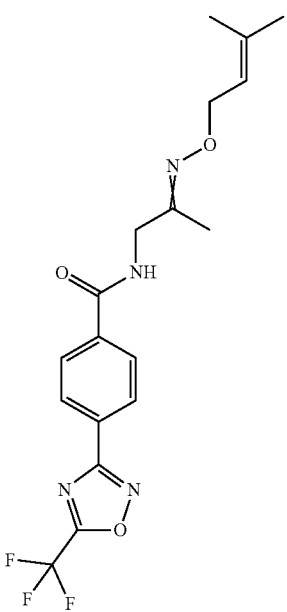 [SMILES: CC(C)=CCON=C(C)CNC(=O)c1ccc(-c2noc(C(F)(F)F)n2)cc1] | 1.84 | 397.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.124 | N-[2-[(Z)-3-chloroallyloxy]iminopropyl]-4-[5-(trifluoromethyl)-1,2,4-oxadiazol-3-yl]benzamide | 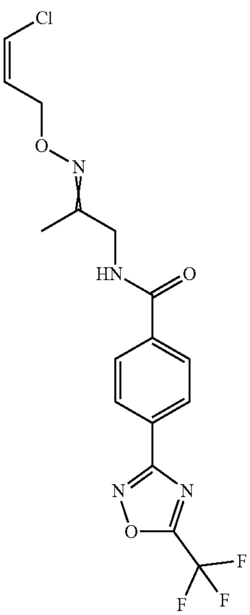 [SMILES: CC(CNC(=O)c1ccc(-c2noc(C(F)(F)F)n2)cc1)=NOC/C=C\Cl] | 1.74 | 403.19 | B | |
| 1.125 | 2-[[1-methyl-2-[[4-[5-(trifluoromethyl)-1,2,4-oxadiazol-3-yl]benzoyl]amino]ethylidene]aminooxypropanoic acid | 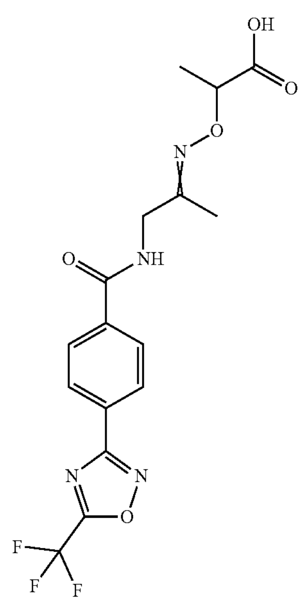 [SMILES: CC(CNC(=O)c1ccc(-c2noc(C(F)(F)F)n2)cc1)=NOC(C)C(=O)O] | 1.66 | 429.26 | B | |

TABLE T1-continued

Melting point (mp) and/or LC/MS data for compounds for Formula (I):

| Entry | Compound name | Structure | R_t (min) | [M + H] (measured) | Method | mp (° C.) |
|---|---|---|---|---|---|---|
| 1.126 | ethyl 2-[[1-methyl-2-[[4-[5-(trifluoromethyl)-1,2,4-oxadiazol-3-yl]benzoyl]amino]ethylidene]amino]oxypropanoate | 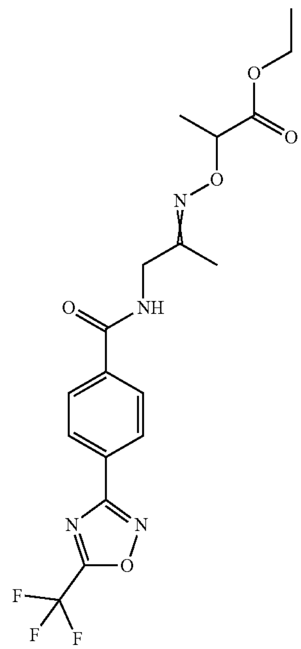 [SMILES: CCOC(=O)C(C)ON=C(C)CNC(=O)c1ccc(-c2noc(C(F)(F)F)n2)cc1] | 1.36 | 401.22 | B | |
| 1.127 | N-[2-[(2,6-dichorophenyl)methoxyimino]propyl]-4-[5-(trifluoromethyl)-1,2,4-oxadiazol-3-yl]benzamide | 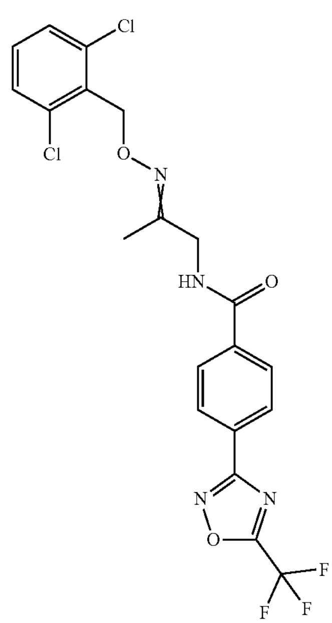 [SMILES: CC(CNC(=O)c1ccc(-c2noc(C(F)(F)F)n2)cc1)=NOCc1c(Cl)cccc1Cl] | 2.01 | 487.19 | B | |

TABLE T1-continued
Melting point (mp) and/or LC/MS data for compounds for Formula (I):
| Entry | Compound name | Structure | R$_t$ (min) | [M + H] (measured) | Method | mp (° C.) |
|---|---|---|---|---|---|---|
| 1.128 | N-(2-butoxyiminopropyl)-4-[5-(trifluoromethyl)-1,2,4-oxadiazol-3-yl]benzamide | 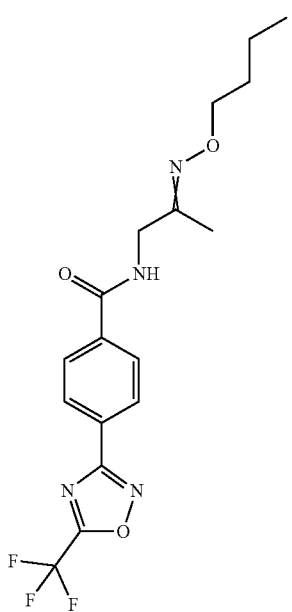 [SMILES: CCCCON=C(C)CNC(=O)c1ccc(-c2noc(C(F)(F)F)n2)cc1] | 1.85 | 385.24 | B | |
| 1.129 | N-(2-hexoxyiminopropyl)-4-[5-(trifluoromethyl)-1,2,4-oxadiazol-3-yl]benzamide | 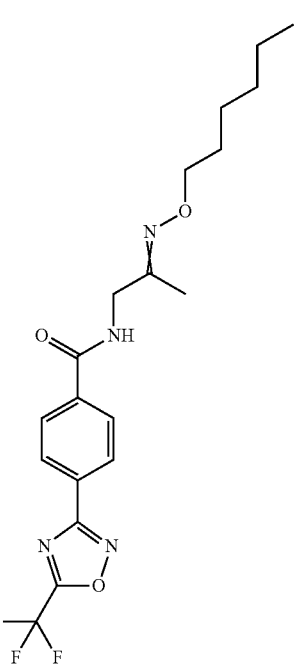 | 2.06 | 413.29 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.130 | N-[2-[(2,3,4,5,6-pentafluorophenyl)methoxyimino]propyl]-4-[5-(trifluoromethyl)-1,2,4-oxadiazol-3-yl]benzamide | 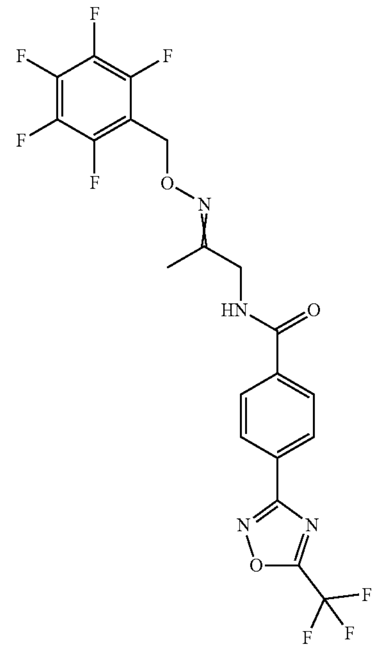 [SMILES: CC(CNC(=O)c1ccc(-c2noc(C(F)(F)F)n2)cc1)=NOCc1c(F)c(F)c(F)c(F)c1F] | 1.95 | 509.22 | B | |
| 1.131 | N-[2-[(2,4,5-trichlorophenyl)methoxyimino]propyl]-4-[5-(trifluoromethyl)-1,2,4-oxadiazol-3-yl]benzamide | 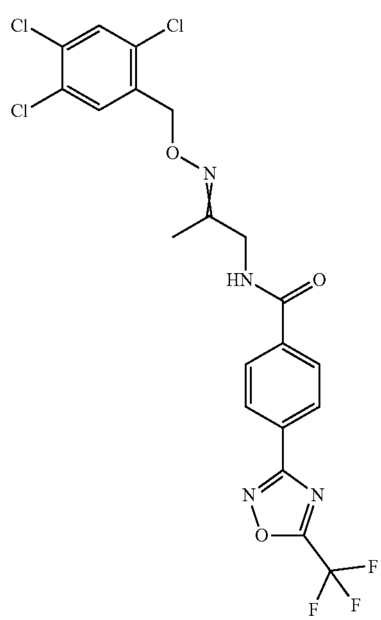 [SMILES: CC(CNC(=O)c1ccc(-c2noc(C(F)(F)F)n2)cc1)=NOCc1cc(Cl)c(Cl)cc1Cl] | 2.16 | 521.16 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.132 | N-(2-tert-butoxyiminopropyl)-4-[5-(trifluoromethyl)-1,2,4-oxadiazol-3-yl]benzamide | 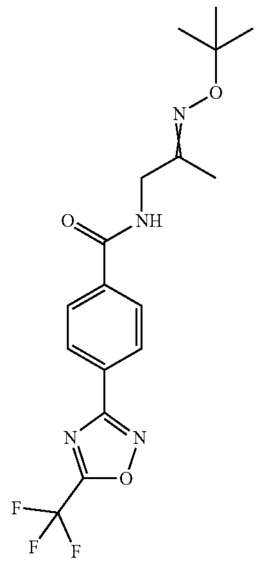 [SMILES: CC(CNC(=O)c1ccc(-c2noc(C(F)(F)F)n2)cc1)=NOC(C)(C)C] | 1.87 | 385.25 | B | |
| 1.133 | N-(2-methoxyimino-propyl)-4-[5-(trifluoromethyl)-1,2,4-oxadiazol-3-yl]benzamide | 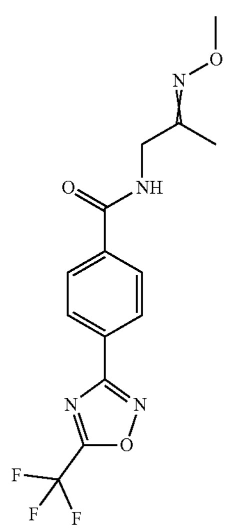 [SMILES: CON=C(C)CNC(=O)c1ccc(-c2noc(C(F)(F)F)n2)cc1] | 1.48 | 343.19 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.134 | N-(2-benzyloxyimino-propyl)-4-[5-(trifluoromethyl)-1,2,4-oxadiazol-3-yl]benzamide | 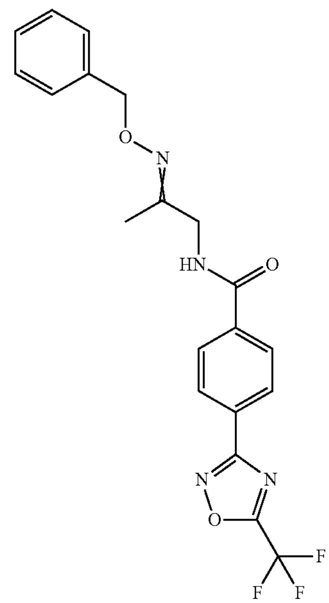 [SMILES: CC(CNC(=O)c1ccc(-c2noc(C(F)(F)F)n2)cc1)=NOCc1ccccc1] | 1.82 | 419.24 | B | |
| 1.135 | N-(2-allyloxyimino-propyl)-4-[5-(trifluoromethyl)-1,2,4-oxadiazol-3-yl]benzamide | 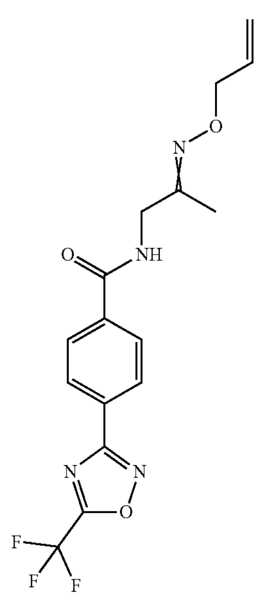 [SMILES: C=CCON=C(C)CNC(=O)c1ccc(-c2noc(C(F)(F)F)n2)cc1] | 1.65 | 369.21 | B | |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.136 | 2-[2-[[[1-methyl-2-[[4-[5-(trifluoromethyl)-1,2,4-oxadiazol-3-yl]benzoyl]amino]ethylidene]amino]oxymethyl]phenyl]acetic acid | 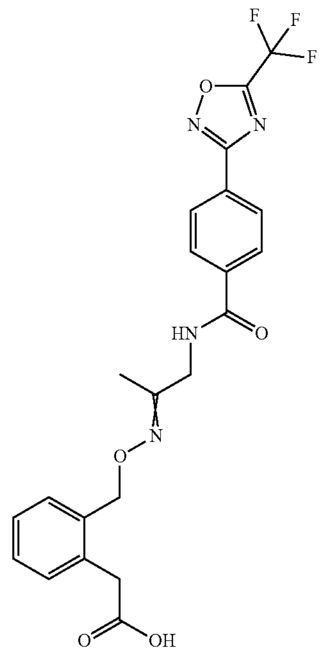 [SMILES: CC(CNC(=O)c1ccc(-c2noc(C(F)(F)F)n2)cc1)=NOCc1ccccc1CC(=O)O] | 1.77 | 491.3 | B | |
| 1.137 | methyl 2-[2-[[[1-methyl-2-[[4-[5-(trifluoromethyl)-1,2,4-oxadiazol-3-yl]benzoyl]amino]ethylidene]amino]oxymethyl]phenyl]acetate | 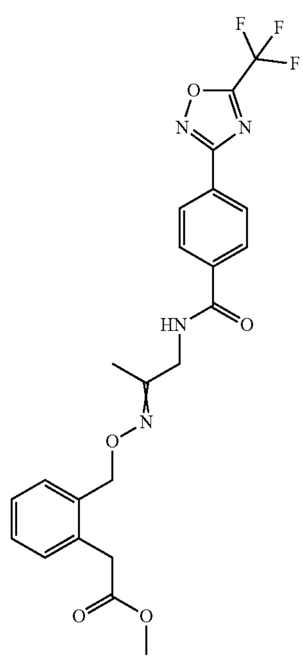 [SMILES: COC(=O)Cc1ccccc1CON=C(C)CNC(=O)c1ccc(-c2noc(C(F)(F)F)n2)cc1] | 1.57 | 477.26 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.138 | N-(2-isopropoxyimino-propyl)-4-[5-(trifluoromethyl)-1,2,4-oxadiazol-3-yl]benzamide | 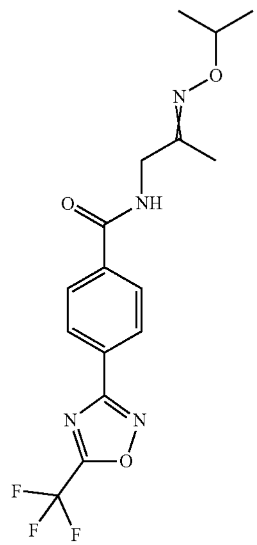 [SMILES: CC(CNC(=O)c1ccc(-c2noc(C(F)(F)F)n2)cc1)=NOC(C)C] | 1.73 | 371.23 | B | |
| 1.139 | N-[2-(2,2,2-trifluoroethoxy-imino)propyl]-4-[5-(trifluoromethyl)-1,2,4-oxadiazol-3-yl]benzamide | 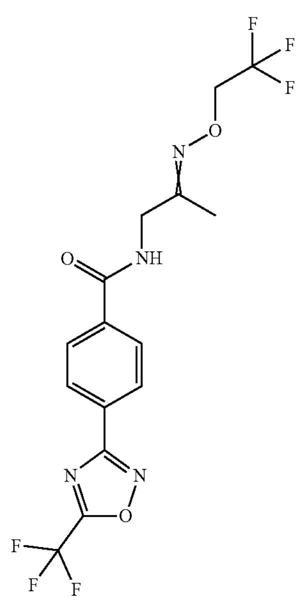 [SMILES: CC(CNC(=O)c1ccc(-c2noc(C(F)(F)F)n2)cc1)=NOCC(F)(F)F] | 1.69 | 411.2 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.140 | N-[2-[(4-fluorophenyl)methoxyimino]propyl]-4-[5-(trifluoromethyl)-1,2,4-oxadiazol-3-yl]benzamide | 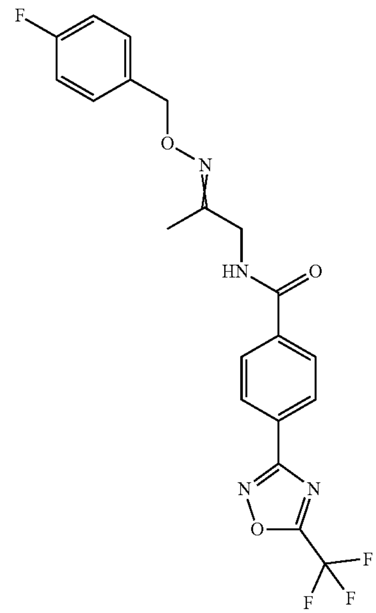 [SMILES: CC(CNC(=O)c1ccc(-c2noc(C(F)(F)F)n2)cc1)=NOCc1ccc(F)cc1] | 1.82 | 437.26 | B | |
| 1.141 | N-[2-[(3-chlorophenyl)methoxyimino]propyl]-4-[5-(trifluoromethyl)-1,2,4-oxadiazol-3-yl]benzamide | 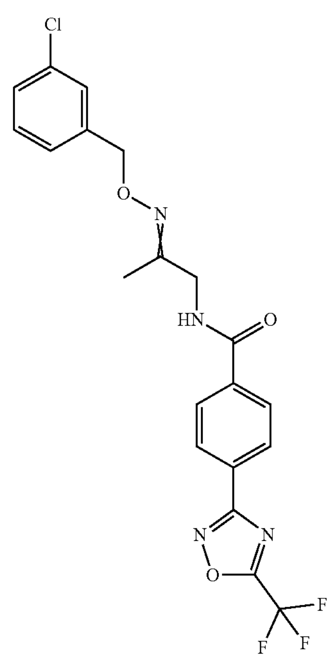 [SMILES: CC(CNC(=O)c1ccc(-c2noc(C(F)(F)F)n2)cc1)=NOCc1cccc(Cl)c1] | 1.93 | 453.22 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.142 | 4-[5-(trifluoromethyl)-1,2,4-oxadiazol-3-yl]-N-[2-[[3-(trifluoromethyl)phenyl]methoxyimino]propyl]benzamide | 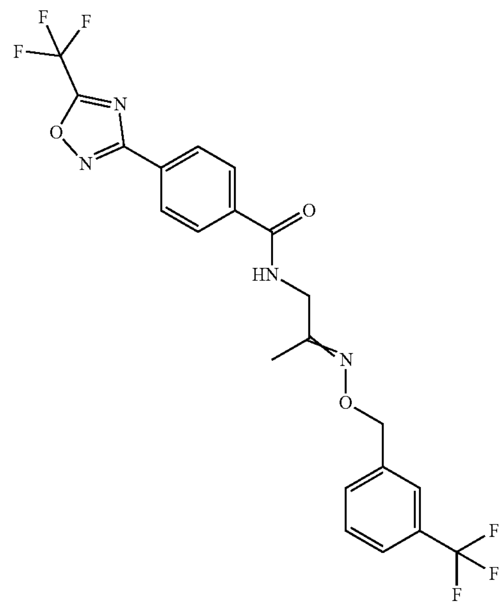 [SMILES: CC(CNC(=O)c1ccc(-c2noc(C(F)(F)F)n2)cc1)=NOCc1cccc(C(F)(F)F)c1] | 1.96 | 487.26 | B | |
| 1.143 | 4-[5-(trifluoromethyl)-1,2,4-oxadiazol-3-yl]-N-[2-[[2-(trifluoromethyl)phenyl]methoxyimino]propyl]benzamide | 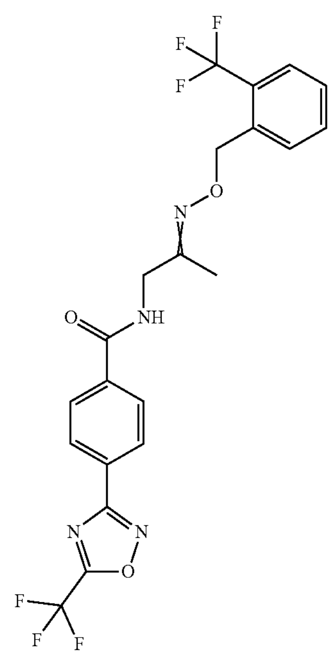 [SMILES: CC(CNC(=O)c1ccc(-c2noc(C(F)(F)F)n2)cc1)=NOCc1ccccc1C(F)(F)F] | 1.97 | 487.26 | B | |

TABLE T1-continued

Melting point (mp) and/or LC/MS data for compounds for Formula (I):

| Entry | Compound name | Structure | R_t (min) | [M + H] (measured) | Method | mp (° C.) |
|---|---|---|---|---|---|---|
| 1.144 | N-[2-(2-chloroallyloxy-imino)propyl]-4-[5-(trifluoromethyl)-1,2,4-oxadiazol-3-yl]benzamide | 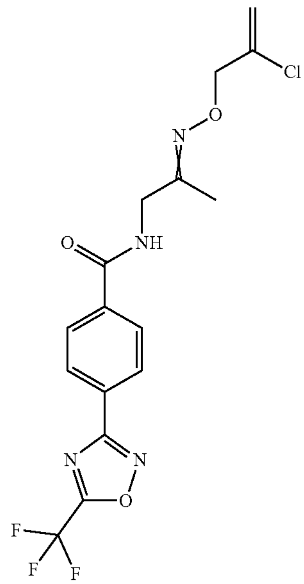 | 1.75 | 403.19 | B | |
| 1.145 | N-[2-(cyclopropyl-methoxyimino)propyl]-4-[5-(trifluoromethyl)-1,2,4-oxadiazol-3-yl]benzamide | 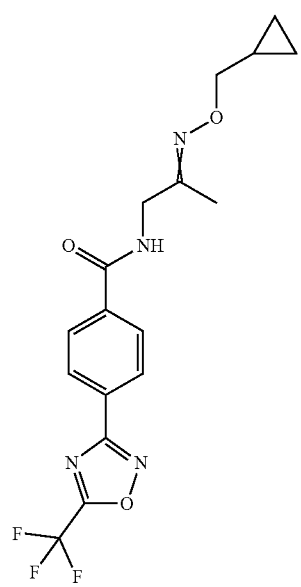 [SMILES: CC(CNC(=O)c1ccc(-c2noc(C(F)(F)F)n2)cc1)=NOCC1CC1] | 1.72 | 383.23 | B | |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.146 | N-[2-(oxetan-3-yloxyimino)propyl]-4-[5-(trifluoromethyl)-1,2,4-oxadiazol-3-yl]benzamide | 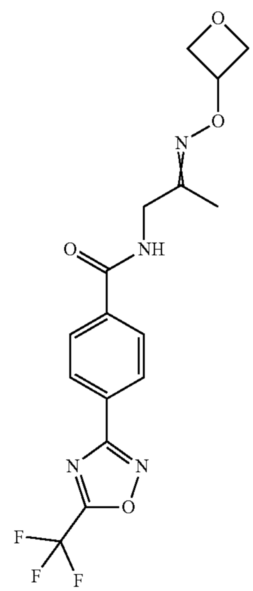 [SMILES: CC(CNC(=O)c1ccc(-c2noc(C(F)(F)F)n2)cc1)=NOC1COC1] | 1.4 | 385.21 | B | |
| 1.147 | N-[2-[(4-chlorophenyl)methoxyimino]propyl]-4-[5-(trifluoromethyl)-1,2,4-oxadiazol-3-yl]benzamide | 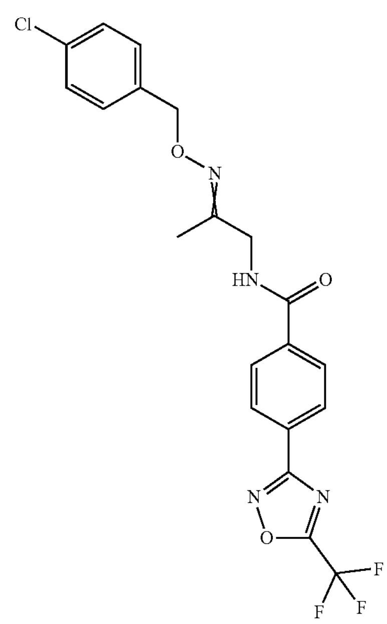 [SMILES: CC(CNC(=O)c1ccc(-c2noc(C(F)(F)F)n2)cc1)=NOCc1ccc(Cl)cc1] | 1.93 | 453.21 | B | |
| 1.148 | N-[2-(2-fluoroethoxyimino)ethyl]-4-[5-(trifluoromethyl)-1,2,4-oxadiazol-3-yl]benzamide | 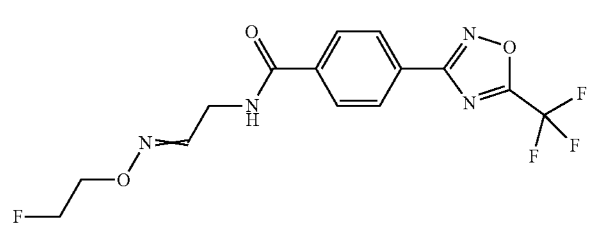 [SMILES: O=C(NCC=NOCCF)c1ccc(-c2noc(C(F)(F)F)n2)cc1] | | | | 145-146 |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.149 | N-[(2E)-2-(2-fluoroethoxy-imino)-1-methyl-ethyl]-4-[5-(trifluoromethyl)-1,2,4-oxadiazol-3-yl]benzamide | 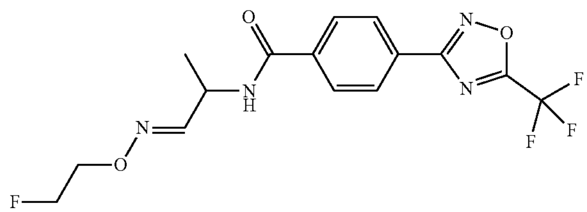 [SMILES: CC(/C=N/OCCF)NC(=O)c1ccc(-c2noc(C(F)(F)F)n2)cc1] | | | | 138-139 |
| 1.150 | N-[(2Z)-2-(2-fluoroethoxyimino)-1-methyl-ethyl]-4-[5-(trifluoromethyl)-1,2,4-oxadiazol-3-yl]benzamide | 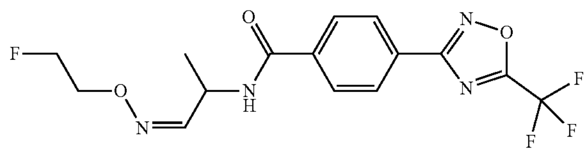 [SMILES: CC(/C=N\OCCF)NC(=O)c1ccc(-c2noc(C(F)(F)F)n2)cc1] | | | | 172-173 |
| 1.151 | N-[2-(2-fluoroethoxyimino)propyl]-4-[5-(trifluoromethyl)-1,2,4-oxadiazol-3-yl]benzamide | 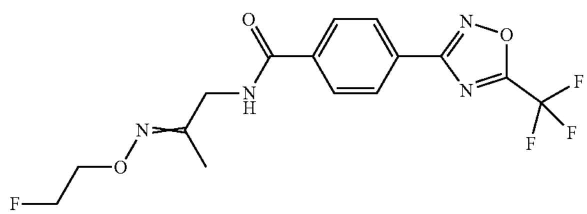 [SMILES: CC(CNC(=O)c1ccc(-c2noc(C(F)(F)F)n2)cc1)=NOCCF] | | | | 133-134 |
| 1.152 | N-(3-methoxyimino-propyl)-4-[5-(trifluoromethyl)-1,2,4-oxadiazol-3-yl]benzamide | 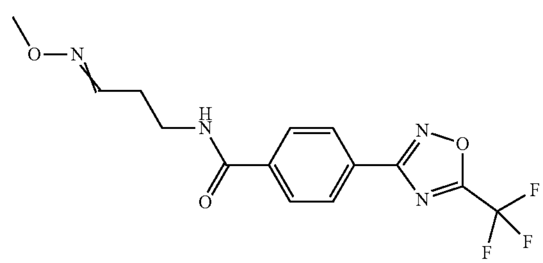 [SMILES: CON=CCCNC(=O)c1ccc(-c2noc(C(F)(F)F)n2)cc1] | | | | 136-140 |
| 1.153 | N-(3-ethoxyiminopropyl)-4-[5-(trifluoromethyl)-1,2,4-oxadiazol-3-yl]benzamide | 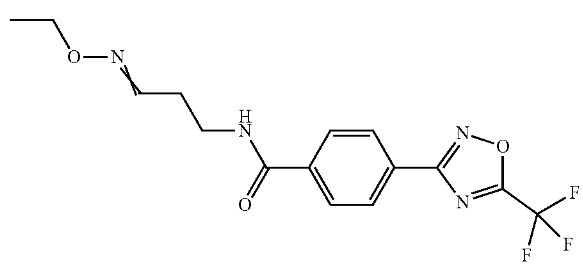 [SMILES: CCON=CCCNC(=O)c1ccc(-c2noc(C(F)(F)F)n2)cc1] | | | | 132-136 |
| 1.154 | N-(3-hydroxyimino-propyl)-4-[5-(trifluoromethyl)-1,2,4-oxadiazol-3-yl]benzamide | 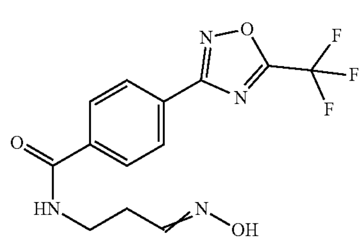 [SMILES: O=C(NCCC=NO)c1ccc(-c2noc(C(F)(F)F)n2)cc1] | | | | 180-183 |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.155 | 2-fluoro-N-(2-methoxyimino-1-methyl-ethyl)-4-[5-(trifluoromethyl)-1,2,4-oxadiazol-3-yl]benzamide | 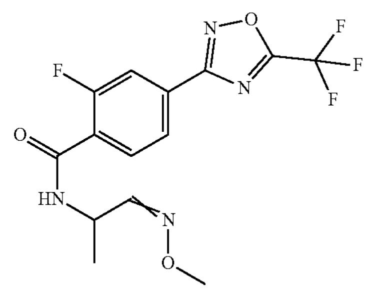 [SMILES: CON=CC(C)NC(=O)c1ccc(-c2noc(C(F)(F)F)n2)cc1F] | | | | 132-134 |
| 1.156 | N-(2-ethoxyimino-1-methyl-ethyl)-2-fluoro-4-[5-(trifluoromethyl)-1,2,4-oxadiazol-3-yl]benzamide | 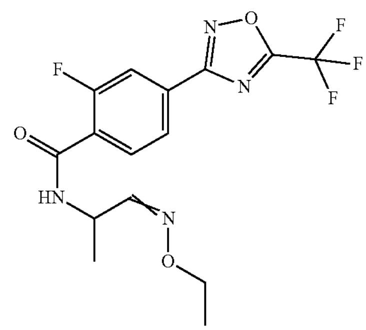 [SMILES: CCON=CC(C)NC(=O)c1ccc(-c2noc(C(F)(F)F)n2)cc1F] | | | | 113-115 |
| 1.157 | 2-fluoro-N-(2-methoxyimino-propyl)-4-[5-(trifluoromethyl)-1,2,4-oxadiazol-3-yl]benzamide | 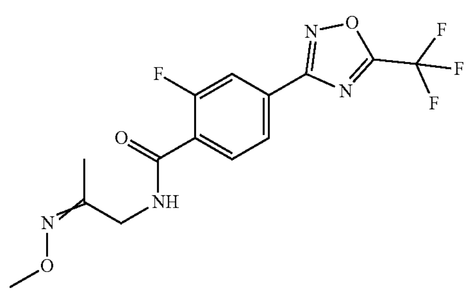 [SMILES: CON=C(C)CNC(=O)c1ccc(-c2noc(C(F)(F)F)n2)cc1F] | | | | 122-124 |
| 1.158 | N-(2-ethoxyiminopropyl)-2-fluoro-4-[5-(trifluoromethyl)-1,2,4-oxadiazol-3-yl]benzamide | 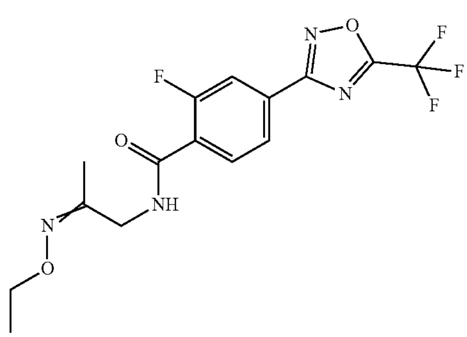 [SMILES: CCON=C(C)CNC(=O)c1ccc(-c2noc(C(F)(F)F)n2)cc1F] | | | | 120-122 |
| 1.159 | 3-fluoro-N-(2-methoxyimino-1-methyl-ethyl)-4-[5-(trifluoromethyl)-1,2,4-oxadiazol-3-yl]benzamide | 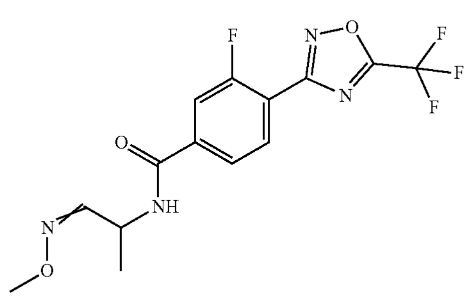 [SMILES: CON=CC(C)NC(=O)c1ccc(-c2noc(C(F)(F)F)n2)c(F)c1] | | | | 119-121 |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.160 | 3-fluoro-N-(3-methoxyiminopropyl)-4-[5-(trifluoromethyl)-1,2,4-oxadiazol-3-yl]benzamide | 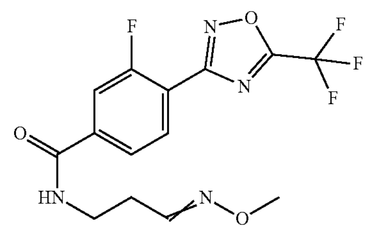 [SMILES: CON=CCCNC(=O)c1ccc(-c2noc(C(F)(F)F)n2)c(F)c1] | | | | 103-108 |
| 1.161 | N-(3-ethoxyiminopropyl)-3-fluoro-4-[5-(trifluoromethyl)-1,2,4-oxadiazol-3-yl]benzamide | 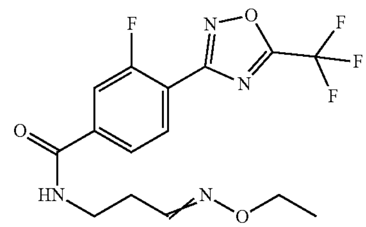 [SMILES: CCON=CCCNC(=O)c1ccc(-c2noc(C(F)(F)F)n2)c(F)c1] | | | | 108-110 |
| 1.162 | N-(3-ethoxyiminopropyl)-2-fluoro-4-[5-(trifluoromethyl)-1,2,4-oxadiazol-3-yl]benzamide | 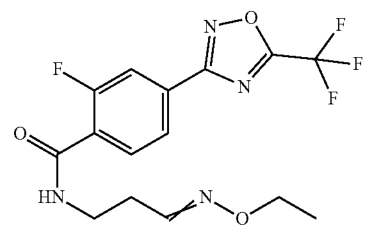 [SMILES: CCON=CCCNC(=O)c1ccc(-c2noc(C(F)(F)F)n2)cc1F] | | | | 97-99 |
| 1.163 | 2-fluoro-N-(3-methoxyiminopropyl)-4-[5-(trifluoromethyl)-1,2,4-oxadiazol-3-yl]benzamide | 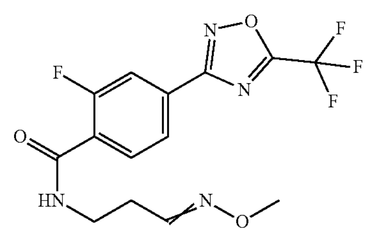 [SMILES: CON=CCCNC(=O)c1ccc(-c2noc(C(F)(F)F)n2)cc1F] | | | | 98-100 |
| 1.164 | 3-fluoro-N-(2-methoxyiminopropyl)-4-[5-(trifluoromethyl)-1,2,4-oxadiazol-3-yl]benzamide | 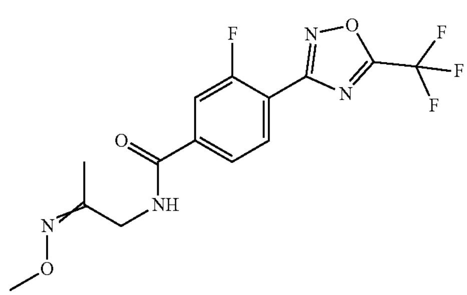 [SMILES: CON=C(C)CNC(=O)c1ccc(-c2noc(C(F)(F)F)n2)c(F)c1] | | | | 131-134 |
| 1.165 | N-(2-ethoxyiminopropyl)-3-fluoro-4-[5-(trifluoromethyl)-1,2,4-oxadiazol-3-yl]benzamide | 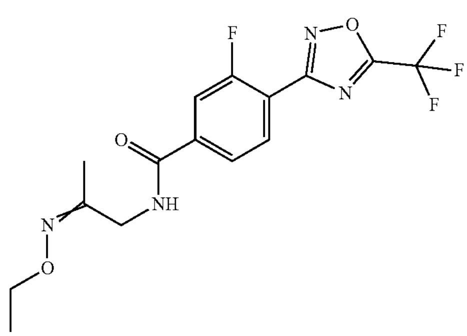 [SMILES: CCON=C(C)CNC(=O)c1ccc(-c2noc(C(F)(F)F)n2)c(F)c1] | | | | 120-124 |

TABLE T1-continued

Melting point (mp) and/or LC/MS data for compounds for Formula (I):

| Entry | Compound name | Structure | R$_t$ (min) | [M + H] (measured) | Method | mp (° C.) |
|---|---|---|---|---|---|---|
| 1.166 | 3-fluoro-N-(2-methoxyimino-ethyl)-4-[5-(trifluoromethyl)-1,2,4-oxadiazol-3-yl]benzamide | 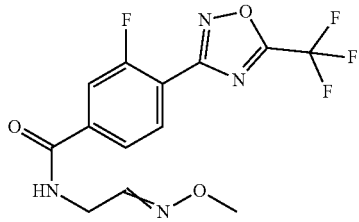 [SMILES: CON=CCNC(=O)c1ccc(-c2noc(C(F)(F)F)n2)c(F)c1] | | | | 120-122 |
| 1.167 | N-[(3E)-3-prop-2-ynoxyiminopropyl]-4-[5-(trifluoromethyl)-1,2,4-oxadiazol-3-yl]benzamide | 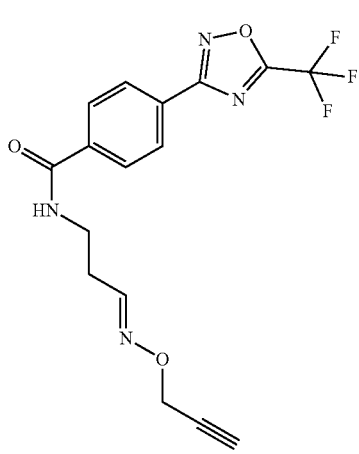 [SMILES: C#CCO/N=C/CCNC(=O)c1ccc(-c2noc(C(F)(F)F)n2)cc1] | | | | 89-91 |
| 1.168 | N-(3-isopropoxyimino-propyl)-4-[5-(trifluoromethyl)-1,2,4-oxadiazol-3-yl]benzamide | 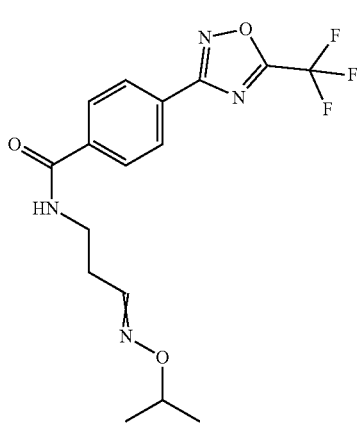 [SMILES: CC(C)ON=CCCNC(=O)c1ccc(-c2noc(C(F)(F)F)n2)cc1] | 1.527 | 370.9 | C | 122-124 |
| 1.169 | 2-fluoro-N-(2-methoxyimino-ethyl)-4-[5-(trifluoromethyl)-1,2,4-oxadiazol-3-yl]benzamide | 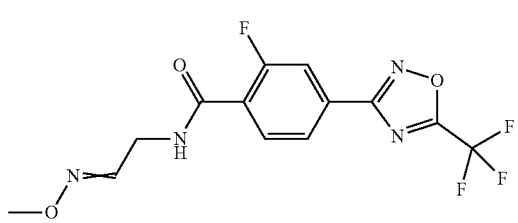 [SMILES: CON=CCNC(=O)c1ccc(-c2noc(C(F)(F)F)n2)cc1F] | 1.460 | 346.8 | C | 116-118 |

TABLE T1-continued

Melting point (mp) and/or LC/MS data for compounds for Formula (I):

| Entry | Compound name | Structure | $R_t$ (min) | [M + H] (measured) | Method | mp (° C.) |
|---|---|---|---|---|---|---|
| 1.170 | N-cyclopropyl-N-[(2E)-2-methoxyiminoethyl]-4-[5-(trifluoromethyl)-1,2,4-oxadiazol-3-yl]benzamide | 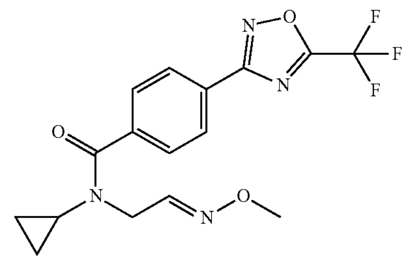 [SMILES: CO/N=C/CN(C(=O)c1ccc(-c2noc(C(F)(F)F)n2)cc1)C1CC1] | 1.553 | 369 | C | 60-62 |
| 1.171 | N-[(2E)-2-methoxyiminoethyl]-N-methyl-4-[5-(trifluoromethyl)-1,2,4-oxadiazol-3-yl]benzamide | 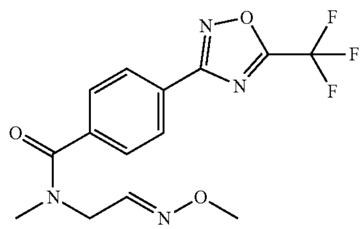 [SMILES: CO/N=C/CN(C)C(=O)c1ccc(-c2noc(C(F)(F)F)n2)cc1] | 1.460 | 342.9 | C | |

BIOLOGICAL EXAMPLES

General Examples of Leaf Disk Tests in Well Plates:

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

Mycelia fragments or conidia suspensions of a fungus prepared either freshly from liquid cultures of the fungus or from cryogenic storage, are directly mixed into nutrient broth. DMSO solutions of the test compound (max. 10 mg/ml) are diluted with 0.025% Tween20 by a factor of 50 and 10 µl of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example 1: Fungicidal Activity Against *Puccinia recondita* f. sp. *Tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% relative humidity (rh) under a light regime of 12 hours light/12 hours darkness in a climate cabinet and the activity of a compound was assessed as percent disease control compared to untreated when an appropriate level of disease damage appears in untreated check leaf segments (7 to 9 days after application).

The following compounds at 200 ppm in the applied formulation give at least 80% disease control in this test when compared to untreated control leaf disks under the same conditions, which show extensive disease development.

Compounds (from Table T1) 1.3, 1.4, 1.5, 1.6, 1.7, 1.8, 1.9, 1.10, 1.11, 1.12, 1.13, 1.14, 1.15, 1.20, 1.21, 1.25, 1.29, 1.30, 1.32, 1.33, 1.36, 1.37, 1.38, 1.40, 1.43, 1.45, 1.46, 1.48, 1.49, 1.50, 1.56, 1.58, 1.60, 1.61, 1.62, 1.64, 1.65, 1.66, 1.67, 1.68, 1.69, 1.70, 1.71, 1.72, 1.74, 1.75, 1.77, 1.78, 1.79, 1.80, 1.81, 1.82, 1.83, 1.89, 1.90, 1.91, 1.92, 1.93, 1.94, 1.95, 1.97, 1.100, 1.101, 1.102, 1.103, 1.104, 1.105, 1.106, 1.109, 1.110, 1.114, 1.116, 1.117, 1.118, 1.120, 1.121, 1.122, 1.123, 1.124, 1.125, 1.126, 1.132, 1.133, 1.135, 1.136, 1.137, 1.138, 1.139, 1.144, 1.145, 1.146, 1.148, 1.149, 1.150, 1.151, 1.152, 1.153, 1.154, 1.155, 1.157, 1.158, 1.159, 1.160, 1.161, 1.162, 1.163, 1.164, 1.165, 1.166, 1.167, and 1.168.

Example 2: Fungicidal Activity Against *Puccinia recondita* f. sp. *Tritici*/Wheat/Leaf Disc Curative (Brown Rust)

Wheat leaf segments cv. Kanzler are placed on agar in multiwell plates (24-well format). The leaf segments are then inoculated with a spore suspension of the fungus. Plates were stored in darkness at 19° C. and 75% relative humidity. The formulated test compound diluted in water was applied 1 day after inoculation. The leaf segments were incubated at 19° C. and 75% relative humidity under a light regime of 12 hours light/12 hours darkness in a climate cabinet and the activity of a compound was assessed as percent disease control compared to untreated when an appropriate level of disease damage appears in untreated check leaf segments (6 to 8 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19, 1.20, 1.21, 1.29, 1.32, 1.33, 1.36, 1.37, 1.38, 1.43, 1.46, 1.58, 1.60, 1.66, 1.70, 1.72, 1.74, 1.77, 1.78, 1.81, 1.82, 1.89, 1.91, 1.94, 1.95, 1.100, 1.101, 1.102, 1.104, 1.110, 1.114, 1.116, 1.117, 1.120, 1.125, 1.126, 1.133, 1.135, 1.138, 1.145, 1.146, 1.148, 1.149, 1.150, 1.151, 1.152, 1.153, 1.154, 1.156, 1.157, 1.158, 1.159, 1.160, 1.161, 1.162, 1.163, 1.164, 1.165, 1.166, 1.167, and 1.168.

Example 3: Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 hours light/12 hours and 75% rh. The activity of a compound is assessed as percent disease control compared to untreated when an appropriate level of disease damage appears in untreated check leaf disks (12 to 14 days after application).

The following compounds at 200 ppm in the applied formulation give at least 80% disease control in this test when compared to untreated control leaf disks under the same conditions, which show extensive disease development.

Compounds (from Table T1) 1.2, 1.3, 1.4, 1.5, 1.6, 1.7, 1.8, 1.9, 1.10, 1.11, 1.12, 1.13, 1.14, 1.15, 1.16, 1.17, 1.19, 1.21, 1.22, 1.23, 1.24, 1.25, 1.27, 1.30, 1.33, 1.34, 1.36, 1.40, 1.43, 1.45, 1.46, 1.47, 1.48, 1.50, 1.51, 1.52, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.78, 1.79, 1.80, 1.81, 1.82, 1.83, 1.84, 1.85, 1.89, 1.90, 1.91, 1.92, 1.94, 1.95, 1.100, 1.101, 1.102, 1.104, 1.110, 1.114, 1.116, 1.118, 1.121, 1.122, 1.123, 1.124, 1.126, 1.128, 1.132, 1.133, 1.134, 1.135, 1.138, 1.139, 1.144, 1.145, 1.146, 1.148, 1.149, 1.150, 1.151, 1.152, 1.153, 1.154, 1.155, 1.156, 1.157, 1.158, 1.159, 1.160, 1.161, 1.162, 1.163, 1.164, 1.165, 1.166, 1.167, and 1.168.

Example 4: Fungicidal Activity Against *Glomerella lagenarium* (*Colletotrichum lagenarium*) Liquid Culture/Cucumber/Preventative (Anthracnose)

Conidia of the fungus from cryogenic storage are directly mixed into nutrient broth (PDB—potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

The following compounds at 20 ppm in the applied formulation give at least 80% disease control in this test when compared to untreated control under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.14, 1.15, 1.17, 1.20, 1.22, 1.24, 1.25, 1.27, 1.29, 1.30, 1.32, 1.33, 1.34, 1.36, 1.37, 1.38, 1.40, 1.43, 1.45, 1.46, 1.47, 1.48, 1.49, 1.50, 1.51, 1.52, 1.56, 1.57, 1.58, 1.60, 1.62, 1.64, 1.65, 1.66, 1.67, 1.68, 1.69, 1.70, 1.71, 1.72, 1.74, 1.75, 1.77, 1.78, 1.79, 1.80, 1.81, 1.82, 1.83, 1.85, 1.89, 1.90, 1.91, 1.92, 1.93, 1.94, 1.95, 1.96, 1.100, 1.101, 1.102, 1.104, 1.106, 1.108, 1.109, 1.110, 1.112, 1.114, 1.116, 1.117, 1.118, 1.120, 1.121, 1.122, 1.123, 1.124, 1.125, 1.126, 1.128, 1.132, 1.133, 1.134, 1.135, 1.136, 1.137, 1.138, 1.139, 1.140, 1.144, 1.145, 1.146, 1.148, 1.149, 1.150, 1.151, 1.152, 1.153, 1.154, 1.155, 1.156, 1.157, 1.158, 1.159, 1.160, 1.161, 1.162, 1.163, 1.164, 1.165, 1.166, 1.167, and 1.168.

Example 5: Fungicidal Activity Against *Uromyces viciae-fabae*/Field Bean/Leaf Disc Preventative (*Faba*-Bean Rust)

Field bean leaf discs are placed on water agar in multiwell plates (96-well format) and 10 µl of the formulated test compound diluted in acetone and a spreader pipetted onto the leaf disc. Two hours after application leaf discs are inoculated by spraying a spore suspension on the lower leaf surface. The leaf discs are incubated in a climate cabinet at 22° C. with 18 hour day and 70% relative humidity. The activity of a compound is assessed as percent disease control compared to untreated when an appropriate level of disease damage appears in untreated check leaf disks (12 days after application).

The following compounds at 100 ppm in the applied formulation give at least 80% disease control in this test when compared to untreated control leaf discs under the same conditions, which show extensive disease development.

Compounds (from Table T1) 1.1, 1.2, 1.3, and 1.4.

The invention claimed is:
1. A compound of formula (I)

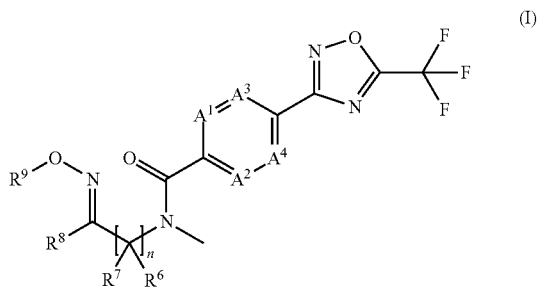

wherein
n is 0;
each of $A^2$, $A^3$ and $A^4$ represents C—H, and $A^1$ represents $CR^1$, wherein $R^1$ is fluoro;
$R^5$ is hydrogen;
$R^8$ represents $C_{1-6}$alkyl;
$R^9$ represents hydrogen, $C_{1-12}$alkyl, $C_{2-6}$alkenyl, $C_{2-6}$alkynyl, $C_{1-4}$haloalkyl, $C_{2-4}$haloalkenyl, hydroxy$C_{1-4}$alkyl, cyano$C_{1-4}$alkyl, $C_{1-4}$alkoxy$C_{1-4}$alkyl, hydroxycarbonyl$C_{1-4}$alkyl, $C_{1-4}$alkoxycarbonyl-$C_{1-4}$alkyl, amino$C_{1-4}$alkyl, $C_3$-scycloalkyl, $C_{3-8}$cycloalkyl$C_{1-3}$alkyl, phenyl, phenyl$C_{1-4}$alkyl, heterocyclyl or heterocyclylC$_{1-4}$alkyl wherein the heterocyclyl moiety is a 4- to 6-membered non-aromatic ring which comprises 1, 2 or 3 heteroatoms individually selected from N, O and S, and wherein C$_{3-8}$cycloalkyl, phenyl and heterocyclyl moieties are optionally substituted by 1, 2, or 3 substituents, which may be the same or different, selected from R$^{10}$, or 1, 2, 3, 4 or 5 substituents, which may be the same or different, selected from R$^{11}$;

R$^{10}$ represents cyano, nitro, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{1-6}$alkylthio, C$_{1-4}$alkoxycarbonylC$_{1-4}$alkyl, hydroxycarbonylC$_{1-4}$alkyl, or C$_{3-8}$cycloalkyl; and R$^{11}$ represents halogen;

or a salt or an N-oxide thereof.

2. A compound of formula (I):

wherein n is 1;

each of A$^2$, A$^3$ and A$^4$ represents C—H, and A$^1$ represents CR$^1$, wherein R$^1$ is fluoro;

R$^5$ is hydrogen;

R$^6$ is hydrogen and R$^7$ is selected from methyl and methoxy;

R$^8$ represents hydrogen;

R$^9$ represents hydrogen, C$_{1-12}$alkyl, C$_{2-6}$alkenyl, C$_{2-6}$alkynyl, C$_{1-4}$haloalkyl, C$_{2-4}$haloalkenyl, hydroxyC$_{1-4}$alkyl, cyanoC$_{1-4}$alkyl, C$_{1-4}$alkoxyC$_{1-4}$alkyl, hydroxycarbonylC$_{1-4}$alkyl, C$_{1-4}$alkoxycarbonylC$_{1-4}$alkyl, aminoC$_{1-4}$alkyl, C$_{3-8}$cycloalkyl, C$_{3-8}$cycloalkylC$_{1-3}$alkyl, phenyl, phenylC$_{1-4}$alkyl, heterocyclyl or heterocyclylC$_{1-4}$alkyl wherein the heterocyclyl moiety is a 4- to 6-membered non-aromatic ring which comprises 1, 2 or 3 heteroatoms individually selected from N, O and S, and wherein C$_{3-8}$cycloalkyl, phenyl and heterocyclyl moieties are optionally substituted by 1, 2, or 3 substituents, which may be the same or different, selected from R$^{10}$, or 1, 2, 3, 4 or 5 substituents, which may be the same or different, selected from R$^{11}$;

R$^{10}$ represents cyano, nitro, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{1-6}$alkylthio, C$_{1-4}$alkoxycarbonylC$_{1-4}$alkyl, hydroxycarbonylC$_{1-4}$alkyl, or C$_{3-8}$cycloalkyl; and R$^{11}$ represents halogen;

or a salt or an N-oxide thereof.

3. A compound of formula (I):

wherein n is 2;

each of A$^2$, A$^3$ and A$^4$ represents C—H, and A$^1$ represents CR$^1$, wherein R$^1$ is fluoro;

R$^5$ is hydrogen;

R$^6$ and R$^7$ are independently selected from hydrogen, cyano, C$_{1-4}$alkyl, C$_{1-4}$haloalkyl, C$_{3-6}$cycloalkyl and C$_{1-4}$alkoxy;

R$^8$ represents hydrogen;

R$^9$ represents hydrogen, C$_{1-12}$alkyl, C$_{2-6}$alkenyl, C$_{2-6}$alkynyl, C$_{1-4}$haloalkyl, C$_{2-4}$haloalkenyl, hydroxyC$_{1-4}$alkyl, cyanoC$_{1-4}$alkyl, C$_{1-4}$alkoxyC$_{1-4}$alkyl, hydroxycarbonylC$_{1-4}$alkyl, C$_{1-4}$alkoxycarbonylC$_{1-4}$alkyl, aminoC$_{1-4}$alkyl, C$_{3-8}$cycloalkyl, C$_{3-8}$cycloalkylC$_{1-3}$alkyl, phenyl, phenylC$_{1-4}$alkyl, heterocyclyl or heterocyclylC$_{1-4}$alkyl wherein the heterocyclyl moiety is a 4- to 6-membered non-aromatic ring which comprises 1, 2 or 3 heteroatoms individually selected from N, O and S, and wherein C$_{3-8}$cycloalkyl, phenyl and heterocyclyl moieties are optionally substituted by 1, 2, or 3 substituents, which may be the same or different, selected from R$^{10}$, or 1, 2, 3, 4 or 5 substituents, which may be the same or different, selected from R$^{11}$;

R$^{10}$ represents cyano, nitro, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{1-6}$alkylthio, C$_{1-4}$alkoxycarbonylC$_{1-4}$alkyl, hydroxycarbonylC$_{1-4}$alkyl, or C$_{3-8}$cycloalkyl; and R$^{11}$ represents halogen;

or a salt or an N-oxide thereof.

4. The compound according to claim 3, wherein R$^6$ and R$^7$ are independently selected from hydrogen, C$_{1-4}$alkyl and C$_{1-4}$alkoxy.

5. The compound according to claim 3, wherein R$^6$ and R$^7$ are independently selected from hydrogen, methyl and methoxy.

6. The compound according to any one of claims 1, 2, and 3, wherein R$^9$ is hydrogen, C$_{1-12}$alkyl, C$_{1-4}$haloalkyl, hydroxyC$_{1-4}$alkyl, C$_{2-6}$alkenyl, C$_{2-6}$alkynyl, C$_{2-4}$haloalkenyl, C$_{1-4}$alkoxycarbonylC$_{1-4}$alkyl, C$_{3-8}$cycloalkylC$_{1-3}$alkyl, phenyl, benzyl, oxetanyl, tetrahydrofuranyl or tetrahydropyranyl, wherein phenyl moieties are optionally substituted by 1, 2 or 3 substituents, which may be the same or different, selected from R$^{10}$, or 1, 2, 3, 4 or 5 substituents, which may be the same or different, selected from R$^{11}$.

7. The compound according to claim 6, wherein R$^{10}$ is selected from methyl, nitro, methoxy, methoxycarbonylmethyl and trifluoromethyl and R$^{11}$ is selected from fluoro, chloro and bromo.

8. The compound according to any one of claims 1, 2, and 3, wherein $R^9$ is hydrogen, $C_{1-6}$alkyl, $C_{1-4}$haloalkyl, $C_{2-6}$alkenyl, $C_{2-6}$alkynyl, or $C_{3-8}$cycloalkyl$C_{1-3}$alkyl.

9. The compound according to claim 8, wherein $R^9$ is methyl, ethyl, isopropyl, t-butyl, 2,2,2-trifluoroethyl, or cyclopropylmethyl.

10. An agrochemical composition comprising a fungicidally effective amount of a compound of formula (I) according to any one of claims 1, 2, and 3.

11. The composition according to claim 10, further comprising at least one additional active ingredient and/or an agrochemically-acceptable diluent or earner.

12. A method of controlling infestation of useful plants by phytopathogenic microorganisms, comprising, applying a fungicidally effective amount of a compound of formula (I) according to any one of claims 1, 2, and 3, or a composition comprising this compound as active ingredient, is applied to the plants, to parts thereof or the locus thereof.

13. The compound according to any one of claims 1, 2, and 3, wherein $R^9$ represents $C_{3-8}$cycloalkyl, $C_{3-8}$cycloalkyl$C_{1-3}$alkyl, phenyl, phenyl$C_{1-4}$alkyl, heterocyclyl or heterocyclyl$C_{1-4}$alkyl wherein the heterocyclyl moiety is a 4- to 6-membered non-aromatic ring which comprises 1, 2 or 3 heteroatoms individually selected from N, O and S, and wherein $C_{3-8}$cycloalkyl, phenyl and heterocyclyl moieties are optionally substituted by 1, 2, or 3 substituents, which may be the same or different, selected from $R^{10}$, or 1, 2, 3, 4 or 5 substituents, which may be the same or different, selected from $R^{11}$;

$R^{10}$ represents cyano, nitro, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{1-6}$alkylthio, $C_{1-4}$alkoxycarbonyl$C_{1-4}$alkyl, hydroxycarbonyl$C_{1-4}$alkyl, or $C_{3-8}$cycloalkyl; and $R^{11}$ represents halogen.

14. The compound according to any one of claims 1, 2, and 3, wherein $R^9$ represents hydroxy$C_{1-4}$alkyl, cyano-$C_{1-4}$alkyl, $C_{1-4}$alkoxy$C_{1-4}$alkyl, hydroxycarbonyl$C_{1-4}$alkyl, $C_{1-4}$alkoxycarbonyl$C_{1-4}$alkyl, or amino$C_{1-4}$alkyl.

15. A compound selected from the group consisting of:

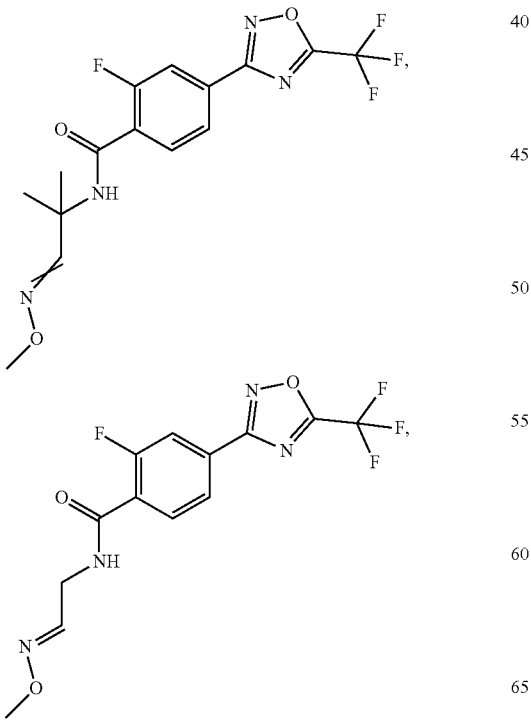

-continued

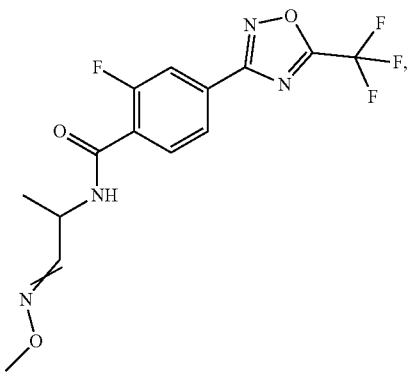

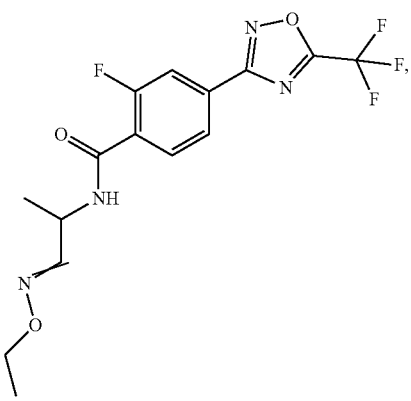

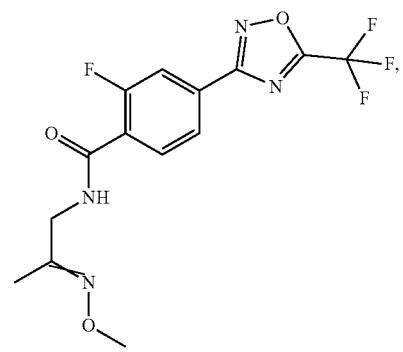 [SMILES: CONC(C)CNC(=O)c1ccc(-c2noc(C(F)(F)F)n2)cc1F]

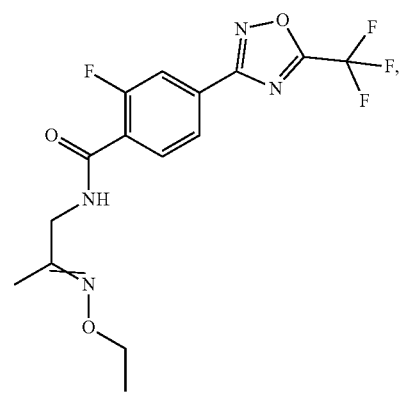

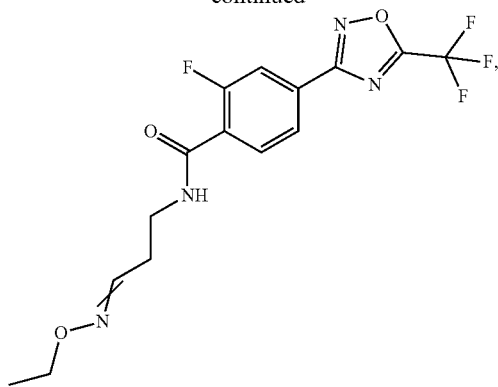
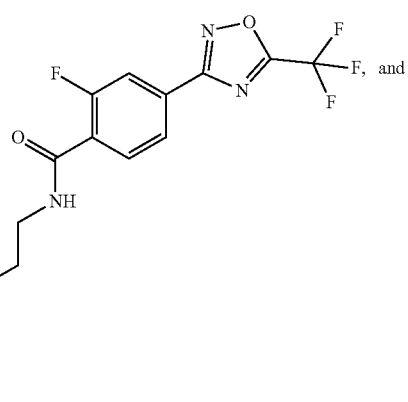
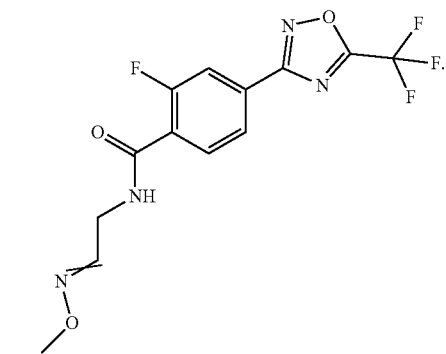
16. The compound of claim 15, wherein the compound is selected from the group consisting of:
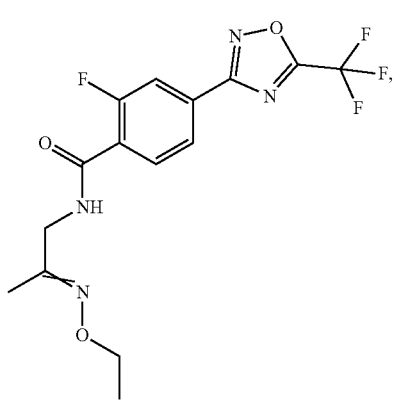
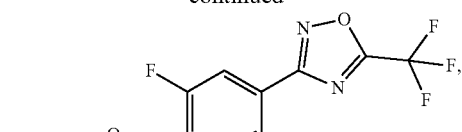
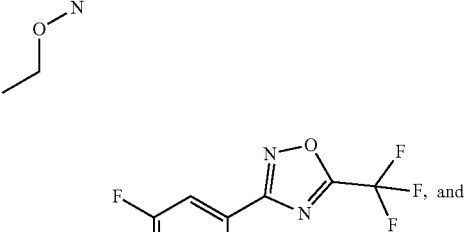
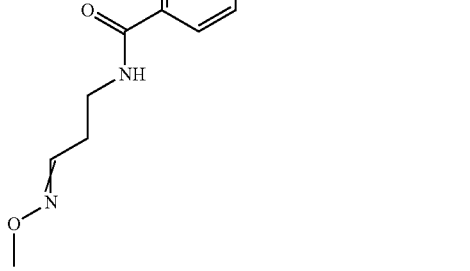
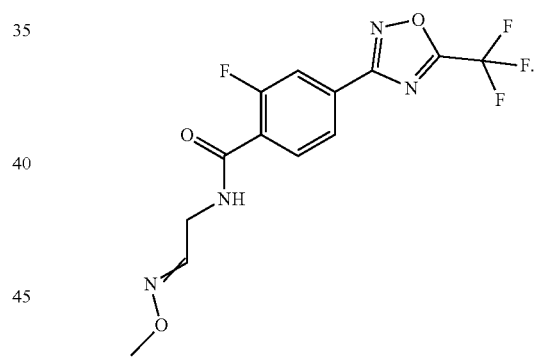
17. The compound of claim 15, wherein the compound is selected from the group consisting of:
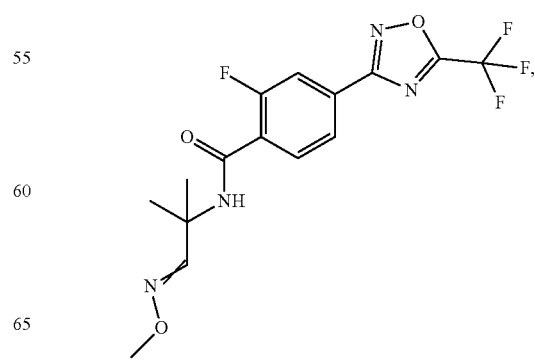

221
-continued
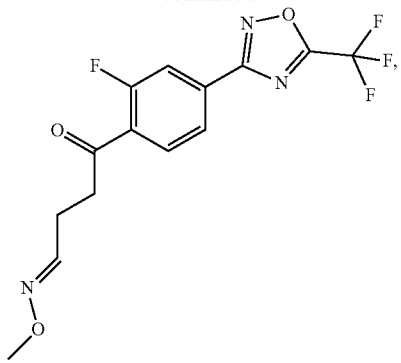
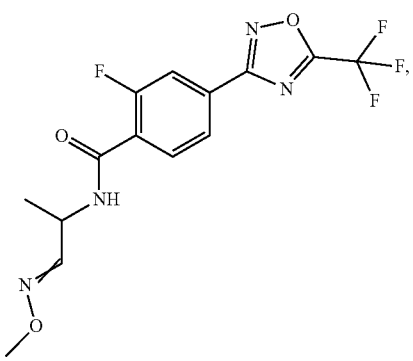
222
-continued
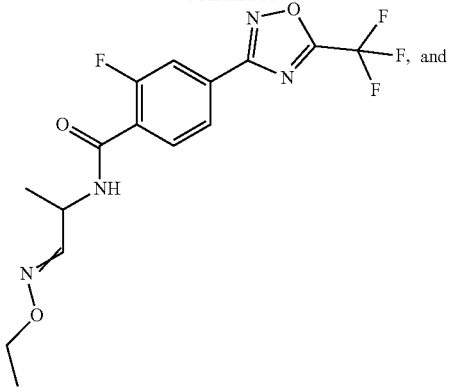
* * * * *